US012258632B2

(12) United States Patent
Markowitz et al.

(10) Patent No.: US 12,258,632 B2
(45) Date of Patent: *Mar. 25, 2025

(54) METHODS AND COMPOSITIONS FOR DETECTING ESOPHAGEAL NEOPLASIAS AND/OR METAPLASIAS IN THE ESOPHAGUS

(71) Applicant: Case Western Reserve University, Cleveland, OH (US)

(72) Inventors: Sanford D. Markowitz, Pepper Pike, OH (US); Helen Moinova, Beachwood, OH (US); Amitabh Chak, University Heights, OH (US); Joseph Willis, Shaker Heights, OH (US); Thomas LaFramboise, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/315,405

(22) PCT Filed: Jul. 5, 2017

(86) PCT No.: PCT/US2017/040708
§ 371 (c)(1),
(2) Date: Jan. 4, 2019

(87) PCT Pub. No.: WO2018/009535
PCT Pub. Date: Jan. 11, 2018

(65) Prior Publication Data
US 2019/0309372 A1    Oct. 10, 2019

Related U.S. Application Data

(60) Provisional application No. 62/358,701, filed on Jul. 6, 2016.

(51) Int. Cl.
C12Q 1/68        (2018.01)
C12Q 1/6827      (2018.01)
C12Q 1/6853      (2018.01)
C12Q 1/6886      (2018.01)
G01N 33/574      (2006.01)

(52) U.S. Cl.
CPC ......... *C12Q 1/6886* (2013.01); *C12Q 1/6827* (2013.01); *C12Q 1/6853* (2013.01); *G01N 33/574* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| 7,485,420 | B2 | 2/2009 | Markowitz |
| 7,964,353 | B2 | 6/2011 | Markowitz |
| 8,221,977 | B2 | 7/2012 | Markowitz |
| 8,415,100 | B2 | 4/2013 | Markowitz et al. |
| 9,322,065 | B2 | 4/2016 | Renard et al. |
| 9,580,754 | B2 | 2/2017 | Markowitz et al. |
| 10,400,286 | B2 | 9/2019 | Markowitz |
| 10,450,615 | B2 | 10/2019 | Markowitz et al. |
| 11,136,629 | B2 | 10/2021 | Markowitz et al. |
| 2007/0161031 | A1 | 7/2007 | Trinklein et al. |
| 2008/0220433 | A1 | 9/2008 | Ahlquist et al. |
| 2010/0009359 | A1 | 1/2010 | Markowitz |
| 2010/0151468 | A1 | 6/2010 | Esteller et al. |
| 2012/0094287 | A1 | 4/2012 | Markowitz et al. |
| 2014/0206565 | A1 | 7/2014 | Selaru et al. |
| 2016/0317132 | A1 | 11/2016 | Markowitz et al. |
| 2017/0369948 | A1 | 12/2017 | Markowitz et al. |
| 2019/0136325 | A1 | 5/2019 | Markowitz et al. |

FOREIGN PATENT DOCUMENTS

| EP | 2626435 A1 | 8/2013 | |
| JP | 2004-505612 A | 2/2004 | |
| JP | 2008283947 A | 11/2008 | |
| WO | WO-2010118016 A2 | 10/2010 | |
| WO | WO-2012/178074 A1 | 12/2012 | |
| WO | WO-2013171504 A1 | 11/2013 | |
| WO | WO-2014159652 A2 | 10/2014 | |
| WO | WO2016109712 * | 7/2016 | ............... C12Q 1/68 |
| WO | WO-2016109712 A1 | 7/2016 | |
| WO | WO-2018009535 A1 | 1/2018 | |

OTHER PUBLICATIONS

Kitkumthorn et al. Cyclin A1 promoter hypermethylation in human papillomavirus-associated cervical cancer (2006) BMC Cancer, vol. 6, No. 55, 9 pages. (Year: 2006).*
Tokumaru et al. Aberrant Promoter Hypermethylation of Cyclin A1 in Cancer (2006) Japanese Journal of Head and Neck Cancer 32 (4) 410-416. (Year: 2006).*
Shaw et al. The Role of Pyrosequencing in Head and Neck Cancer Epigenetics (2008) Arch Otolaryngol Head Neck Surg, vol. 134, No. 3, 251-256. (Year: 2008).*
Lin et al. (J Gastrointest Oncol 2015;6(1):3-19) (Year: 2015).*
"Scientists Can Make Copies of a Gene through PCR", 2014, obtained from Sitable by Nature Education, Downloaded on May 31, 2023 from https://www.nature.com/scitable/topicpage/scientists-can-make-copies-of-a-gene-6525968/ (herein referred to as "Nature Education") (Year: 2014).*
Kitkumthom et al. BMC Cancer vol. 6, No. 55, 9 pages. (Year: 2006).*

(Continued)

Primary Examiner — Juliet C Switzer
(74) Attorney, Agent, or Firm — White & Case LLP

(57) ABSTRACT

The disclosure provides methods for identifying genomic loci (e.g., vimentin and/or SqBE18) that are differentially methylated in metaplasias (e.g., Barrett's esophagus) and/or neoplastic cancers (e.g., esophageal cancers). Identification of methylated genomic loci has numerous uses, including for example, to characterize disease risk, to predict responsiveness to therapy, to non-invasively diagnose subjects and to treat subjects determined to have gastrointestinal metaplasias and/or neoplasias.

14 Claims, 11 Drawing Sheets

Specification includes a Sequence Listing.

(56) References Cited

OTHER PUBLICATIONS

Lee et al. (Cancer Lett. Nov. 1, 2013; 340(2): doi:10.1016/j.canlet. 2012.10.040. sixteen pages) (Year: 2013).*
Tokumaru et al. 2006. Japanese Journal of Head and Neck Cancer 32(4) 410-416. (Year: 2006).*
Nava et al. (Lasers in Surgery and Medicine 43:705-712 (2011)) (Year: 2011).*
Andersson, et al., "Filtration Device for On-Site Collection, Storage and Shipment of Cells from Urine and Its Application to DNA-Based Detection of Bladder Cancer," PLOS One, vol. 10(7): e0131889 (2015).
Andersson, et al., "Size-Based Enrichment of Exfoliated Tumor Cells in Urine Increases the Sensitivity for DNA-Based Detection of Bladder Cancer," PLOS One, vol. 9(4): e94023 (2014).
Brait, et al., "Aberrant Promoter Methylation of Multiple Genes during Pathogenesis of Bladder Cancer," Cancer Epidemiology, Biomarkers and Prevention, vol. 17(1): 2786-2794 (2008).
Brait, et al., "Association of Promoter Methylation of VGF and PGP9.5 with Ovarian Cancer Progression," PLoS One, vol. 8(9): e70878 (2013).
Carvalho, et al., "Detection of Promoter Hypermethylation in Salivary Rinses as a Biomarker for Head and Neck Squamous Cell Carcinoma Surveillance," Clinical Cancer Research, vol. 17(14): 4782-4789 (2011).
Carvalho, et al., "TGFβR2 aberrant methylation is a potential prognostic marker and therapeutic target in multiple myeloma," International Journal of Cancer, vol. 125: 1985-1991 (2009).
Chujan, et al., "CCNA1 Promoter Methylation: a Potential Marker for Grading Papanicolaou Smear Cervical Squamous Intraepithelial Lesions," Asian Pacific Journal of Cancer Prevention, vol. 15(18): 7971-7975 (2014).
Colacino, et al., "Comprehensive Analysis of DNA Methylation in Head and Neck Squamous Cell Carcinoma Indicates Differences by Survival and Clinicopathologic Characteristics," PLoS One, vol. 8(1): e54742 (2013).
Galipeau, Patricia C., "Barrett's Esophagus and Esophael Adenocarcinoma Epigenetic Biomarker Discovery Using Infinium Methylation," illumina iCommunity Newsletter: 3-4 (2008).
Gonzalgo, et al., "Rapid quantitation of methylation differences at specific sites using methylation-sensitive single nucleotide primer extension (Ms-SNuPE)," Nucleic Acids Research, vol. 25(12): 2529-2531 (1997).
Hall, et al., "p16 Promoter Methylation is a Potential Predictor of Malignant Transformation in Oral Epithelial Dysplasia," Cancer Epidemiology, Biomarkers and Prevention, vol. 17(8): 2174-2179 (2008).
Heller, et al., "Genome-Wide Transcriptional Response to 5-Aza-2'-Deoxycytidine and Trichostatin A in Multiple Myeloma Cells," Cancer Research, vol. 68(1): 44-54 (2008).
Kaz et al. "Unique Methylation Signatures and Molecular Subclasses of Barrett's Esophagus and Esophageal Adenocarcinoma Revealed by Methylation Array Analysis," Gastroenterology vol. 140 (5) Suppl. 1, S818 (May 2011).
Kaz, et al. "Differential methylation in gene bodies and promoters in barrett's esophagus and esophageal adenocarcinoma revealed by genome-wide methylation array analysis," Gastroenterology, vol. 144 (5) Supp. 1 (May 2013).
Kaz, A.M. et al., "DNA methylation profiing in Barrett's esophagus and esophageal adenocarcinoma reveals unique methylation signatures and molecular subclasses," Epigenetics, Landes Bioscience, US, vol. 6(12): 1403-1412 (2011).
Kim, et al., "Histone demethylase JMJD2B-mediated cell proliferation regulated by hypoxia and radiation in gastric cancer cell," Biochimica et Biophysica Acta, vol. 1819: 1200-1207 (2012).
Kitkumthorn, et al., "Cyclin A1 promoter hypermethylation in human papillomavirus-associated cervical cancer," BMC Cancer, vol. 6(55) 9 pages (2006).
Klajic, et al., "DNA Methylation Status of Key Cell-Cycle Regulators Such as CDKNA2/p16 and CCNA1 Correlates with Treatment Response to Doxorubicin and 5-Fluorouracil in Locally Advanced Breast Tumors," Clinical Cancer Research, vol. 20(24): 6357-6366 (2014).
Li, et al., "A network-based, integrative approach to identify genes with aberrant co-methylation in colorectal cancer," Molecular BioSystems, vol. 10: 180-190 (2014).
Li, et al., "Sensitive digital quantification of DNA methylation in clinical samples," Nature Biotechnology, vol. 27(9): 858-863 (2009).
Li, et al., "Supplemental files for 'A network-based, integrative approach to identify genes with aberrant co-methylation in colorectal cancer'," Electronic Supplementary Material (ESI) for Molecular BioSystems, 16 pages (2013).
Liang, et al., "Integrative Identification of Epstein-Barr Virus-Associated Mutations and Epigenetic Alterations in Gastric Cancer," Gastroenterology, vol. 147(6): 1350-1362 (2014).
Lim, et al., "Cervical dysplasia: Assessing methylation status (Methylight) of CCNA1, DAPK1, HS3ST2, PAX1 and TFPI2 to improve diagnostic accuracy," Gynecologic Oncology, vol. 119: 225-231 (2010).
Lin et al. "Deletion or epigenetic silencing of AJAP1 on 1p36 in glioblastoma," Mol Cancer Res. vol. 10, pp. 208-217 (Jan. 2012).
Loh, et al., "DNA methylation subgroups and the CpG island methylator phenotype in gastric cancer: a comprehensive profiling approach," BMC Gastroenterology, vol. 14(55) 11 pages (2014).
Longo, et al., "Evaluation of the methylation profile of exfoliated cell samples from patients with head and neck squamous cell carcinoma," Head and Neck, vol. 36: 631-637 (2014).
Maldonado, et al., "An epigenetic marker panel for recurrence risk prediction of low grade papillary urothelial cell carcinoma (LGPUCC) and its potential use for surveillance after transurethral resection using urine," Oncotarget, vol. 5(14): 5218-5233 (2014).
Moinova et al, "Aberrant Vimentin Methylation is Characteristic of Upper Gastrointestinal Pathologies," Cancer Epidemiology, Biomarkers and Prevention, vol. 21(4): 594-600 Feb. 7, 2012.
Müller, et al., "Methylation of the Cyclin A1 Promoter Correlates with Gene Silencing in Somatic Cell Lines, while Tissue-Specific Expression of Cyclin A1 Is Methylation Independent," Molecular and Cell Biology, vol. 20(9): 3316-3329 (2000).
New England Biolabs, Random Primers, p. 111, 96/97 catalog (1997).
Ongenaert, et al., "Discovery of DNA methylation markers in cervical cancer using relaxation ranking," BMC Medical Genomics, vol. 1(57) 15 pages (2008).
Rettori, et al., "Prognostic significance of TIMP3 hypermethylation in post-treatment salivary rinse from head and neck squamous cell carcinoma patients," Carcinogenesis, vol. 34(1): 20-27 (2013).
Rettori, et al., "TIMP3 and CCNA1 hypermethylation in HNSCC is associated with an increased incidence of second primary tumors," Journal of Translational Medicine, vol. 11(316) 11 pages (2013).
Sartor, et al., "Genome-wide methylation and expression differences in HPV(+) and HPV(−) squamous cell carcinoma cell lines are consistent with divergent mechanisms of carcinogenesis," Epigenetics, vol. 6(6): 777-787 (2011).
Shah, et al. "Endoscopic options for early stage esophageal cancer", Journal of; Gastrointestinal Oncology. 2015, vol. 6, pp. 20-30 (2015).
Shaw, et al., "Methylation enrichment pyrosequencing: combining the specificity of MSP with validation by pyrosequencing," Nucleic Acids Research, vol. 34(11): e78 (2006).
Shaw, et al., "Promoter methylation of P16, RARβ, E-cadherin, cyclin A1 and cytoglobin in oral cancer: quantitative evaluation using pyrosequencing," British Journal of Cancer, vol. 94(4): 561-568 (2006).
Starlard-Davenport, et al., "Restoration of the methylation status of hypermethylated gene promoters by microRNA-29b in human breast cancer: A novel epigenetic therapeutic approach," Journal of Carcinogenesis, vol. 12(15) 18 pages (2013).
Stockdale et al. "Epigenetic alterations in Barrett's esophagus and esophageal adenocarcinoma: Identification and evaluation of potential biomarkers," Cancer Res., vol. 74, 19 Suppl, (Oct. 1, 2014).
Sun, et al., "Comparison of Promoter Hypermethylation Pattern in Salivary Rinses Collected with and without an Exfoliating Brush with Patients with HNSCC," PLOS One, vol. 7(3): e33642 (2012).

(56) References Cited

OTHER PUBLICATIONS

Sun, et al., "Detection of TIMP3 promoter hypermethylation in salivary rinse as an independent predictor of local recurrence-free survival in head and neck cancer," Clinical Cancer Research, vol. 18(4): 1082-1091 (2012).

Tan, et al., "Quantitative methylation analyses of resection margins predict local recurrences and disease-specific deaths in patients with head and neck squamous cell carcinomas," British Journal of Cancer, vol. 99(2): 357-363 (2008).

Tokumaru, et al., "Inverse Correlation between Cyclin A1 Hypermethylation and p53 Mutation in Head and Neck Cancer Identified by Reversal of Epigenetic Silencing," Cancer Research, vol. 64: 5982-5987 (2004).

Weiss, et al., "Promoter Methylation of Cyclin A1 Is Associated With Human Papillomavirus 16 Induced Head and Neck Squamous Cell Carcinoma Independently of p53 Mutation," Molecular Carcinogenesis, vol. 50: 680-688 (2011).

Wu, et al. "Aberrant gene methylation in the neoplastic progression of Barrett's; esophagus: identification of candidate diagnostic markers", Gastroenterology, vol. 140, p. S-222 (2011).

Xiong, et al., "COBRA: a sensitive and quantitative DNA methylation assay," Nucleic Acids Research, vol. 25(12): 2532-2534 (1997).

Xu, E. et al., "Genome-wide methylation analysis shows similar patterns in Barrett's Esophagus and Esophageal Adenocarcinoma," Carcinogenesis, vol. 34(12): 2750-2756 Aug. 29, 2013.

Yanatatsaneejit, et al., "Human Papillomavirus's Physical State and Cyclin A1 Promoter Methylation in Cervical Cancer," International Journal of Gynecological Cancer, vol. 21(5): 902-906 (2011).

Yanatatsaneejit, et al., "Promoter hypermethylation of CCNA1, RARRES1, and HRASLS3 in nasopharyngeal carcinoma," Oral Oncology, vol. 44: 400-406 (2008).

Yang, et al., "Gene promoter methylation patterns throughout the process of cervical carcinogenesis," Cellular Oncology, vol. 32: 131-143 (2010).

Yang, et al., "Methylation Markers for CCNA1 and C13ORF18 Are Strongly Associated with High-Grade Cervical Intraepithelial Neoplasia and Cervical Cancer in Cervical Scrapings," Cancer Epidemiology, Biomarkers and Prevention, vol. 18(11): 3000-3007 (2009).

Yu, et al., "A Novel Set of DNA Methylation Markers in Urine Sediments for Sensitive/Specific Detection of Bladder Cancer," Clinical Cancer Research, vol. 13(24): 7296-7304 (2007).

Adams, et al., "Promotor Methylation in Cytology Specimens as an Early Detection Marker for Esophageal Squamous Dysplasia and Early Esophageal Squamous Cell Carcinoma", Cancer Prevention Research, 1(5), Oct. 2008.

Redshaw, et al., "Quantification of epigenetic biomarkers: an evaluation of established and emerging methods for DNA methylation analysis", BMC Genomics, 15:1174, (2014).

Tokumaru, et al., "Aberrant Promoter Hypermethylation of Cyclin A1 in Cancer", Japanese Journal of Head and Neck Cancer, 32(4) pp. 410-416 (2006) (with English Abstract).

GenBank record having accession AF124143. Apr. 20, 1999. *Homo sapiens* cyclin A1 gene, promoter region, exon 1, and partial cds 2 pages (1999).

Dennis, J. et al., Aberrant Gene Methylation in the Neoplastic Progression of Barrett's Esophagus: Identification of Candidate Diagnostic Markers, Gastroenterology, vol. 140(5), Supplement 1 (Sa1092): S-222 (2011).

Haipeng, Bai et al., "The Research Progress of Esophageal Cancel and Its Treatment," Journal of Baotou Medical College, vol. 30(3): (3 pages) (2014).

International Search Report and Written Opinion for Application PCT/US2015/068131 dated Jun. 6, 2016, 6 pages.

International Search Report and Written Opinion for Application PCT/US2017/040708 dated Aug. 28, 2017, 8 pages.

Koss et al., Evaluation of Esophageal Cytology Using a Neural Net-Based Interative Scanning System (the PAPNET System); Am J Clin Pathol 1998; 109:549-557 (Year: 1998).

Lee et al., "Analyzing the Cancer Methylome through targeted bisulfite sequencing", Cancer Lett. Nov. 1, 2013; 340(2); 16 pages (2013).

Kato, H. & Nakajima, M., "Treatments for esophageal cancer: a review", Gen Thorac Cardiovasc Surg., vol. 61(6): 330-335 (Sep. 4, 2013).

Adams et al., "Promoter Methylation in Cytology Specimens as an Early Detection Marker for Esophageal Squamous Dysplasia and Early Esophageal Squamous Cell Carcinoma", Cancer Prevention Research, vol. 1: 357-361 (2008).

\* cited by examiner

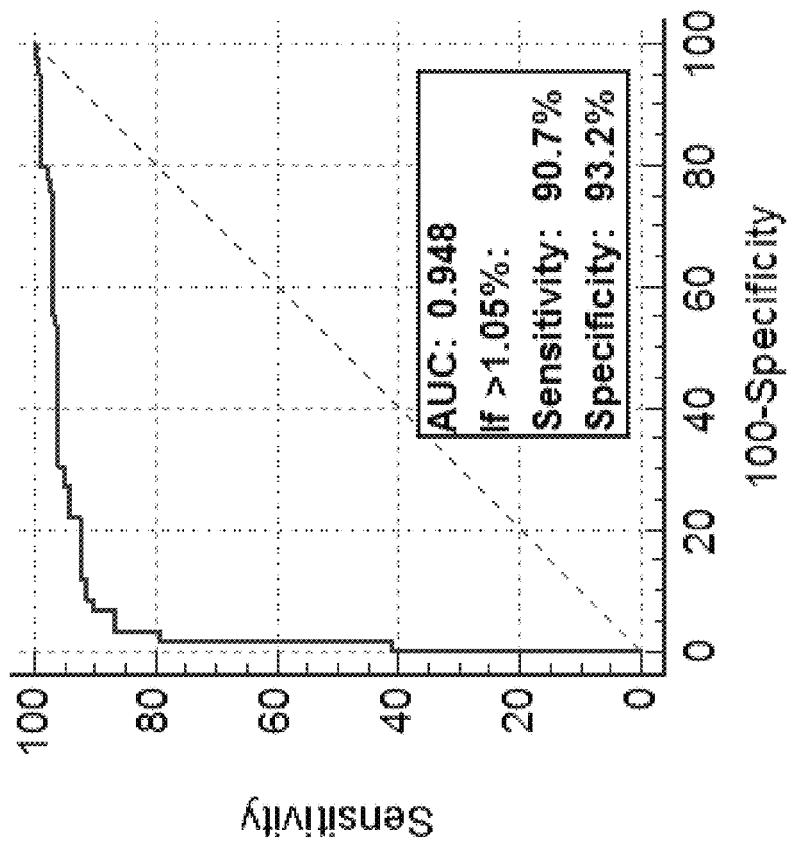

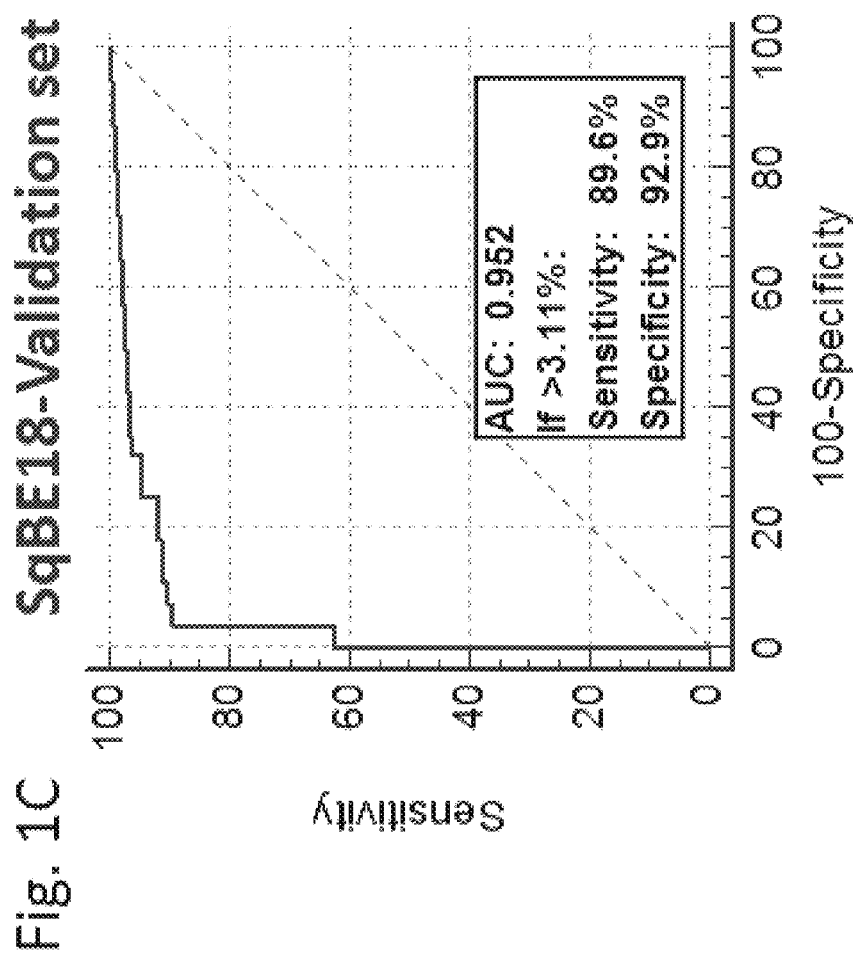

| | mVIM (Positive if > 1.05%) | | mSqBE18 (Positive if > 3.11%) | | Either mVIM or mSqBE18 Positive (one-marker fails censored) | | Either mVIM or mSqBE18 Positive (one-marker fails counted) | |
|---|---|---|---|---|---|---|---|---|
| | % | # | % | # | % | # | % | # |
| Specificity Control GEJ (GERD, EE, other) | 93.2% | 59 | 98.4% | 61 | 91.4% | 58 | 91.9% | 62 |
| Sensitivity ND SSBE | 91.7% | 12 | 83.3% | 12 | 91.7% | 12 | 91.7% | 12 |
| Sensitivity ND LSBE | 88.9% | 18 | 76.5% | 17 | 93.8% | 16 | 89.5% | 19 |
| Sensitivity NDBE combined | 90.0% | 30 | 79.3% | 29 | 92.9% | 28 | 90.3% | 31 |
| Sensitivity LGD | 100.0% | 7 | 87.5% | 8 | 100.0% | 7 | 100.0% | 8 |
| Sensitivity HGD | 100.0% | 10 | 100.0% | 10 | 100.0% | 10 | 100.0% | 10 |
| Sensitivity dysplastic BE combined | 100.0% | 17 | 94.4% | 18 | 100.0% | 17 | 100.0% | 18 |
| Sensitivity Cancer | 88.3% | 60 | 95.1% | 61 | 96.6% | 59 | 96.8% | 62 |
| All cases (NDBE through cancer) combined | 90.7% | 107 | 90.7% | 108 | 96.2% | 104 | 95.5% | 111 |

Fig. 3

| | mVIM (Positive if > 1.05%) | | mSqBE18 (Positive if > 3.11%) | | Either mVIM or mSqBE18 Positive (one-marker fails censored) | | Either mVIM or mSqBE18 Positive (one-marker fails counted) | |
|---|---|---|---|---|---|---|---|---|
| | % | # | % | # | % | # | % | # |
| Specificity Control GEJ (GERD, EE, other) | 92.6% | 27 | 92.9% | 28 | 88.5% | 26 | 89.7% | 29 |
| Sensitivity ND SSBE | 84.2% | 19 | 72.2% | 18 | 83.3% | 18 | 84.2% | 19 |
| Sensitivity ND LSBE | 100.0% | 22 | 86.4% | 22 | 100.0% | 22 | 100.0% | 22 |
| Sensitivity NDBE combined | 92.7% | 41 | 80.0% | 40 | 92.5% | 40 | 92.7% | 41 |
| Sensitivity LGD | 92.3% | 26 | 91.7% | 24 | 95.8% | 24 | 92.3% | 26 |
| Sensitivity HGD | 76.9% | 13 | 100.0% | 13 | 100.0% | 13 | 100.0% | 13 |
| Sensitivity dysplastic BE combined | 87.2% | 39 | 94.6% | 37 | 97.3% | 37 | 94.9% | 39 |
| Sensitivity Cancer | 94.6% | 37 | 94.7% | 38 | 94.6% | 37 | 94.7% | 38 |
| All cases (NDBE through cancer) combined | 91.5% | 117 | 89.6% | 115 | 94.7% | 114 | 94.1% | 118 |

Fig. 4

|  | mVIM (Positive if > 1.05%) | | mSqBE18 (Positive if > 3.11%) | | Either mVIM or mSqBE18 Positive | |
|---|---|---|---|---|---|---|
|  | % | # | % | # | % | # |
| Specificity Control GEJ (GERD, EE, other) | 93.0% | 86 | 96.6% | 89 | 90.5% | 84 |
| Sensitivity ND SSBE | 87.1% | 31 | 76.7% | 30 | 87.1% | 31 |
| Sensitivity ND LSBE | 95.0% | 40 | 82.1% | 39 | 95.1% | 41 |
| Sensitivity NDBE combined | 91.5% | 71 | 79.7% | 69 | 91.7% | 72 |
| Sensitivity LGD | 93.9% | 33 | 90.6% | 32 | 94.1% | 34 |
| Sensitivity HGD | 87.0% | 23 | 100.0% | 23 | 100.0% | 23 |
| Sensitivity dysplastic BE combined | 91.1% | 56 | 94.5% | 55 | 96.5% | 57 |
| Sensitivity Cancer | 90.7% | 97 | 94.9% | 99 | 96.0% | 100 |

Fig. 5

| | mVIM (Positive if > 1%) | | mSqBE18 (Positive if > 1%) | | Either mVIM or mSqBE18 Positive | |
|---|---|---|---|---|---|---|
| | % | # | % | # | % | # |
| Specificity Control GEJ (GERD, EE, other) | 89.5% | 38 | 100.0% | 38 | 89.5% | 38 |
| Sensitivity ND SSBE | 69.2% | 13 | 53.8% | 13 | 84.6% | 13 |
| Sensitivity ND LSBE | 88.9% | 18 | 83.3% | 18 | 94.4% | 18 |
| Sensitivity NDBE combined | 80.6% | 31 | 71.0% | 31 | 90.3% | 31 |
| Sensitivity LGD | 83.3% | 6 | 100.0% | 6 | 100.0% | 6 |
| Sensitivity HGD | 50.0% | 4 | 50.0% | 4 | 50.0% | 4 |
| Sensitivity dysplastic BE combined | 72.7% | 11 | 72.7% | 11 | 81.8% | 11 |
| Sensitivity Cancer | 87.5% | 8 | 75.0% | 8 | 87.5% | 8 |

Fig. 7

METHODS AND COMPOSITIONS FOR DETECTING ESOPHAGEAL NEOPLASIAS AND/OR METAPLASIAS IN THE ESOPHAGUS

CROSS-REFERENCE TO RELATED APPLICATIONS

This application is a United States National Stage filing under 35 U.S.C. § 371 of International Application No. PCT/US2017/040708, filed on Jul. 5, 2017 and claims priority to U.S. provisional application Ser. No. 62/358,701, filed on Jul. 6, 2016. The disclosures of the foregoing applications are hereby incorporated by reference in their entirety. International Application No. PCT/US2017/040708 was published under PCT Article 21 (2) in English.

FUNDING

This invention was made with government support under U01CA152756; U54CA163060; and P50CA150964 awarded by the National Institutes of Health (NIH). The government has certain rights in the invention.

SEQUENCE LISTING

The instant application contains a Sequence Listing which has been submitted via EFS-Web and is hereby incorporated by reference in its entirety. Said ASCII copy, created on Jan. 2, 2019, is named 1848493-0002-098-301_SL.TXT and is 14,247,811 bytes in size.

BACKGROUND

Over 15,000 new cases of esophageal cancer were diagnosed in 2010, and there were nearly as many deaths from this cancer alone. As with other cancers, this rate can be decreased by improved methods for diagnosis. Although methods for detecting esophageal cancer exist, the methods are not ideal. Generally, a combination of endoscopy, isolation of cells (for example, via collection of cells/tissues from a fluid sample or from a tissue sample), and/or imaging technologies are used to identify cancerous cells and tumors. While upper endoscopy, usually performed by a gastroenterologist, can detect neoplasias of the esophagus, as well as of the stomach and duodenum, it is an uncomfortable and expensive procedure. Other detection procedures, such as barium esophogography are also available, but are associated with false positives, false negatives, and cost and discomfort issues.

Because of the disadvantages of existing methods for detecting or treating esophageal neoplasias/cancers, new methods are needed for esophageal neoplasia/cancer diagnosis and therapy.

SUMMARY OF THE DISCLOSURE

In certain aspects, the present disclosure is based in part on the discovery of particular human genomic DNA regions (also referred to herein as informative loci or patches) in which the cytosines within CpG dinucleotides are differentially methylated in esophageal neoplasia compared to normal human tissues.

A first aspect of the present disclosure provides a method of diagnosing whether a subject has an esophageal neoplasia or metaplasia, comprising: obtaining a sample from a subject; measuring the amount of methylated cytosines in CpG dinucleotides in a vimentin nucleic acid sequence, or portion thereof, obtained from the sample; wherein if at least 80% of the cytosines in CpG dinucleotides in the vimentin nucleic acid sequence, or portion thereof, are methylated, than the vimentin nucleic acid sequence, or portion thereof, is considered a methylated read; and measuring the number of methylated reads present in the sample, wherein if at least 1% of the vimentin nucleic acid sequences, or portions thereof, in the sample are methylated reads, than the subject is determined to have an esophageal neoplasia or metaplasia.

In some embodiments, the vimentin nucleic acid sequences from the sample are treated with bisulfite. Optionally, the sequence of the bisulfite converted nucleic acid sequences is determined by next-generation sequencing. In some embodiments, the level of methylated cytosines is determined in an amplified portion of the vimentin nucleic acid sequence obtained from the subject. Optionally, between the amplification primers, the amplified portion comprises 10 dinucleotides that correspond to or are derived from 10 CpG dinucleotides present in the native non-bisulfite treated vimentin genomic sequence. In some embodiments, the primers used to amplify the portion of the vimentin nucleic acid sequence comprise SEQ ID NOs: 16209 and 16210. Optionally, the amplified portion comprises the nucleotide sequence of SEQ ID NOs: 16207 and/or 16208. In some embodiments, the 10 CpGs correspond to those that, after bisulfite treatment, are included in SEQ ID Nos: 16211 and 16212.

In some embodiments, if at least 1.05% of the vimentin nucleic acid sequences, or portions thereof, in the sample are methylated reads, than the subject is determined to have an esophageal neoplasia or metaplasia. Optionally, if at least 3% of the vimentin nucleic acid sequences, or portions thereof, in the sample are methylated reads, than the subject is determined to have an esophageal neoplasia or metaplasia. In some embodiments, if at least 5% of the vimentin nucleic acid sequences, or portions thereof, in the sample are methylated reads, than the subject is determined to have an esophageal neoplasia or metaplasia.

In some embodiments, if the subject is determined to have an esophageal neoplasia or metaplasia, then administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent.

A second aspect of the present disclosure provides a method of treating a subject having an esophageal neoplasia or metaplasia, wherein it has been previously determined that at least 1% of the vimentin nucleic acid sequences, or portions thereof, in a sample from the subject have at least 80% of the CpG dinucleotides methylated, wherein the method comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the therapeutic agent is a proton pump inhibitor, a Histamine H2 receptor blocking agents, an anti-reflux medication, a drug that moves food thru the gastrointestinal tract more quickly, carboplatin and paclitaxel (Taxol®) (which may be combined with radiation); cisplatin and 5-fluorouracil (5-FU) (often combined with radiation); ECF: epirubicine (Ellence®), cisplatin, and 5-FU (especially for gastroesophageal junction tumors); DCF: docetaxel (Taxotere®), cisplatin, and 5-FU; Cisplatin with capecitabine (Xelodat®): oxaliplatin and either 5-FU or capecitabine: doxorubicin (Adriamycin®), bleomycin, mitomycin, methotrexate, vinorelbine (Navelbine®), topotecan, and irinotecan (Camptosar®), trastuzumab, and/or ramucirumab. Optionally, the surgery is endoscopic mucosal resection (EMR), esophagectomy, and/or anti-reflux surgery.

In some embodiments, the disclosure provides for a method of diagnosing whether a subject has an esophageal neoplasia or metaplasia, comprising: obtaining a sample from a subject by means of a brushing (e.g., a cytology brushing); measuring the amount of methylated cytosines in CpG dinucleotides in an SqBE18 nucleic acid sequence, or portion thereof, obtained from the sample; wherein if at least 70% or at least 75% of the cytosines in CpG dinucleotides in the SqBE18 nucleic acid sequence, or portion thereof, are methylated, than the SqBE18 nucleic acid sequence, or portion thereof, is considered a methylated read; and measuring the number of methylated reads present in the sample: wherein if at least 3% of the SqBE18 nucleic acid sequences, or portions thereof, in the sample are methylated reads, than the subject is determined to have an esophageal neoplasia or metaplasia. In some embodiments, the SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the SqBE18 nucleic acid sequence obtained from the subject. In some embodiments, the amplified portion comprises 21 dinucleotides that correspond to or are derived from 21 CpG dinucleotides present in the native non-bisulfite treated SqBE18 genomic sequence. In some embodiments, if at least 3.11% of the SqBE18 nucleic acid sequences, or portions thereof, in the sample are methylated reads, than the subject is determined to have an esophageal neoplasia or metaplasia. In some embodiments, if the subject is determined to have an esophageal neoplasia or metaplasia, then the method further comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the disclosure provides for a method of treating a subject having an esophageal neoplasia or metaplasia, wherein it has been previously determined that at least 3% of the SqBE18 nucleic acid sequences, or portions thereof, in a brushing (e.g., a cytology brushing) sample from the subject have at least 70% or at least 75% of the CpG dinucleotides methylated, wherein the method comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent. In some embodiments, the therapeutic agent is a proton pump inhibitor, a Histamine H2 receptor blocking agents, an anti-reflux medication, a drug that moves food thru the gastrointestinal tract more quickly, carboplatin and paclitaxel (Taxol®) (which may be combined with radiation); cisplatin and 5-fluorouracil (5-FU) (often combined with radiation); ECF: epirubicine (Ellence®), cisplatin, and 5-FU (especially for gastroesophageal junction tumors); DCF: docetaxel (Taxotere®), cisplatin, and 5-FU; Cisplatin with capecitabine (Xeloda®); oxaliplatin and either 5-FU or capecitabine; doxorubicin (Adriamycin®), bleomycin, mitomycin, methotrexate, vinorelbine (Navelbine®), topotecan, and irinotecan (Camptosar®), trastuzumab, and/or ramucirumab. In some embodiments, the surgery is endoscopic mucosal resection (EMR), esophagectomy, and/or anti-reflux surgery. In some embodiments, the disclosure provides for a method of diagnosing whether a subject has an esophageal neoplasia or metaplasia, comprising: obtaining a sample from a subject by means of a balloon; measuring the amount of methylated cytosines in CpG dinucleotides in an SqBE18 nucleic acid sequence, or portion thereof, obtained from the sample; wherein if at least 70% or at least 75% of the cytosines in CpG dinucleotides in the SqBE18 nucleic acid sequence, or portion thereof, are methylated, than the SqBE18 nucleic acid sequence, or portion thereof, is considered a methylated read; and measuring the number of methylated reads present in the sample; wherein if at least 0.1% of the SqBE18 nucleic acid sequences, or portions thereof, in the sample are methylated reads, than the subject is determined to have an esophageal neoplasia or metaplasia. In some embodiments, the SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the SqBE18 nucleic acid sequence obtained from the subject. In some embodiments, the amplified portion comprises 21 dinucleotides that correspond to or are derived from 21 CpG dinucleotides present in the native non-bisulfite treated SqBE18 genomic sequence. In some embodiments, if at least 0.76% of the SqBE18 nucleic acid sequences, or portions thereof, in the sample are methylated reads, than the subject is determined to have an esophageal neoplasia or metaplasia. In some embodiments, if at least 1% of the SqBE18 nucleic acid sequences, or portions thereof, in the sample are methylated reads, than the subject is determined to have an esophageal neoplasia or metaplasia. In some embodiments, if the subject is determined to have an esophageal neoplasia or metaplasia, then the method further comprises administering to the subject cryotherpy, photodynamic therapy (PDT); radiofrequency ablation (RFA): laser ablation; argon plasma coagulation (APC); electrocoagulation (electrofulguration); esophageal stent, surgery, and/or a therapeutic agent.

In some embodiments, the disclosure provides for a method of treating a subject having an esophageal neoplasia or metaplasia, wherein it has been previously determined that at least 1% of the SqBE18 nucleic acid sequences, or portions thereof, in a balloon sample from the subject have at least 70% of the CpG dinucleotides methylated, wherein the method comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent. In some embodiments, the therapeutic agent is a proton pump inhibitor, a Histamine H2 receptor blocking agents, an anti-reflux medication, a drug that moves food thru the gastrointestinal tract more quickly, carboplatin and paclitaxel (Taxol®) (which may be combined with radiation); cisplatin and 5-fluorouracil (5-FU) (often combined with radiation); ECF: epirubicine (Ellence®), cisplatin, and 5-FU (especially for gastroesophageal junction tumors); DCF: docetaxel (Taxotere®), cisplatin, and 5-FU; Cisplatin with capecitabine (Xeloda®); oxaliplatin and either 5-FU or capecitabine; doxorubicin (Adriamycin®), bleomycin, mitomycin, methotrexate, vinorelbine (Navelbine®), topotecan, and irinotecan (Camptosar®), trastuzumab, and/or ramucirumab. In some embodiments, the surgery is endoscopic mucosal resection (EMR), esophagectomy, and/or anti-reflux surgery.

In some embodiments, the disclosure provides for a method of diagnosing whether a subject has an esophageal neoplasia or metaplasia, comprising: obtaining a sample from a subject by means of a brushing (e.g., a cytology brushing), measuring the amount of methylated cytosines in CpG dinucleotides in a vimentin nucleic acid sequence, or portion thereof, obtained from the sample: wherein if at least 80% of the cytosines in CpG dinucleotides in the vimentin nucleic acid sequence, or portion thereof, are methylated, than the vimentin nucleic acid sequence, or portion thereof, is considered a vimentin methylated read; measuring the amount of methylated cytosines in CpG dinucleotides in an SqBE18 nucleic acid sequence, or portion thereof, obtained from the sample; wherein if at least 70% or 75% of the cytosines in CpG dinucleotides in the SqBE18 nucleic acid sequence, or portion thereof, are methylated, than the SqBE18 nucleic acid sequence, or portion thereof, is considered an SqBE18 methylated read; and measuring the number of methylated reads present in the sample; wherein if at least 1% of the vimentin nucleic acid sequences, or portions thereof, in the sample are vimentin methylated reads, and wherein if at least 3% of the SqBE18 nucleic acid sequences, or portions thereof, in the sample are SqBE18 methylated reads, than the subject is determined to have an esophageal neoplasia or metaplasia. In some embodiments, the vimentin and SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the vimentin nucleic acid sequence and in an amplified portion of the SqBE18 nucleic acid sequence obtained from the subject. In some embodiments, the amplified portion of the SqBE18 nucleic acid sequence comprises 21 dinucleotides that correspond to or are derived from 21 CpG dinucleotides present in the native non-bisulfite treated SqBE18 genomic sequence. In some embodiments, the amplified portion of the vimentin nucleic acid sequence comprises 10 dinucleotides that correspond to or are derived from 10 CpG dinucleotides present in the native non-bisulfite treated vimentin genomic sequence. In some embodiments, if at least 1% of the vimentin nucleic acid sequences, or portions thereof, in the sample are vimentin methylated reads, wherein if at least 3.11% of the SqBE18 nucleic acid sequences, or portions thereof, in the sample are methylated reads, than the subject is determined to have an esophageal neoplasia or metaplasia. In some embodiments, if the subject is determined to have an esophageal neoplasia or metaplasia, then the method further comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the disclosure provides for a method of treating a subject having an esophageal neoplasia or metaplasia, wherein it has been previously determined that at least 1% of the vimentin nucleic acid sequences, or portions thereof, in a brushing (e.g., a cytology brushing) sample from the subject have at least 80% of the CpG dinucleotides methylated, wherein it has been previously determined that at least 3% of the SqBE18 nucleic acid sequences, or portions thereof, in a brushing (e.g., a cytology brushing) sample from the subject have at least 75% of the CpG dinucleotides methylated, and wherein the method comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent. In some embodiments, the therapeutic agent is a proton pump inhibitor, a Histamine H2 receptor blocking agents, an anti-reflux medication, a drug that moves food thru the gastrointestinal tract more quickly, carboplatin and paclitaxel (Taxol®) (which may be combined with radiation): cisplatin and 5-fluorouracil (5-FU) (often combined with radiation); ECF: epirubicine (Ellence®), cisplatin, and 5-FU (especially for gastroesophageal junction tumors); DCF: docetaxel (Taxotere®), cisplatin, and 5-FU; Cisplatin with capecitabine (Xeloda®); oxaliplatin and either 5-FU or capecitabine: doxorubicin (Adriamycin®), bleomycin, mitomycin, methotrexate, vinorelbine (Navelbine®), topotecan, and irinotecan (Camptosar®), trastuzumab, and/or ramucirumab. In some embodiments, the surgery is endoscopic mucosal resection (EMR), esophagectomy, and/or anti-reflux surgery. In some embodiments, method of diagnosing whether a subject has an esophageal neoplasia or metaplasia, comprising: obtaining a sample from a subject by means of a balloon; measuring the amount of methylated cytosines in CpG dinucleotides in a vimentin nucleic acid sequence, or portion thereof, obtained from the sample: wherein if at least 80% of the cytosines in CpG dinucleotides in the vimentin nucleic acid sequence, or portion thereof, are methylated, than the vimentin nucleic acid sequence, or portion thereof, is considered a vimentin methylated read; measuring the amount of methylated cytosines in CpG dinucleotides in an SqBE18 nucleic acid sequence, or portion thereof, obtained from the sample; wherein if at least 70% or at least 75% of the cytosines in CpG dinucleotides in the SqBE18 nucleic acid sequence, or portion thereof, are methylated, than the SqBE18 nucleic acid sequence, or portion thereof, is considered a SqBE18 methylated read; and measuring the number of methylated reads present in the sample; wherein if at least 0.95% of the vimentin nucleic acid sequences, or portions thereof, in the sample are vimentin methylated reads, and wherein if at least 0.1% of the SqBE18 nucleic acid sequences, or portions thereof, in the sample are SqBE18 methylated reads, than the subject is determined to have an esophageal neoplasia or metaplasia. In some embodiments, the vimentin and SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the vimentin nucleic acid sequence and in an amplified portion of the SqBE18 nucleic acid sequence obtained from the subject. In some embodiments, the amplified portion comprises 21 dinucleotides that correspond to or are derived from 21 CpG dinucleotides present in the native non-bisulfite treated SqBE18 genomic sequence. In some embodiments, the amplified portion of the vimentin nucleic acid sequence comprises 10 dinucleotides that correspond to or are derived from 10 CpG dinucleotides present in the native non-bisulfite treated vimentin genomic sequence. In some embodiments, if at least 1% of the vimentin nucleic acid sequences, or portions thereof and if at least 0.76% of the SqBE18 nucleic acid sequences, or portions thereof, in the sample are methylated reads, than the subject is determined to have an esophageal neoplasia or metaplasia. In some embodiments, if at least 1% of the vimentin nucleic acid sequences, or portions thereof and at least 1% of the SqBE18 nucleic acid sequences, or portions thereof, in the sample are methylated reads, than the subject is determined to have an esophageal neoplasia or metaplasia. In some embodiments, if the subject is determined to have an esophageal neoplasia or metaplasia, then the method further comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the disclosure provides for a method of treating a subject having an esophageal neoplasia or metaplasia, wherein it has been previously determined that at least 1% of the SqBE18 nucleic acid sequences, or portions thereof, in a balloon sample from the subject have at least 70% or at least 75% of the CpG dinucleotides methylated, wherein the method comprises administering to the subject cryotherpy, photodynamic therapy (PDT); radiofrequency ablation (RFA); laser ablation; argon plasma coagulation (APC); electrocoagulation (electrofulguration); esophageal stent, surgery, and/or a therapeutic agent. In some embodiments, the therapeutic agent is a proton pump inhibitor, a Histamine H2 receptor blocking agents, an anti-reflux medication, a drug that moves food thru the gastrointestinal tract more quickly, carboplatin and paclitaxel (Taxol®) (which may be combined with radiation): cisplatin and 5-fluorouracil (5-FU) (often combined with radiation); ECF: epirubicine (Ellence®), cisplatin, and 5-FU (especially for gastroesophageal junction tumors); DCF: docetaxel (Taxotere®), cisplatin, and 5-FU; Cisplatin with capecitabine (Xeloda®); oxaliplatin and either 5-FU or capecitabine; doxorubicin (Adriamycin®), bleomycin, mitomycin, methotrexate, vinorelbine (Navelbine®), topotecan, and irinotecan (Camptosar®), trastuzumab, and/or ramucirumab. In some embodiments, the surgery is endoscopic mucosal resection (EMR), esophagectomy, and/or anti-reflux surgery.

In some embodiments, the primers used to amplify the portion of the SqBe18 nucleic acid sequence in any of the methods disclosed herein comprise SEQ ID NOs: 8388 and/or 8402. In some embodiments, the amplified portion comprises the nucleotide sequence of SEQ ID NOs: 8318, 8360, 8332 and/or 8374. In some embodiments, the amplified portion comprises the nucleotide sequence of SEQ ID NOs: 8332 and/or 8374. In some embodiments, the determination that the subject has an esophageal neoplasia or metaplasia is confirmed by an additional diagnostic assay. In some embodiments, the additional diagnostic assay is an endoscopic assay.

BRIEF DESCRIPTION OF THE FIGURES

FIG. 1A shows a ROC curve based on Next-Generation Bisulfite Sequencing assay for SqBE18 m the training set of 61 controls and 108 cases. FIG. 1B shows a ROC curve based on Next-Generation Bisulfite Sequencing VIM assay in the training set of 59 controls and 107 cases. FIG. 1C shows a ROC curve based on Next-Generation Bisulfite Sequencing assay for SqBE18 in the validation set of 28 controls and 115 cases.

FIG. 2A shows a VIM Sensitivity and specificity curve. The 8+ CpG cutoff (blue box), maximizes the sum of specificity for controls and sensitivity for cases. FIG. 2B shows a SqBE18 Sensitivity and specificity curve. The 15+, 16+, and 17+ CpG cutoffs offer identical maximum sensitivity+specificity sum for SqBE18. 16+ CpGs (blue box), was chosen as the middle of this range.

FIG. 3 is a table showing the performance of VIM and SqBE18 in a training set of brushings. Specificity Controls of the Gastroesophageal Junction (GEJ)=Unaffected controls (individuals with GERD, erosive esophagitis (EE), or no pathology detected during endoscopy ("other"): SSBE=short-segment Barrett's Esophagus (1 to 3 cm)): LSBE=Barrett's Esophagus (3 cm or more); LOD=Barret's Esophagus with Low-Grade Dysplasia; HGD=Barrett's Esophagus with High-Grade Dysplasia: Cancer=includes EAC (Esophageal adenocarcinoma) and JCA (Junctional cancer of the esophagus).

FIG. 4 is a table showing the performance of VIM and SqBE18 in VALIDATION set of bushings Specificity Controls of the Gastroesophageal Junction (GEJ)=Unaffected controls (individuals with GERD, erosive esophagitis (EE), or no pathology detected during endoscopy ("other")): SSBE=short-segment Barrett's Esophagus (1 to 3 cm)): LSBE=Barrett's Esophagus (3 cm or more); LOD=Barret's Esophagus with Low-Grade Dysplasia; HGD=Barrett's Esophagus with—High-Grade Dysplasia; Cancer=includes EAC (Esophageal adenocarcinoma) and JCA (Junctional cancer of the esophagus).

FIG. 5 is a table showing the performance of VIM and SqBE18 in a combination set of brushings. This table includes all the samples from training and validation set of brushings combined. Specificity Controls of the Gastroesophageal Junction (GEJ)===Unaffected controls (individuals with GERD, erosive esophagitis (EE), or no pathology detected during endoscopy ("other")): SSBE=short-segment Barrett's Esophagus (1 to 3 cm)): LSBE=Barrett's Esophagus (3 cm or more). LGD==Barret's Esophagus with Low-Grade Dysplasia; HGD=Barrett's Esophagus with High-Grade Dysplasia: Cancer=includes EAC (Esophageal adenocarcinoma) and JCA (Junctional cancer of the esophagus).

FIG. 6A shows a ROC curve based on Next-Generation Bisulfite Sequencing assay for VIM in the training set of 38 controls and 50 cases. FIG. 6B shows a ROC curve based on Next-Generation Bisulfite Sequencing SqBE18 assay in the training set of 38 controls and 50 cases. Area under the curve (AUC), and the sensitivity and specificity of the assay at the optimal cutpoint are listed for each graph.

FIG. 7 is a table showing performance of VIM and SqBE18 in Esophageal balloon samples. Specificity Controls of the Gastroesophageal Junction (GEJ)=Unaffected controls (individuals with GERD, erosive esophagitis (EE), or no pathology detected during endoscopy ("other")); SSBE===short-segment Barrett's Esophagus (1 to 3 cm)): LSBE==Barrett's Esophagus (3 cm or more): LGD=Barret's Esophagus with Low-Grade Dysplasia; HGD==Barrett's Esophagus with High-Grade Dysplasia; Cancer=: includes EAC (Esophageal adenocarcinoma) and JCA (Junctional cancer of the esophagus).

DETAILED DESCRIPTION OF THE INVENTION

I. Definitions

Figure 1A:
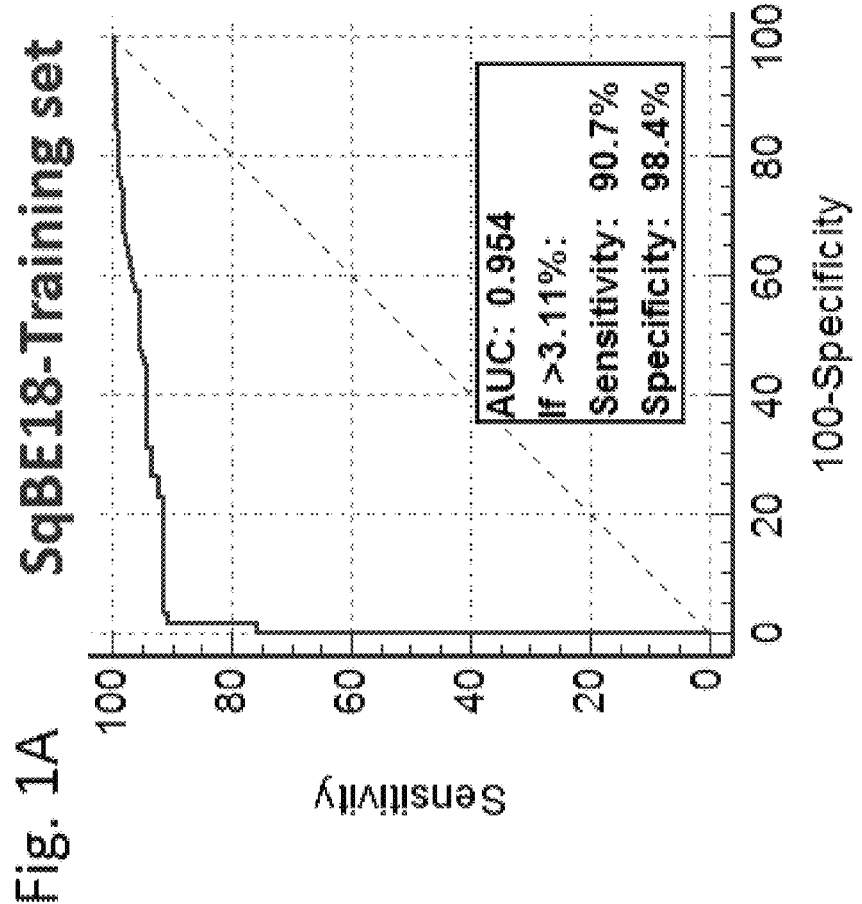
FIGS. 1A-ID show the Receiver Operating Characteristic (ROC) curves of methylated vimentin (VIM) and SqBE18 measurement in esophageal cytology brushings of the normal appearing GE junction or of endoscopically visualized BE or EAC.

For convenience, certain terms employed in the specification, examples, and appended claims are collected here. Unless defined otherwise, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Each embodiment of the invention described herein may be taken alone or in combination with one or more other embodiments of the invention.

Throughout this specification, the word "comprise" or variations such as "comprises" or "comprising" will be understood to imply the inclusion of a stated integer or groups of integers but not the exclusion of any other integer or group of integers.

The articles "a" and "an" are used herein to refer to one or to more than one (i.e., to at least one) of the grammatical object of the article. By way of example, "an element" means one element or more than one element.

The terms "adenoma" is used herein to describe any precancerous neoplasia or benign tumor of epithelial tissue, for example, a precancerous neoplasia of the gastrointestinal tract, pancreas, and/or the bladder.

The term "blood-derived fraction" herein refers to a component or components of whole blood. Whole blood comprises a liquid portion (i.e., plasma) and a solid portion (i.e., blood cells). The liquid and solid portions of blood are each comprised of multiple components, e.g., different proteins in plasma or different cell types in the solid portion. One of these components or a mixture of any of these components is a blood-derived fraction as long as such fraction is missing one or more components found in whole blood.

The term "esphophagus" is intended to encompass the upper portion of the digestive system spanning from the back of the oral cavity, passing downwards through the rear part of the mediastinum, through the diaphragm and into the stomach.

The term "esophageal cancer" is used herein to refer to any cancerous neoplasia of the esophagus.

"Barrett's esophagus" as used herein refers to an abnormal change (metaplasia) in the cells of the lower portion of the esophagus. Barrett's is characterized the finding of intestinal metaplasia in the esophagus.

A "brushing" of the esophagus, as referred to herein, may be obtained using any of the means known in the art. In some embodiments, a brushing is obtained by contacting the esophagus with a brush, a cytology brush, a sponge, a balloon, or with any other device or substance that contacts the esophagus and obtains an esophageal sample.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "compound", "test compound," "agent", and "molecule" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term "compound-converted DNA" herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term "de-methylating agent" as used herein refers agents that restore activity and/or gene expression of target genes silenced by methylation upon treatment with the agent. Examples of such agents include without limitation 5-azacytidine and 5-aza-2'-deoxycytidine.

The term "detection" is used herein to refer to any process of observing a marker, or a change in a marker (such as for example the change in the methylation state of the marker), in a biological sample, whether or not the marker or the change in the marker is actually detected. In other words, the act of probing a sample for a marker or a change in the marker, is a "detection" even if the marker is determined to be not present or below the level of sensitivity. Detection may be a quantitative, semi-quantitative or non-quantitative observation.

The term "differentially methylated nucleotide sequence" refers to a region of a genomic loci that is found to be methylated in a in cancer tissues or cell lines, but not methylated in the normal tissues or cell lines.

The term "neoplasia" as used herein refers to an abnormal growth of tissue. As used herein, the term "neoplasia" may be used to refer to cancerous and non-cancerous tumors, as well as to Barrett's esophagus (which may also be referred to herein as a metaplasia) and Barrett's esophagus with dysplasia. In some embodiments, the Barrett's esophagus with dysplasia is Barrett's esophagus with high grade dysplasia. In some embodiments, the Barrett's esophagus with dysplasia is Barrett's esophagus with low grade dysplasia. In some embodiments, the neoplasia is a cancer (e.g., esophageal adenocarcinoma).

"Gastrointestinal neoplasia" refers to neoplasia of the upper and lower gastrointestinal tract. As commonly understood in the art, the upper gastrointestinal tract includes the esophagus, stomach, and duodenum; the lower gastrointestinal tract includes the remainder of the small intestine and all of the large intestine.

The terms "healthy", "normal," and "non-neoplastic" are used interchangeably herein to refer to a subject or particular cell or tissue that is devoid (at least to the limit of detection) of a disease condition, such as a neoplasia.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position: when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated or "non-homologous" shares, in some embodiments, less than 40% identity, and in particular embodiments, less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and BLAST) can be used. See www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (*Computational Molecular Biology*, Lesk, A. M., ed., Oxford University Press. New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M, and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990)). The well known Smith Waterman algorithm may also be used to determine identity.

The term "including" is used herein to mean, and is used interchangeably with, the phrase "including but not limited to."

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The term "methylation-specific PCR" ("MSP") herein refers to a polymerase chain reaction in which amplification of the compound-converted template sequence is performed. Two sets of primers are designed for use in MSP. Each set of primers comprises a forward primer and a reverse primer. One set of primers, called methylation-specific primers (see below), will amplify the compound-converted template sequence if C bases in CpG dinucleotides within the DNA are methylated. Another set of primers, called unmethylation-specific primers or primers for unmethylated sequences and the like (see below), will amplify the compound-converted template sequences if C bases in CpG dinucleotides within the DNA are not methylated.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "proteins" and "polypeptides" are used interchangeably herein.

A "sample" includes any material that is obtained or prepared for detection of a molecular marker or a change in a molecular marker such as for example the methylation state, or any material that is contacted with a detection reagent or detection device for the purpose of detecting a molecular marker or a change in the molecular marker.

As used herein. "obtaining a sample" includes directly retrieving a sample from a subject to be assayed, or directly retrieving a sample from a subject to be stored and assayed at a later time. Alternatively, a sample may be obtained via a second party. That is, a sample may be obtained via, e.g., shipment, from another individual who has retrieved the sample, or otherwise obtained the sample.

A "subject" is any organism of interest, generally a mammalian subject, such as a mouse, and in particular embodiments, a human subject.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target sequence, or a sequence complementary thereto, or naturally occurring mutants thereof, such that it has, in some embodiments, less than 15%, less than 10%, or less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As applied to polypeptides, the term "substantial sequence identity" means that two peptide sequences, when optimally aligned such as by the programs GAP or BESTFIT using default gap, share at least 90 percent sequence identity, in some embodiments, at least 95 percent sequence identity, or at least 99 percent sequence identity or more. In some embodiments, residue positions which are not identical differ by conservative amino acid substitutions. For example, the substitution of amino acids having similar chemical properties such as charge or polarity is not likely to affect the properties of a protein. Examples include glutamine for asparagine or glutamic acid for aspartic acid.

An "informative loci" as used herein, refers to any of the nucleic acid sequences disclosed herein that may have altered (e.g., increased) methylation in a sample (e.g., an esophageal tissue sample) from a subject having Barrett's esophagus and/or an esophageal neoplasia as compared to the methylation patterns of the corresponding nucleic acid sequence in a sample from a healthy control subject. An example of an informative loci is vimentin.

The term "Up3" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12563, 12581, 12599, 12617, or fragments or reverse complements thereof. In some embodiments, the Up3 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12569, 12587, 12605 or 12623, or fragments or reverse complements thereof. In some embodiments, the Up3 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12575, 12593, 12611 or 12629, or fragments or reverse complements thereof. In some embodiments, the Up3 sequence may be amplified using primers comprising the sequence of SEQ ID NOs: 12635 and/or 12641, or fragments or reverse complements thereof.

The term "Up10" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12564, 12582, 12600 or 12618, or fragments or reverse complements thereof. In some embodiments, the Up10 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12570, 12588, 12606 or 12624, or fragments or reverse complements thereof. In some embodiments, the Up10 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12576, 12594, 12612 or 12630, or fragments or reverse complements thereof. In some embodiments, the Up10 sequence may be amplified using primers comprising the sequence of SEQ ID NOs: 12636 and/or 12642, or fragments or reverse complements thereof.

The term "Up15-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12565, 12583, 12601 or 12619, or fragments or reverse complements thereof. In some embodiments, the Up15-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12571, 12589, 12607 or 12625, or fragments or reverse complements thereof. In some embodiments, the Up15-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12577, 12595, 12613 or 12631, or fragments or reverse complements thereof. In some embodiments, the Up15-1 sequence may be amplified using primers comprising the sequence of SEQ ID NOs: 12637 and/or 12643, or fragments or reverse complements thereof.

The term "Up15-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12565, 12583, 12647 or 12656, or fragments or reverse complements thereof. In some embodiments, the Up15-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12571, 12589, 12650 or 12659, or fragments or reverse complements thereof. In some embodiments, the Up15-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12577, 12595, 12653 or 12662, or fragments or reverse complements thereof. In some embodiments, the Up15-2 sequence may be amplified using primers comprising the sequence of SEQ ID NOs: 12665 and/or 12668, or fragments or reverse complements thereof.

The term "Up20-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12566, 12584, 12602 or 12620, or fragments or reverse complements thereof. In some embodiments, the Up20-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12572, 12590, 12608 or 12626, or fragments or reverse complements thereof. In some embodiments, the Up20-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12578, 12596, 12614 or 12632, or fragments or reverse complements thereof. In some embodiments, the Up20-1 sequence may be amplified using primers comprising the sequence of SEQ ID NOs: 12638 and/or 12644, or fragments or reverse complements thereof.

The term "Up20-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12566, 12584, 12648 or 12657, or fragments or reverse complements thereof. In some embodiments, the Up20-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12572, 12590, 12651 or 12660, or fragments or reverse complements thereof. In some embodiments, the Up20-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12578, 12596, 12654 or 12663, or fragments or reverse complements thereof. In some embodiments, the Up20-2 sequence may be amplified using primers comprising the sequence of SEQ ID NOs: 12666 and/or 12669, or fragments or reverse complements thereof.

The term "Up27" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12567, 12585, 12603 or 12621, or fragments or reverse complements thereof. In some embodiments, the Up27 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12573, 12591, 12609 or 12627, or fragments or reverse complements thereof. In some embodiments, the Up27 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12579, 12597, 12615 or 12633, or fragments or reverse complements thereof. In some embodiments, the Up27 sequence may be amplified using primers comprising the sequence of SEQ ID NOs: 12639 and/or 12645, or fragments or reverse complements thereof.

The term "Up35-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12568, 12586, 12604 or 12622, or fragments or reverse complements thereof. In some embodiments, the Up35-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12574, 12592, 12610 or 12628, or fragments or reverse complements thereof. In some embodiments, the Up35-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12580, 12598, 12616 or 12634, or fragments or reverse complements thereof. In some embodiments, the Up35-1 sequence may be amplified using primers comprising the sequence of SEQ ID NOs: 12640 and/or 12646, or fragments or reverse complements thereof.

The term "Up35-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 12568, 12586, 12649 or 12658, or fragments or reverse complements thereof. In some embodiments, the Up35-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 12574, 12592, 12652 or 12661, or fragments or reverse complements thereof. In some embodiments, the Up35-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 12580, 12598, 12655 or 12664, or fragments or reverse complements thereof. In some embodiments, the Up35-2 sequence may be amplified using primers comprising the sequence of SEQ ID NOs: 12667 and/or 12670, or fragments or reverse complements thereof.

The term "SqBE 2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8209, 8251, 8293 or 8335, or fragments or reverse complements thereof. In some embodiments, the SqBE 2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8223, 8265, 8307 or 8349, or fragments or reverse complements thereof. In some embodiments, the SqBE 2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8237, 8279, 8321 or 8363, or fragments or reverse complements thereof. In some embodiments, the SqBE 2 sequence may be amplified using primers comprising the sequence of SEQ ID NOs: 8377 and/or 8391, or fragments or reverse complements thereof.

The term "SqBE 5" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8210, 8252, 8294 or 8336, or fragments or reverse complements thereof. In some embodiments, the SqBE 5 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8224, 8266, 8308 or 8350, or fragments or reverse complements thereof. In some embodiments, the SqBE 5 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8238, 8280, 8322 or 8364, or fragments or reverse complements thereof. In some embodiments, the SqBE 5 sequence may be amplified using primers comprising the sequence of SEQ ID NOs: 8378 and/or 8392, or fragments or reverse complements thereof.

The term "SqBE 7" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8211, 8253, 8295 or 8337, or fragments or reverse complements thereof. In some embodiments, the SqBE 7 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8225, 8267, 8309 or 8351, or fragments or reverse complements thereof. In some embodiments, the SqBE 7 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8239, 8281, 8323 or 8365, or fragments or reverse complements thereof. In some embodiments, the SqBE 7 sequence may be amplified using primers comprising the sequence of SEQ ID NOs: 8379 and/or 8393, or fragments or reverse complements thereof.

The term "SqBE 9" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8212, 8254, 8296 or 8338, or fragments or reverse complements thereof. In some embodiments, the SqBE 9 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8226, 8268, 8310 or 8352, or fragments or reverse complements thereof. In some embodiments, the SqBE 9 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8240, 8282, 8324 or 8366, or fragments or reverse complements thereof. In some embodiments, the SqBE 9 sequence may be amplified using primers comprising the sequence of SEQ ID NOs: 8380 and/or 8394, or fragments or reverse complements thereof.

The term "SqBE 10" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8213, 8255, 8297 or 8339, or fragments or reverse complements thereof. In some embodiments, the SqBE 10 sequence refers to a bisulfite converted nucleotide sequence comprising a sequence at least 80%, 85%°, 90%, 91%, 92%, 93%, 94%, 95%, 96%, 97%, 98%, 99% or 100% identity to the sequence of SEQ ID NO: 8227, 8269, 8311 or 8353, or fragments or reverse complements thereof. In some embodiments, the SqBE 10 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8241, 8283, 8325 or 8367, or fragments or reverse complements thereof. In some embodiments, the SqBE 10 sequence may be amplified using primers comprising the sequence of SEQ ID NOs: 8381 and/or 8395, or fragments or reverse complements thereof.

The term "SqBE 11-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8214, 8256, 8298 or 8340, or fragments or reverse complements thereof. In some embodiments, the SqBE 11-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8228, 8270, 8312 or 8354, or fragments or reverse complements thereof. In some embodiments, the SqBE 11-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8242, 8284, 8326 or 8368, or fragments or reverse complements thereof. In some embodiments, the SqBE 11-1 sequence may be amplified using primers comprising the sequence of SEQ ID NOs: 8382 and/or 8396, or fragments or reverse complements thereof.

The term "SqBE 11-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8214, 8256, 8405 or 8420, or fragments or reverse complements thereof. In some embodiments, the SqBE 11-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8228, 8270, 8410 or 8425, or fragments or reverse complements thereof. In some embodiments, the SqBE 11-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8242, 8284, 8415 or 8430, or fragments or reverse complements thereof. In some embodiments, the SqBE 11-2 sequence may be amplified using primers comprising the sequence of SEQ ID NOs: 8435 and/or 8440, or fragments or reverse complements thereof.

The term "SqBE 13" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8215, 8257, 8299 or 8341, or fragments or reverse complements thereof. In some embodiments, the SqBE 13 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8229, 8271, 8313 or 8355, or fragments or reverse complements thereof. In some embodiments, the SqBE 13 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8243, 8285, 8327 or 8369, or fragments or reverse complements thereof. In some embodiments, the SqBE 13 sequence may be amplified using primers comprising the sequence of SEQ ID NOs: 8383 and/or 8397, or fragments or reverse complements thereof.

The term "SqBE 14-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8216, 8258, 8406 or 8421, or fragments or reverse complements thereof. In some embodiments, the SqBE 14-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8230, 8272, 8411 or 8426, or fragments or reverse complements thereof. In some embodiments, the SqBE 14-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8244, 8286, 8416 or 8431, or fragments or reverse complements thereof. In some embodiments, the SqBE 14-2 sequence may be amplified using primers comprising the sequence of SEQ ID NOs: 8436 and/or 8441, or fragments or reverse complements thereof.

The term "SqBE 15" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8217, 8259, 8301 or 8343, or fragments or reverse complements thereof. In some embodiments, the SqBE 15 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8231, 8273, 8315 or 8357, or fragments or reverse complements thereof. In some embodiments, the SqBE 15 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8245, 8287, 8329 or 8371, or fragments or reverse complements thereof. In some embodiments, the SqBE 15 sequence may be amplified using primers comprising the sequence of SEQ ID NOs: 8385 and/or 8399, or fragments or reverse complements thereof.

The term "SqBE 16-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8218, 8260, 8302 or 8344, or fragments or reverse complements thereof. In some embodiments, the SqBE 16-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8232, 8274, 8316 or 8358, or fragments or reverse complements thereof. In some embodiments, the SqBE 16-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8246, 8288, 8330 or 8372, or fragments or reverse complements thereof. In some embodiments, the SqBE 16-1 sequence may be amplified using primers comprising the sequence of SEQ ID NOs: 8386 and/or 8400, or fragments or reverse complements thereof.

The term "SqBE 16-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8218, 8260, 8407 or 8422, or fragments or reverse complements thereof. In some embodiments, the SqBE 16-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8232, 8274, 8412 or 8427, or fragments or reverse complements thereof. In some embodiments, the SqBE 16-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8246, 8288, 8417 or 8432, or fragments or reverse complements thereof. In some embodiments, the SqBE 16-2 sequence may be amplified using primers comprising the sequence of SEQ ID NOs: 8437 and/or 8442, or fragments or reverse complements thereof.

The term "SqBE 17-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8219, 8261, 8303 or 8345, or fragments or reverse complements thereof. In some embodiments, the SqBE 17-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8233, 8275, 8317 or 8359, or fragments or reverse complements thereof. In some embodiments, the SqBE 17-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8247, 8289, 8331 or 8373, or fragments or reverse complements thereof. In some embodiments, the SqBE 17-1 sequence may be amplified using primers comprising the sequence of SEQ ID NOs: 8387 and/or 8401, or fragments or reverse complements thereof.

The term "SqBE18" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8220, 8262, 8304 or 8346, or fragments or reverse complements thereof. In some embodiments, the SqBE18 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8234, 8276, 8318 or 8360, or fragments or reverse complements thereof. In some embodiments, the SqBE18 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8248, 8290, 8332 or 8374, or fragments or reverse complements thereof. In some embodiments, the SqBE18 sequence may be amplified using primers comprising the sequence of SEQ ID NOs: 8388 and/or 8402, or fragments or reverse complements thereof.

The term "SqBE 22-1" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8221, 8263, 8305 or 8347, or fragments or reverse complements thereof. In some embodiments, the SqBE 22-1 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8235, 8277, 8319 or 8361, or fragments or reverse complements thereof. In some embodiments, the SqBE 22-1 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8249, 8291, 8333 or 8375, or fragments or reverse complements thereof. In some embodiments, the SqBE 22-1 sequence may be amplified using primers comprising the sequence of SEQ ID NOs: 8389 and/or 8403, or fragments or reverse complements thereof.

The term "SqBE 22-2" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8221, 8263, 8409 or 8424, or fragments or reverse complements thereof. In some embodiments, the SqBE 22-2 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8235, 8277, 8414 or 8429, or fragments or reverse complements thereof. In some embodiments, the SqBE 22-2 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8249, 8291, 8419 or 8434, or fragments or reverse complements thereof. In some embodiments, the SqBE 22-2 sequence may be amplified using primers comprising the sequence of SEQ ID NOs: 8439 and/or 8444, or fragments or reverse complements thereof.

The term "SqBE 23" as used herein refers to a nucleotide sequence comprising a sequence at least 80%, 85%, 90%, 91%, 92%, 93%, 94%, 95%, 96%, 97%, 98%, 99% or 100% identity to the sequence of SEQ ID NO: 8222, 8264, 8306 or 8348, or fragments or reverse complements thereof. In some embodiments, the SqBE 23 sequence refers to a bisulfite converted nucleotide sequence comprising a sequence at least 80%, 85%, 90%, 91%, 92%, 93%, 94%, 95%, 96%, 97%, 98%, 99% or 100% identity to the sequence of SEQ ID NO: 8236, 8278, 8320 or 8362, or fragments or reverse complements thereof. In some embodiments, the SqBE 23 sequence refers to a bisulfite converted product of a methylated nucleotide sequence comprising a sequence at least 80%, 85%, 90%, 91%, 92%, 93%, 94%, 95%, 96%, 97%, 98%, 99% or 100% identity to the sequence of SEQ ID NO: 8250, 8292, 8334 or 8376, or fragments or reverse complements thereof. In some embodiments, the SqBE 23 sequence may be amplified using primers comprising the sequence of SEQ ID NOs: 8390 and/or 8404, or fragments or reverse complements thereof.

In some instances, any of the nucleotide sequences disclosed herein contain one or more "Y" positions. Cytosine residues that may be methylated or unmethylated, and hence may be bisulfite converted to T (if unmethylated) or remain as a C (if methylated), are designated with a "Y." In some embodiments, a parental nucleotide sequence is fully unmethylated if the sequence comprises a T at every Y position following bisulfite conversion. In some embodiments, a parental nucleotide sequence is fully methylated if the sequence comprises a C at every Y position following bisulfite conversion. In some embodiments, a parental nucleotide sequence is partially methylated if the sequence comprises at least one C at a Y position and at least one T at a Y position of the sequence following bisulfite conversion. In some embodiments, the bisulfite converted sequences disclosed herein comprise at least one C at a Y position and at least one T at a Y position, i.e., the parental sequence is partially methylated.

II. Overview

This disclosure is based at least in part on the recognition that differential methylation of particular genomic loci (e.g., vimentin and/or SqBE18) may be indicative of a neoplasia or metaplasia of the upper gastrointestinal tract. e.g., esophagus. The present findings demonstrate that methylation at these genomic loci may be a useful biomarker of neoplasia in the upper gastrointestinal tract. The present findings further demonstrate that the status of methylation at these genomic loci used in combination with the status of somatic mutation(s) in TP53 may be a highly sensitive and specific biomarker of neoplasia in the upper gastrointestinal tract.

In general, neoplasias may develop through one of at least three different pathways, termed chromosomal instability, microsatellite instability, and the CpG island methylator phenotype (CIMP). Although there is some overlap, these pathways tend to present somewhat different biological behavior. By understanding the pathway of tumor development, the target genes involved, and the mechanisms underlying the genetic instability, it is possible to implement strategies to detect and treat the different types of neoplasias.

This disclosure is based, at least in part, on the recognition that certain target genes may be silenced or inactivated by the differential methylation of CpG islands in the 5' flanking or promoter regions of the target gene. CpG islands are clusters of cytosine-guanosine residues in a DNA sequence, which are prominently represented in the 5-flanking region or promoter region of about half the genes in our genome. In particular, this application is based at least in part on the recognition that differential methylation of particular genomic loci may be indicative of neoplasia of the upper gastrointestinal tract including, but not limited to, esophageal neoplasia.

Additionally, this disclosure is based, at least in part, on the recognition that somatic mutations in TP53 (e.g., any of the somatic TP53 mutations disclosed herein), in combination with methylation of certain informative loci as disclosed herein, may serve as useful indicators of neoplasia, including esophageal neoplasia (e.g., esophageal adenocarcinoma). In certain embodiments, the TP53 somatic mutation is any of the TP53 mutations disclosed herein. In certain embodiments, the TP53 somatic mutation is any nonsynonymous somatic mutation known in the art. In certain embodiments, the TP53 somatic mutation is any one or more mutation at any one or more amino acid residue corresponding to amino acid residue 72, 105, 108, 110, 113, 124, 127, 132, 144, 152, 163, 175, 183, 194, 213, 214, 218, 232, 234, 248, 265, 273, 278, 306, 337, 347, or 639 of SEQ ID NO: 16205. In certain embodiments, the TP53 somatic mutation is any one or more mutation selected from the group consisting of: Leu194Arg. Gly105Asp, Arg273His, Tyr163His, Ile232Thr, Arg213Ter. Arg273His, Arg248Gln, Arg175His, Arg110delinsGlnSer, Ser183Ter, Arg248Gln, Arg337Leu, Lys132Arg, Leu265ThrfsTer7. Arg306Ter, Cys124TrpfsTer25, Pro72Arg. Val218Glu, His214Leu, Gln144Ter, Phe113Ser, Tyr234His. Ser127Phe, Pro278Ala, Ala347Thr, and Pro152Leu of SEQ ID NO: 16205. In certain embodiments, the TP53 mutation is any one or more mutation at any one or more nucleotide position corresponding to nucleotide position 108, 215, 314, 338, 380, 395, 430, 455, 487, 524, 548, 581, 637, 639, 641, 653, 695, 700, 743, 818, 832, 916, 1010, or 1039 of SEQ ID NO: 16206.

The sequence of SEQ ID NO: 16205 (corresponding to GenBank Accession No. NP_000537.3) is as follows:

```
MEEPQSDPSVEPPLSQETFSDLWKLLPENNVLSPLPSQAMDDLMLSPD
DIEQWFTEDPGPDEAPRMPEAAPPVAPAPAAPTPAAPAPAPSWPLSSS
VPSQKTYQGSYGFRLGFLHSGTAKSVTCTYSPALNKMFCQLAKTCPVQ
LWVDSTPPPGTRVRAMAIYKQSQHMTEVVRRCPHHERCSDSDGLAPPQ
HLIRVEGNLRVEYLDDRNTFRHSVVVPYEPPEVGSDCTTIHYNYMCNS
SCMGGMNRRPILTIITLEDSSGNLLGRNSFEVRVCACPGRDRRTEEEN
LRKKGEPHHELPPGSTKRALPNNTSSSPQPKKKPLDGEYFTLQIRGRE
RFEMFRELNEALELKDAQAGKEPGGSRAHSSHLKSKKGQSTSRHKKLM
FKTEGPDSD
```

The sequence of SEQ ID NO: 16206 (corresponding to GenBank Accession No. NM_000546.5) is as follows:

```
GATGGGATTGGGGTTTTCCCCTCCCATGTGCTCAAGACTGGCGCTAA
AAGTTTTGAGCTTCTCAAAAGTCTAGAGCCACCGTCCAGGGAGCAGG
TAGCTGCTGGGCTCCGGGGACACTTTGCGTTCGGGCTGGGAGCGTGC
TTTCCACGACGGTGACACGCTTCCCTGGATTGGCAGCCAGACTGCCT
TCCGGGTCACTGCCATGGAGGAGCCGCAGTCAGATCCTAGCGTCGAG
CCCCCTCTGAGTCAGGAAACATTTTCAGACCTATGGAAACTACTTCC
TGAAAACAACGTTCTGTCCCCCTTGCCGTCCCAAGCAATGGATGATT
```

-continued
```
TGATGCTGTCCCCGGACGATATTGAACAATGGTTCACTGAAGACCCA

GGTCCAGATGAAGCTCCCAGAATGCCAGAGGCTGCTCCCCCCGTGGC

CCCTGCACCAGCAGCTCCTACACCGGCGGCCCCTGCACCAGCCCCCT

CCTGGCCCCTGTCATCTTCTGTCCCTTCCCAGAAAACCTACCAGGGC

AGCTACGGTTTCCGTCTGGGCTTCTTGCATTCTGGGACAGCCAAGTC

TGTGACTTGCACGTACTCCCCTGCCCTCAACAAGATGTTTTGCCAAC

TGGCCAAGACCTGCCCTGTGCAGCTGTGGGTTGATTCCACACCCCG

CCCGGCACCCGCGTCCGCGCCATGGCCATCTACAAGCAGTCACAGCA

CATGACGGAGGTTGTGAGGCGCTGCCCCCACCATGAGCGCTGCTCAG

ATAGCGATGGTCTGGCCCCTCCTCAGCATCTTATCCGAGTGGAAGGA

AATTTGCGTGTGGAGTATTTGGATGACAGAAACACTTTTCGACATAG

TGTGGTGGTGCCCTATGAGCCGCCTGAGGTTGGCTCTGACTGTACCA

CCATCCACTACAACTACATGTGTAACAGTTCCTGCATGGGCGGCATG

AACCGGAGGCCCATCCTCACCATCATCACACTGGAAGACTCCAGTGG

TAATCTACTGGGACGGAACAGCTTTGAGGTGCGTGTTTGTGCCTGTC

CTGGGAGAGACCGGCGCACAGAGGAAGAGAATCTCCGCAAGAAAGGG

GAGCCTCACCACGAGCTGCCCCCAGGGAGCACTAAGCGAGCACTGCC

CAACAACACCAGCTCCTCTCCCCAGCCAAAGAAGAAACCACTGGATG

GAGAATATTTCACCCTTCAGATCCGTGGGCGTGAGCGCTTCGAGATG

TTCCGAGAGCTGAATGAGGCCTTGGAACTCAAGGATGCCCAGGCTGG

GAAGGAGCCAGGGGGAGCAGGGCTCACTCCAGCCACCTGAAGTCCA

AAAAGGGTCAGTCTACCTCCCGCCATAAAAAACTCATGTTCAAGACA

GAAGGGCCTGACTCAGACTGACATTCTCCACTTCTTGTTCCCCACTG

ACAGCCTCCCACCCCCATCTCTCCCTCCCCTGCCATTTTGGGTTTTG

GGTCTTTGAACCCTTGCTTGCAATAGGTGTGCGTCAGAAGCACCCAG

GACTTCCATTTGCTTTGTCCCGGGGCTCCACTGAACAAGTTGGCCTG

CACTGGTGTTTTGTTGTGGGGAGGAGGATGGGGAGTAGGACATACCA

GCTTAGATTTTAAGGTTTTTACTGTGAGGGATGTTTGGGAGATGTAA

GAAATGTTCTTGCAGTTAAGGGTTAGTTTACAATCAGCCACATTCTA

GGTAGGGCCCACTTCACCGTACTAACCAGGGAAGCTGTCCCTCACT

GTTGAATTTTCTCTAACTTCAAGGCCCATATCTGTGAAATGCTGGCA

TTTGCACCTACCTCACAGAGTGCATTGTGAGGGTTAATGAAATAATG

TACATCTGGCCTTGAAACCACCTTTTATTACATGGGTCTAGAACTT

GACCCCCTTGAGGGTGCTTGTCCCTCTCCCTGTTGGTCGGTGGGTT

GGTAGTTTCTACAGTTGGGCAGCTGGTTAGGTAGAGGGAGTTGTCAA

GTCTCTGCTGGCCCAGCCAAACCCTGTCTGACAACCTCTTGGTGAAC

CTTAGTACCTAAAAGGAAATCTCACCCCATCCCACACCCTGGAGGAT

TTCATCTCTTGTATATGATGATCTGGATCCACCAAGACTTGTTTTAT

GCTCAGGGTCAATTTCTTTTTTCTTTTTTTTTTTTTTTTCTTTTT

CTTTGAGACTGGGTCTCGCTTTGTTGCCCAGGCTGGAGTGGAGTGGC

GTGATCTTGGCTTACTGCAGCCTTTGCCTCCCCGGCTCGAGCAGTCC

TGCCTCAGCCTCCGGAGTAGCTGGGACCACAGGTTCATGCCACCATG

GCCAGCCAACTTTTGCATGTTTTGTAGAGATGGGGTCTCACAGTGTT

GCCCAGGCTGGTCTCAAACTCCTGGGCTCAGGCGATCCACCTGTCTC

AGCCTCCCAGAGTGCTGGGATTACAATTGTGAGCCACCACGTCCAGC

TGGAAGGGTCAACATCTTTTACATTCTGCAAGCACATCTGCATTTTC

ACCCCACCCTTCCCCTCCTTCTCCCTTTTTATATCCCATTTTTATAT

CGATCTCTTATTTTACAATAAAACTTTGCTGCCACCTGTGTGTCTGA

GGGGTG.
```

Esophageal adenocarcinoma (EAC) has steadily increased in incidence over recent decades. With an 85% mortality rate this cancer is the most rapidly increasing cause of cancer mortality from solid tumors in the American population. There has thus been substantial interest in development of screening approaches for early detection of EAC and its precursor lesions of Barrett's esophagus (BE). However, the majority of EACs develop in patients without prior symptoms, and current approaches of endoscopic screening of individuals with persistent symptoms of gastro-esophageal reflux disease, combined with longitudinal screening of those found to have BE, have accordingly not had significant impact on reducing deaths from EACs.

As noted above, early detection of gastrointestinal neoplasia (e.g., neoplasia of the upper gastrointestinal tract) coupled with appropriate intervention, is important for increasing patient survival rates. Present systems for screening for esophageal neoplasia are deficient for a variety of reasons, including a lack of specificity and/or sensitivity (e.g., barium swallow) or a high cost and intensive use of medical resources (e.g., upper endoscopy or CT scan). Alternative systems for detection of esophageal neoplasia would be useful in a wide range of other clinical circumstances as well. For example, detecting esophageal neoplasia may select the patient to undergo therapies that include, but are not limited, to resection of the neoplasia (via endoscopic resection or surgical resection), ablation of the neoplasia, chemotherapy, or radiation therapy. As a further example, patients who have received surgical and/or pharmaceutical therapy for esophageal cancer may experience a relapse. It would be advantageous to have an alternative system for determining whether such patients have a recurrent or relapsed neoplasia of the upper gastrointestinal tract. As a further example, an alternative diagnostic system would facilitate monitoring an increase, decrease or persistence of neoplasia of the upper gastrointestinal tract in a patient known to have such a neoplasia. A patient undergoing chemotherapy may be monitored to assess the effectiveness of the therapy.

III. Methylation of Informative Loci as Disease Biomarkers

The present disclosure relates at least in part to the identification of genomic loci whose altered DNA methylation is indicative of the presence of esophageal neoplasias and/or metaplasias that include Barrett's esophagus (BE) and/or esophageal adenocarcinoma (EAC). In some embodiments, the Barrett's esophagus is associated with dysplasia. In some embodiments, the dysplasia is high-grade dysplasia. In some embodiments, the dysplasia is low-grade dysplasia. In some embodiments, the methylation patterns of the informative loci as disclosed herein are determined in a sample taken from a subject as described herein and may be used to distinguish between subjects having Barrett's esophagus and subjects having high grade dysplasia and/or low grade dysplasia and/or esophageal adenocarcinoma. Examples of the informative loci are provided herein.

In some embodiments, any of the nucleotide sequences disclosed herein, or fragments or reverse complements thereof, may contain one or more "Y" residues. Cytosine residues that may be methylated or unmethylated, and hence may be bisulfite converted to T (if unmethylated) or remain as a C (if methylated), are designated with a "Y." In some embodiments, one or more of the Y residues in any of the sequences disclosed herein (or fragments or reverse complements thereof) designates a methylated C. In some embodiments, one or more of the Y residues in any of the sequences disclosed herein (or fragments or reverse complements thereof) designates an unmethylated C. In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues in any of the sequences disclosed herein (or fragments or reverse complements thereof) correspond to methylated C residues. In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues in any of the sequences disclosed herein (or fragments or reverse complements thereof) correspond to unmethylated C residues. In some embodiments, at least 10%, 20%, 30%, 40%, 50%, 60%, 70%, 80%, 90%, or 100% of the Y residues in any of the sequences disclosed herein (or fragments or reverse complements thereof) correspond to methylated C residues. In some embodiments, at least 10%, 20%, 30%, 40%, 50%, 60%, 70%, 80%, 90%, or 100% of the Y residues in any of the sequences disclosed herein (or fragments or reverse complements thereof) are correspond to unmethylated C residues. In some embodiments, any of the sequences disclosed herein (or fragments or reverse complements thereof) is bisulfite-converted. In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues in any of the bisulfite-converted sequences disclosed herein (or fragments or reverse complements thereof) correspond to C. In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues in any of the bisulfite-converted sequences disclosed herein (or fragments or reverse complements thereof) correspond to T. In some embodiments, at least 10%, 20%, 30%, 40%, 50%, 60%, 70%, 80%, 90%, or 100% of the Y residues in any of the bisulfite-converted sequences disclosed herein (or fragments or reverse complements thereof) correspond to C residues. In some embodiments, at least 10%, 20%, 30%, 40%, 50%, 60%, 70%, 80%, 90%, or 100% of the Y residues in any of the bisulfite-converted sequences disclosed herein (or fragments or reverse complements thereof) correspond to T residues.

In some embodiments, an informative loci in a subject is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma) if the loci is at least 10%, 20%, 30%, 40%, 50%, 60%, 70%, 80%, 90%, or 100% methylated. In some embodiments, a DNA sample from a subject is treated with bisulfite, and the resulting bisulfite sequence corresponds to any of the nucleotide sequences disclosed herein comprising a "Y" nucleotide. In some embodiments, if at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues of the bisulfite-converted sequence have a C, the sequence is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma). In some embodiments, a DNA sample from a subject is treated with bisulfite, and the resulting bisulfite sequence corresponds to any of the nucleotide sequences disclosed herein comprising a "Y" nucleotide. In some embodiments, if at least 10%, 20%, 30%, 40%, 50%, 60%, 70%, 80%, 90%, or 100% of the Y residues of the bisulfite-converted sequence have a C, the sequence is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma). The disclosure provides for informative loci that may be used to assess whether a subject (e.g. a human) has or is prone to developing a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma). In some embodiments, one or more informative loci, as defined herein, may be used for determining whether a subject has or is likely to develop, a metaplasia (e.g., Barrett's esophagus). In some embodiments, one or more informative loci, as defined herein, may be used for determining whether a subject has or is likely to develop, a neoplasia (e.g., Barrett's esophagus with high grade dysplasia, or an esophageal cancer such as esophageal adenocarcinoma). In some embodiments, one or more informative loci, as defined herein, may be used to distinguish between whether a subject has a metaplasia in the esophagus (e.g., Barrett's esophagus) or an esophageal neoplasia (e.g., Barrett's esophagus with high grade dysplasia, or an esophageal cancer such as esophageal adenocarcinoma).

In some embodiments, the informative loci include sequences associated with any one or more of the plus strand DNA sequences having at least 80%, 85%, 87%, 90%, 91%, 92%, 93%, 94%, 95%, 96%, 97%, 98%, 99% or 100% identity to any of SEQ ID NOs: 1-428, 2569-2996, 5137-5531, 7507-7532, 7663-7668, 7819-7842, 7963-7976, 8047-8060, 8131-8143, 8209-8222, 8293-8306, 8405-8409, 8447-8632, 9563-9748, 10679-10825, 11561-11611, 11867-11917, 12173-12219, 12455-12460, 12491-12496, 12527-12532, 12563-12568, 12599-12604, 12647-12649, 12671-12907, 14093-14329, 15515-15537, 15653-15692, 15893-15932, 16133-16137, 16163-16165, 16181-16183, or 16199, or fragments or complements thereof. In particular embodiments, the informative loci include sequences associated with any one or more of the plus strand DNA sequences having at least 80%, 85%, 87%, 90%, 91%, 92%, 93%, 94%, 95%, 96%, 97%, 98%, 99% or 100% identity to any of SEQ ID NOs: 7963-7976, 8047-8060, 8131-8143, 12455-12460, 12491-12496, 12527-12532, 16163-16165, 16181-16183, or 16199, or fragments or complements thereof. In some embodiments, the informative loci are associated with increased methylation in both Barrett's esophagus and esophageal adenocarcinoma samples, as compared to the same sample types taken from a healthy control subject. In some embodiments, the informative loci that are associated with increased methylation in both Barrett's esophagus and esophageal adenocarcinoma samples include sequences associated with any one or more of the plus strand DNA sequences having at least 80%, 85%, 87%, 90%, 91%, 92%, 93%, 94%, 95%, 96%, 97%, 98%, 99% or 100% identity to any of SEQ ID NOs: 1-428, 2569-2996, 5137-5531, 7507-7532, 7663-7668, 7819-7842, 7963-7976, 8047-8060, 8131-8143, 8209-8222, 8293-8306, or 8405-8409, or fragments or complements thereof. In particular embodiments, the informative loci that are associated with increased methylation in both Barrett's esophagus and esophageal adenocarcinoma samples include sequences associated with any one or more of the plus strand DNA sequences having at least 80%, 85%, 87%, 90%, 91%, 92%, 93%, 94%, 95%, 96%, 97%, 98%, 99% or 100% identity to any of SEQ ID NOs: 7963-7976, 8047-8060, or 8131-8143, or fragments or complements thereof. In some embodiments, the informative loci are associated with increased methylation in an esophageal adenocarcinoma sample and/or a Barrett's with low grade or high grade dysplasia as compared to a sample of the same type taken from a subject having Barrett's esophagus without dysplasia. In some embodiments, the informative loci that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 8447-8632, 9563-9748, 10679-10825, 11561-11611, 11867-11917, 12173-12219, 12455-12460, 12491-12496, or 12527-12532, or fragments or complements thereof. In particular embodiments, the informative loci that are associated with increased methylation in Barrett's with low grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 12455-12460, 12491-12496, or 12527-12532, or fragments or complements thereof. In particular embodiments, the informative loci that are associated with increased methylation in an esophageal adenocarcinoma sample or a Barrett's with high grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 12455-12460, 12491-12496, or 12527-12532, or fragments or complements thereof. In some embodiments, the informative loci are associated with reduced methylation in an esophageal adenocarcinoma sample as compared to a sample of the same type taken from a subject having Barrett's esophagus. In some embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to any of SEQ ID NOs: 12671-12908, 14093-14329, 15515-15537, 15653-15692, 15893-15932, 16133-16137, 16163-16165, 16181-16183, or 16199, or fragments or complements thereof. In particular embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to any of SEQ ID NOs: 16163-16165, 16181-16183, or 16199, or fragments or complements thereof.

In some embodiments, the informative loci or amplicon of the informative loci are treated with an agent, such as bisulfite. In some embodiments, the informative loci include sequences that have been treated with bisulfite. In some embodiments, the disclosure provides for bisulfite control sequences of any of the plus DNA strands disclosed herein. In some embodiments, the disclosure provides for bisulfite-treated unmethylated sequences of any of the plus DNA strands disclosed herein. In some embodiments, the bisulfite-converted plus-strand control DNA sequences include any one or more having at least 80%, 85%, 87%, 90%, 91%, 92%, 93%, 94%, 95%, 96%, 97%, 98%, 99% or 100% identity to any of SEQ ID NOs: 857-1284, 3425-3852, 5927-6321, 7559-7584, 7715-7740, 7867-7890, 7991-8004, 8075-8088, 8157-8169, 8223-8236, 8307-8320, 8410-8414, 8819-9004, 9935-10120, 10973-11119, 11663-11713, 11969-12019, 12267-12313, 12467-12472, 12503-12508, or 12539-12544, 12569-12574, 12605-12610, 12650-12652, or fragments or complements thereof. In particular embodiments, the bisulfite-converted plus-strand control DNA sequences include any one or more having at least 80%, 85%, 87%, 90%, 91%, 92%, 93%, 94%, 95%, 96%, 97%, 98%, 99% or 100% identity to any of SEQ ID NOs: 7991-8004, 8075-8088, 8157-8169, 8223-8236, 8307-8320, 8410-8414, 12467-12472, 12503-12508, or 12539-12544, 12569-12574, 12605-12610, 12650-12652, or fragments or complements thereof. In some embodiments, the informative loci are associated with increased methylation in both Barrett's esophagus and esophageal adenocarcinoma samples, as compared to the same sample types taken from a healthy control subject. In some embodiments, the disclosure provides for bisulfite-treated unmethylated sequences of any of the plus DNA strands that are associated with increased methylation in both Barrett's esophagus and esophageal adenocarcinoma samples, as compared to the same sample types taken from a healthy control subject. In some embodiments, the bisulfite converted sequences of any of the plus DNA strands that are associated with increased methylation in both Barrett's esophagus and esophageal adenocarcinoma samples are selected from the group consisting of sequences having at least 80%, 85%, 87%, 90%, 91%, 92%, 93%, 94%, 95%, 96%, 97%, 98%, 99% or 100% identity to any of SEQ ID NOs: 857-1284, 3425-3852, 5927-6321, 7559-7584, 7715-7740, 7867-7890, 7991-8004, 8075-8088, 8157-8169, 8223-8236, 8307-8320, or 8410-8414, or fragments or complements thereof. In particular embodiments, the bisulfite converted sequences of any of the plus DNA strands that are associated with increased methylation in both Barrett's esophagus and esophageal adenocarcinoma samples include any one or more bisulfite-converted methylated plus-strand DNA sequences selected from the group consisting of sequences having at least 80%, 85%, 87%, 90%, 91%, 92%, 93%, 94%, 95%, 96%, 97%, 98%, 99% or 100% identity to any of: SEQ ID NOs: 7991-8004, 8075-8088, 8157-8169, 8223-8236, 8307-8320, or 8410-8414, or fragments or complements thereof. In some embodiments, the disclosure provides for bisulfite-treated unmethylated sequences of any of the plus DNA strands that are associated with increased methylation in an esophageal adenocarcinoma sample or a Barrett's with low grade or high grade dysplasia sample as compared to a sample of the same type taken from a subject having Barrett's esophagus without dysplasia. In some embodiments, the bisulfite converted sequences of any of the plus DNA strands that are associated with increased methylation in an esophageal adenocarcinoma sample or a Barrett's with low grade or high grade dysplasia sample include any one or more bisulfite-converted methylated plus-strand DNA sequences selected from the group consisting having at least 80%, 85%, 87%, 90%, 91%, 92%, 93%, 94%, 95%, 96%, 97%, 98%, 99% or 100% identity to any of SEQ ID NOs: 8819-9004, 9935-10120, 10973-11119, 11663-11713, 11969-12019, 12267-12313, 12467-12472, 12503-12508, 12539-12544, 12569-12574, 12605-12610, or 12650-12652, or fragments or complements thereof. In particular embodiments, the bisulfite converted sequences of any of the plus DNA strands that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 12467-12472, 12503-12508, 12539-12544, 12569-12574, 12605-12610, or 12650-12652, or fragments or complements thereof. In some embodiments, the informative loci are associated with reduced methylation in an esophageal adenocarcinoma sample as compared to a sample of the same type taken from a subject having Barrett's esophagus. In some embodiments, the disclosure provides for methylated control sequences of the plus DNA strand that are associated with reduced methylation in an esophageal adenocarcinoma sample as compared to a sample of the same type taken from a subject having Barrett's esophagus. In some embodiments, the methylated control sequences of any of the plus DNA strands that are associated with reduced methylation in an esophageal adenocarcinoma sample include any one or more bisulfite-converted methylated plus-strand DNA sequences selected from the group consisting having at least 80%, 85%, 87%, 90%, 91%, 92%, 93%, 94%, 95%, 96%, 97%, 98%, 99% or 100% identity to any of SEQ ID NOs: 13145-13381, 14567-14803, 15561-15583, 15733-15772, 15973-16012, 16143-16147, 16169-16171, 16187-16189 or 16201, or fragments or complements thereof. In particular embodiments, the methylated control sequences of any of the plus DNA strands that are associated with reduced methylation in an esophageal adenocarcinoma sample include any one or more bisulfite-converted methylated plus-strand DNA sequences selected from the group consisting having at least 80%, 85%, 87%, 90%, 91%, 92%, 93%, 94%, 95%, 96%, 97%, 98%, 99% or 100% identity to any of SEQ ID NOs: 16169-16171, 16187-16189 or 16201, or fragments or complements thereof.

In some embodiments, the informative loci or amplicon of the informative loci are treated with an agent, such as bisulfite. In some embodiments, the informative loci include sequences that have been treated with bisulfite. In some embodiments, the informative loci include methylated nucleic acid sequences that have been treated with bisulfite. In some embodiments, the bisulfite-converted methylated plus-strand DNA sequences have at least 80%, 85%, 87%, 90%, 91%, 92%, 93%, 94%, 95%, 96%, 97%, 98%, 99% or 100% identity to any of SEQ ID NOs: 1285-1712, 3853-4280, 6322-6716, 7585-7610, 7741-7766, 7891-7914, 8005-8018, 8089-8102, 8170-8182, 8237-8250, 8321-8334, 8415-8419, 9005-9190, 10121-10306, 11120-11266, 11714-11764, 12020-12070, 12314-12360, 12473-12478, 12509-12514 or 12545-12550, 12575-12580, 12611-12616, 12653-12655, or fragments or complements thereof. In particular embodiments, the bisulfite-converted methylated plus-strand DNA sequences have at least 80%, 85%, 87%, 90%, 91%, 92%, 93%, 94%, 95%, 96%, 97%, 98%, 99% or 100% identity to any of SEQ ID NOs: 8005-8018, 8089-8102, 8170-8182, 12473-12478, 12509-12514 or 12545-12550, or fragments or complements thereof. In some embodiments, the informative loci are associated with increased methylation in both Barrett's esophagus and esophageal adenocarcinoma samples, as compared to the same sample types taken from a healthy control subject. In some embodiments, the informative loci that are associated with increased methylation in both Barrett's esophagus and esophageal adenocarcinoma samples include any one or more bisulfite-converted methylated plus-strand DNA sequences selected from the group consisting of sequences having at least 80%, 85%, 87%, 90%, 91%, 92%, 93%, 94%, 95%, 96%, 97%, 98%, 99% or 100% identity to any of SEQ ID NOs: 1285-1712, 3853-4280, 6322-6716, 7585-7610, 7741-7766, 7891-7914, 8005-8018, 8089-8102, 8170-8182, 8237-8250, 8321-8334, or 8415-8419, or fragments or complements thereof. In particular embodiments, the informative loci that are associated with increased methylation in both Barrett's esophagus and esophageal adenocarcinoma samples include any one or more bisulfite-converted methylated plus-strand DNA sequences selected from the group consisting of sequences having at least 80%, 85%, 87%, 90%, 91%, 92%, 93%, 94%, 95%, 96%, 97%, 98%, 99% or 100% identity to: SEQ ID NOs: 8005-8018, 8089-8102, 8170-8182, 8237-8250, 8321-8334, or 8415-8419, or fragments or complements thereof. In some embodiments, the informative loci are associated with increased methylation in an esophageal adenocarcinoma sample or a Barrett's with low grade or high grade dysplasia sample as compared to a sample of the same type taken from a subject having Barrett's esophagus without dysplasia. In some embodiments, the informative loci that are associated with increased methylation in an esophageal adenocarcinoma sample or a Barrett's with low grade or high grade dysplasia sample include any one or more bisulfite-converted methylated plus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 9005-9190, 10121-10306, 11120-11266, 11714-11764, 12020-12070, 12314-12360, 12473-12478, 12509-12514, 12545-12550, 12575-12580, 12611-12616, or 12653-12655, or fragments or complements thereof. In particular embodiments, the informative loci that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to SEQ ID NOs: 12473-12478, 12509-12514, 12545-12550, 12575-12580, 12611-12616, or 12653-12655, or fragments or complements thereof. In some embodiments, the informative loci are associated with reduced methylation in an esophageal adenocarcinoma sample as compared to a sample of the same type taken from a subject having Barrett's esophagus. In some embodiments, the informative loci that are associated with reduced methylation in an esophageal adenocarcinoma sample include any one or more bisulfite-converted methylated plus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 13382-13618, 14804-15040, 15584-15606, 15773-15812, 16013-16052, 16148-16152, 16172-16174, 16190-16192 or 16202. In particular embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to SEQ ID NOs: 16172-16174, 16190-16192 or 16202, or fragments or complements thereof.

In some embodiments, the informative loci include sequences associated with any of the minus strand DNA sequences having at least 80%, 85%, 87%, 90%, 91%, 92%, 93%, 94%, 95%, 96%, 97%, 98%, 99% or 100% identity to any of SEQ ID NOs: 429-856, 2997-3424, 5532-5926, 7533-7558, 7689-7714, 7843-7866, 7977-7990, 8061-8074, 8144-8156, 8251-8264, 8335-8348, 8420-8424, 8633-8818, 9749-9934, 10826-10972, 11612-11662, 11918-11968, 12220-12266, 12461-12466, 12497-12502, 12533-12538, 12581-12586, 12617-12622, 12656-12658, 12909-13144, 14330-14566, 15538-15560, 15693-15732, 15933-15972, 16138-16142, 16166-16168, 16184-16186 or 16200, or fragments or complements thereof. In particular embodiments, the informative loci include sequences associated with any of the minus strand DNA sequences having at least 80%, 85%, 87%, 90%, 91%, 92%, 93%, 94%, 95%, 96%, 97%, 98%, 99% or 100% identity to any of SEQ ID NOs: 7977-7990, 8061-8074, 8144-8156, 8251-8264, 8335-8348, 8420-8424, 12461-12466, 12497-12502, 12533-12538, 12581-12586, 12617-12622, 12656-12658, 16166-16168, 16184-16186 or 16200, or fragments or complements thereof. In some embodiments, the informative loci are associated with increased methylation in both Barrett's esophagus and esophageal adenocarcinoma samples, as compared to the same sample types taken from a healthy control subject. In some embodiments, the informative loci that are associated with increased methylation in both Barrett's esophagus and esophageal adenocarcinoma samples include sequences associated with any one or more of the minus strand DNA sequences having at least 80%, 85%, 87%, 90%, 91%, 92%, 93%, 94%, 95%, 96%, 97%, 98%, 99% or 100% identity to any of SEQ ID NOs: 429-856, 2997-3424, 5532-5926, 7533-7558, 7689-7714, 7843-7866, 7977-7990, 8061-8074, 8144-8156, 8251-8264, 8335-8348, 8420-8424, or fragments or complements thereof. In particular embodiments, the informative loci that are associated with increased methylation in both Barrett's esophagus and esophageal adenocarcinoma samples include sequences associated with any one or more of the plus strand DNA sequences having at least 80%, 85%, 87%, 90%, 91%, 92%, 93%, 94%, 95%, 96%, 97%, 98%, 99% or 100% identity to any of SEQ ID NOs: 8251-8264, 8335-8348. 8420-8424, or fragments or complements thereof. In some embodiments, the informative loci are associated with increased methylation in an esophageal adenocarcinoma sample or a Barrett's with low grade or high grade dysplasia sample as compared to a sample of the same type taken from a subject having Barrett's esophagus without dysplasia. In some embodiments, the informative loci that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 8633-8818, 9749-9934, 10826-10972, 11612-11662, 11918-11968, 12220-12266, 12461-12466, 12497-12502, 12533-12538, 12581-12586, 12617-12622, or 12656-12658, or fragments or complements thereof. In particular embodiments, the informative loci that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to any of SEQ ID NOs: 12461-12466, 12497-12502, 12533-12538, 12581-12586, 12617-12622, or 12656-12658, or fragments or complements thereof. In some embodiments, the informative loci are associated with reduced methylation in an esophageal adenocarcinoma sample as compared to a sample of the same type taken from a subject having Barrett's esophagus. In some embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to any of SEQ ID NOs: 12909-13144, 14330-14566, 15538-15560, 15693-15732, 15933-15972, 16138-16142, 16166-16168, 16184-16186 or 16200, or fragments or complements thereof. In particular embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to any of SEQ ID NOs: 16166-16168, 16184-16186 or 16200, or fragments or complements thereof.

In some embodiments, the informative loci or amplicon of the informative loci are treated with an agent, such as bisulfite. In some embodiments, the informative loci include sequences that have been treated with bisulfite. In some embodiments, the disclosure provides for bisulfite control sequences of any of the minus DNA strands disclosed herein. In some embodiments, the disclosure provides for bisulfite-treated sequences of any of the minus DNA strands disclosed herein. In some embodiments, the bisulfite-converted minus-strand control DNA sequences include any one or more of the sequences having at least 80%, 85%, 87%, 90%, 91%, 92%, 93%, 94%, 95%, 96%, 97%, 98%, 99% or 100% identity to any of SEQ ID NOs: 1713-2140, 4281-4708, 6717-7111, 7611-7636, 7767-7792, 7915-7938, 8019-8032, 8103-8116, 8183-8195, 8265-8278, 8349-8362, 8425-8429, 9191-9376, 10307-10492, 11267-11413, 11765-11815, 12071-12121, 12361-12407, 12479-12484, 12515-12520, 12551-12556, 12587-12592, 12623-12628, or 12659-12661, or fragments or complements thereof. In particular embodiments, the bisulfite-converted minus-strand control DNA sequences include any one or more the sequences having at least 80%, 85%, 87%, 90%, 91%, 92%, 93%, 94%, 95%, 96%, 97%, 9, 98%, 99% or 100% identity to any of SEQ ID NOs: 8019-8032, 8103-8116, 8183-8195, 12479-12484, 12515-12520, or 12551-12556, or fragments or complements thereof. In some embodiments, the informative loci are associated with increased methylation in both Barrett's esophagus and esophageal adenocarcinoma samples, as compared to the same sample types taken from a healthy control subject. In some embodiments, the disclosure provides for bisulfite-treated sequences of any of the minus DNA strands that are associated with increased methylation in both Barrett's esophagus and esophageal adenocarcinoma samples, as compared to the same sample types taken from a healthy control subject. In some embodiments, the sequences of any of the minus DNA strands that are associated with increased methylation in both Barrett's esophagus and esophageal adenocarcinoma samples are selected from the group consisting of sequences having at least 80%, 85%, 87%, 90%, 91%, 92%, 93%, 94%, 95%, 96%, 97%, 98%, 99% or 100% identity to any of SEQ ID NOs: 1713-2140, 4281-4708, 6717-7111, 7611-7636, 7767-7792, 7915-7938, 8019-8032, 8103-8116, 8183-8195, 8265-8278, 8349-8362, or 8425-8429, or fragments or complements thereof. In particular embodiments, the sequences of any of the minus DNA strands that are associated with increased methylation in both Barrett's esophagus and esophageal adenocarcinoma samples include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to: SEQ ID NOs: 8019-8032, 8103-8116, 8183-8195, 8265-8278, 8349-8362, or 8425-8429, or fragments or complements thereof. In some embodiments, the disclosure provides for bisulfite-treated sequences of any of the minus DNA strands that are associated with increased methylation in an esophageal adenocarcinoma sample or a Barrett's with low grade or high grade dysplasia sample as compared to a sample of the same type taken from a subject having Barrett's esophagus without dysplasia. In some embodiments, the sequences of any of the minus DNA strands that are associated with increased methylation in an esophageal adenocarcinoma sample or a Barrett's with low grade or high grade dysplasia sample include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 9191-9376, 10307-10492, 11267-11413, 11765-11815, 12071-12121, 12361-12407, 12479-12484, 12515-12520, or 12551-12556, 12587-12592, 12623-12628, or 12659-12661, or fragments or complements thereof. In particular embodiments, the unmethylated sequences of any of the minus DNA strands that are associated with increased methylation in an esophageal adenocarcinoma sample or a Barrett's with low grade or high grade dysplasia sample include any one or more of the sequences having at least 80%, 85%, 87%, 90%, 91%, 92%, 93%, 94%, 95%, 96%, 97%, 98%, 99% or 100% identity to SEQ ID NOs: 12479-12484, 12515-12520, 12551-12556, 12587-12592, 12623-12628, or 12659-12661, or fragments or complements thereof. In some embodiments, the informative loci are associated with reduced methylation in an esophageal adenocarcinoma sample as compared to a sample of the same type taken from a subject having Barrett's esophagus. In some embodiments, the disclosure provides for methylated control sequences of the minus DNA strand that are associated with reduced methylation in an esophageal adenocarcinoma sample as compared to a sample of the same type taken from a subject having Barrett's esophagus. In some embodiments, the methylated control sequences of any of the minus DNA strands that are associated with reduced methylation in an esophageal adenocarcinoma sample include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 13619-13855, 15041-15277, 15607-15629, 15813-15852, 16053-16092, 16153-16157, 16175-16177, 16192-16195 or 16203, or fragments or complements thereof. In particular embodiments, the methylated control sequences of any of the minus DNA strands that are associated with reduced methylation in an esophageal adenocarcinoma sample include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 16175-16177, 16192-16195 or 16203, or fragments or complements thereof.

In some embodiments, the informative loci or amplicon of the informative loci are treated with an agent, such as bisulfite. In some embodiments, the informative loci include sequences that have been treated with bisulfite. In some embodiments, the informative loci include methylated nucleic acid sequences that have been treated with bisulfite.

In some embodiments, the bisulfite-converted methylated minus-strand DNA sequences include any one or more of sequences having at least 80%, 85%, 87%, 90%, 91%, 92%, 93%, 94%, 95%, 96%, 97%, 98%, 99% or 100% identity to SEQ ID NOs: 2141-2568, 4709-5136, 7112-7506, 7637-7662, 7793-7818, 7939-7962, 8033-8046, 8117-8130, 8196-8208, 8279-8292, 8363-8376, 8430-8434, 9377-9562, 10493-10678, 11414-11560, 11816-11866, 12122-12172, 12408-12454, 12485-12490, 12521-12526, 12557-12562, 12593-12598, 12269-12634, or 12662-12664, or fragments or complements thereof. In particular embodiments, the bisulfite-converted methylated minus-strand DNA sequences include any one or more of sequences having at least 80%, 85%, 87&% 90%, 91%, 92&% 93%, 94%, 95%, 96%, 97%, 98&% 99% or 100% identity to SEQ ID NOs: 8033-8046, 8117-8130, 8196-8208, 8279-8292, 8363-8376, 8430-8434, 12485-12490, 12521-12526, 12557-12562, 12593-12598, 12269-12634, or 12662-12664, or fragments or complements thereof. In some embodiments, the informative loci are associated with increased methylation in both Barrett's esophagus and esophageal adenocarcinoma samples, as compared to the same sample types taken from a healthy control subject. In some embodiments, the informative loci that are associated with increased methylation in both Barrett's esophagus and esophageal adenocarcinoma samples include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 2141-2568, 4709-5136, 7112-7506, 7637-7662, 7793-7818, 7939-7962, 8033-8046, 8117-8130, 8196-8208, 8279-8292, 8363-8376, or 8430-8434, or fragments or complements thereof. In particular embodiments, the informative loci that are associated with increased methylation in both Barrett's esophagus and esophageal adenocarcinoma samples include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to: SEQ ID NOs: 8033-8046, 8117-8130, 8196-8208, 8279-8292, 8363-8376, or 8430-8434, or fragments or complements thereof. In some embodiments, the informative loci are associated with increased methylation in an esophageal adenocarcinoma sample or a Barrett's with high grade dysplasia sample as compared to a sample of the same type taken from a subject having Barrett's esophagus without dysplasia. In some embodiments, the informative loci that are associated with increased methylation in an esophageal adenocarcinoma sample or a Barrett's with low grade or high grade dysplasia sample include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 9377-9562, 10493-10678, 11414-11560, 11816-11866, 12122-12172, 12408-12454, 12485-12490, 12521-12526, 12557-12562, 12593-12598, 12269-12634, or 12662-12664, or fragments or complements thereof. In particular embodiments, the informative loci that are associated with increased methylation in an esophageal adenocarcinoma sample or a Barrett's with low grade or high grade dysplasia sample include any one or more of the sequences of sequences having at least 80%, 85%, 87%, 90%, 91%, 92%, 93%, 94%, 95%, 96%, 97%, 98%, 99% or 100% identity to SEQ ID NOs: 12485-12490, 12521-12526, 12557-12562, 12593-12598, 12269-12634, or 12662-12664, or fragments or complements thereof. In some embodiments, the informative loci are associated with reduced methylation in an esophageal adenocarcinoma sample as compared to a sample of the same type taken from a subject having Barrett's esophagus. In some embodiments, the informative loci that are associated with reduced methylation in an esophageal adenocarcinoma sample include any one or more bisulfite-converted methylated minus-strand DNA sequences selected from the group consisting of sequences having at least 80%, 85%, 87%, 90%, 91%, 92%, 93%, 94%, 95%, 96%, 97%, 98%, 99% or 100% identity to SEQ ID NOs: 13856-14092, 15278-15514, 15630-15652, 15853-15892, 16093-16132, 16158-16162, 16178-16180, 16196-16198, or 16204, or fragments or complements thereof. In particular embodiments, the informative loci that are associated with reduced methylation in an esophageal adenocarcinoma sample include any one or more of the sequences having at least 80%, 85%, 87%, 90%, 91%, 92%, 93%, 94%, 95%, 96%, 97%, 98%, 99% or 100% identity to SEQ ID NOs: 16178-16180, 16196-16198, or 16204, or fragments or complements thereof.

In some embodiments, the disclosure provides for a bisulfite-converted nucleotide sequence comprising the bisulfite-converted nucleotide sequence of any one of the following: Up3, Up10, Up15-1, Up15-2, Up20-1, Up20-2, Up20-2, Up27, Up35-1, Up35-2, SqBE2, SqBE5. SqBE7, SqBE9, SqBE10, SqBE11-1, SqBE 1-2, SqBE13, SqBE14-2. SqBE15, SqBE16-1, SqBE16-2, SqBE17-1, SqBE18. SqBE22-1, SqBE22-2 or SqBE23. In particular embodiments, the sequence comprises the bisulfite-converted nucleotide sequence of any one of the following: Up3, Up10, Up15-1, Up15-2, Up20-1, Up20-2, Up20-2, Up27, Up35-1, or Up35-2. In particular embodiments, the sequence comprises the bisulfite-converted nucleotide sequence of any one of the following: SqBE2, SqBE5, SqBE7, SqBE9, SqBE 10, SqBE11-1, SqBE11-2, SqBE13, SqBE14-2. SqBE15, SqBE16-1, SqBE16-2, SqBE17-1, SqBE18, SqBE22-1, SqBE22-2 or SqBE23.

In some embodiments, the disclosure provides for a panel of any of the sequences disclosed herein. In some embodiments, the panel comprises any of the following combinations of sequences: a) Up3, Up10, Up15-1, Up15-2, Up20-1, Up20-2, Up27, Up35-1, and Up35-2; b) Up3, Up15-1, Up15-2, Up20-1, Up27, and Up35-1: c) Up10, Up3, Up15-1, Up15-2, Up20-1, Up27, and Up35-1; d) Up35-2, Up3, Up15-1, Up15-2, Up20-1, Up27 and Up35-1; e) Up15-1 and Up35-1; f) Up15-1, Up35-1, and Up10; g) Up15-1, Up35-1 and Up20-1; h) Up15-1, Up35-1, Up10, and Up15-2; i) Up15-1, Up35-1, Up10, and Up27; j) Up15-1, Up35-1, Up15-2, and Up20-1; k) Up15-1, Up35-1, Up15-2 and Up27: 1) Up15-1, Up35-1, Up20-1, and Up27; m) Up3 and Up35-1: n) Up3 and Up35-2; o) Up3 and Up10; p) Up3 and Up27; q) Up35-1 and Up35-2; r) Up35-1 and Up27; s) Up35-2 and Up10; t) Up10 and Up27; u) Up3, Up35-1 and Up35-2; v) Up3, Up35-1 and Up10; w) Up3, Up35-1, and Up27; x) Up3, Up35-2 and Up10; y) Up3, Up35-2, and Up27; z) Up3, Up10, and Up27; aa) Up35-1, Up10, and Up27; ab) Up35-2, Up10, and Up27; ac) Up3, Up35-1, Up35-2 and Up10; ad) Up3, Up35-1, Up35-2 and Up27; ae) Up35-1, Up35-2, Up10 and Up27; af) Up3, Up35-2, Up10 and Up27; ag) Up3, Up35-1, Up10 and Up27; ah) Up3, Up10, Up27, Up35-1, and Up35-2; ai) Up35-1 and Up10, aj) Up35-1 and Up27; ak) Up35-2 and Up10; al) Up35-2 and Up27; am) Up3, Up35-1 and Up35-2; an) Up3, Up35-1, and Up10; ao) Up3, Up35-1, and Up27; ap) Up3, Up35-2 and Up10; aq) Up3, Up35-2 and Up27; ar) Up3, Up10 and Up27; at) Up35-1, Up10, and Up27; au) Up3, Up35-1, Up35-2, and Up10; av) Up3, Up35-1, Up35-2 and Up27; aw) Up35-1, Up35-2, Up10 and Up27; ax) Up3, Up35-2, Up10 and Up27; ay) Up3, Up35-1, Up10 and Up27; az) Up3, Up10, Up27, Up35-1, and Up35-2; ba) SqBE5 and SqBE7; bb) SqBE5 and SqBE16; bc) SqBE5 and SqBE17; bd) SqBE5 and SqBE18: be) SqBE7 and SqBE16; bf) SqBE7 and SqBE17; SqBE7 and SqBE17; bg) SqBE7 and SqBE18; bh) SqBE16 and SqBE17 and bi) SqBE16 and SqBE18. In some embodiments, the disclosure provides for a method of detecting the methylation status of the sequences in any of the panels disclosed herein. In some embodiments, the disclosure provides for a method of detecting the methylation status of the sequences in any of the panels disclosed herein, and further comprises detecting the mutation status of p53. In particular embodiments, the disclosure provides for a method of a) detecting the methylation status of a panel comprising the sequences of Up-3 and Up35-2, and b) further detecting the mutation status of TP53.

In some embodiments, the disclosure provides for a method of detecting the methylation status of any of the loci disclosed herein, and further comprises detecting the methylation status of vimentin. In some embodiments, the vimentin methylation is detected in a manner consistent with that described in Li et al. (Li M, et al. (2009) Sensitive digital quantification of DNA methylation in clinical samples. *Nat Biotechnol* 27(9):858-863). In some embodiments, the vimentin methylation patterns are determined in a nucleotide sequence having at least 80%, 85%, 90%, 91%, 92%, 93%, 94%, 95%, 96%, 97%, 98%, 99% or 100% identity to SEQ ID NO: 16207 or 16208. In some embodiments, the methylation patterns are determined in any of the following nucleic acid sequence combinations: a) vimentin and SQBE5; b) vimentin and SQBE7, c) vimentin and SQBE16, d) vimentin and SQBE17 or e) vimentin and SQBE 18.

In particular embodiments, the disclosure provides for a nucleotide sequence comprising a sequence having at least 80%, 85%, 90%, 91%, 92%, 93%, 94%, 95%, 96%, 97%, 98%, 99% or 100% identity to any of the following sequences: 8209-8222, 8251-8264, 8293-8306, 8335-8348, 8405-8409, 8420-8424, 12563-12568, 12581-12586, 12599-12604, 12617-12622, 12647-12649 or 12656-12658, or fragments and/or reverse complements thereof. In particular embodiments, the disclosure provides for a nucleotide sequence comprising a sequence having at least 80%, 85%, 90%, 91%, 92%, 93% 94%, 95%, 96% 97%, 98%, 99% or 100% identity to any of the following sequences: 12563-12568, 12581-12586, 12599-12604, 12617-12622, 12647-12649 or 12656-12658, or fragments and/or reverse complements thereof. In particular embodiments, the disclosure provides for a nucleotide sequence comprising a sequence having at least 80%, 85%, 90%, 91%, 92%, 93%, 94%, 95%, 96%, 97%, 98%, 99% or 100% identity to any of the following sequences: 8209-8222, 8251-8264, 8293-8306, 8335-8348, 8405-8409, or 8420-8424, or fragments and/or reverse complements thereof.

In some embodiments, the disclosure provides for a bisulfite-converted nucleotide sequence comprising a sequence having at least 80%, 85%, 90%, 91%, 92%, 93%, 94%, 95%, 96%, 97%, 98%, 99% or 100% identity to any of the following sequences: SEQ ID NOs: 8307-8313, 8315-8327, 8329-8334, 8349-8355, 8357-8369, 8371-8376, 8411, 8412, 8414, 8416, 8417, 8419, 8426, 8427, 8429, 8431, 8432, 8434, 12605-12616, 12623-12634, 12650-12655, or 12659-12664, or fragments and/or reverse complements thereof. In some embodiments, the sequence comprises a sequence having at least 80%, 85%, 90%, 91%, 92%, 93%, 94%, 95%, 96%, 97%, 98%, 99% or 100% identity to any of the following sequences: SEQ ID NOs: 8307-8313, 8315-8327, 8329-8334, 8349-8355, 8357-8369, 8371-8376, 8411, 8412, 8414, 8416, 8417, 8419, 8426, 8427, 8429, 8431, or 8432, 8434. In some embodiments, the sequence comprises a sequence having at least 80%, 85%, 90%, 91%, 92%, 93%, 94%, 95%, 96%, 97%, 98%, 99% or 100% identity to any of the following sequences: SEQ ID NOs: 12605-12616, 12623-12634, 12650-12655, or 12659-12664.

In some embodiments, the disclosure provides for a bisulfite-converted nucleotide sequence comprising a sequence having at least 80%, 85%, 90%° 91%, 92%, 93%, 94%, 95%, 96%, 97%, 98%, 99% or 100% identity to any of the following sequences: SEQ ID NOs: 8223-8250, 8265-8292, 12569-12580, or 12587-12598, or fragments and/or reverse complements thereof. In some embodiments, the sequence comprises a sequence having at least 80%, 85%, 90%, 91%, 92%, 93%, 94%, 95%, 96%, 97%, 98%, 99% or 100% identity to any of the following sequences: SEQ ID NOs: 8223-8250 or 8265-8292. In some embodiments, the sequence comprises a sequence having at least 80%, 85%, 90%, 91%, 92%, 93%, 94%, 95%, 96%, 97%, 98%, 99% or 100% identity to any of the following sequences: SEQ ID NOs: 12569-12580 or 12587-12598.

In some embodiments, the sample for use in any of the methods disclosed herein is a tissue sample taken from the subject. In some embodiments, the sample is tissue sample from the esophagus. In some embodiments, the sample is a biopsy or a brushing. In some embodiments, the sample is a biopsy or brushing of the esophagus. In some embodiments, the sample is a body fluid. In some embodiments, the body fluid is blood, serum, saliva, spit, stool, urine or an esophageal washing.

The present disclosure contemplates methods of selecting an individual to undergo a diagnostic procedure to determine the presence of Barrett's esophagus, Barrett's esophagus with dysplasia (e.g., Barrett's esophagus with low-grade or high-grade dysplasia), or of esophageal adenocarcinoma, by obtaining a biological sample from an individual, and determining in the sample the presence of DNA methylation in at least one of any of the sequences disclosed herein. In some embodiments, the disclosure provides for a method of selecting a subject for monitoring of esophageal neoplasia, wherein the presence of DNA methylation in at least one of any of the sequences disclosed herein is detected in a sample from the subject. In some embodiments, detection is achieved by any one or more of DNA sequencing, next generation sequencing, methylation specific PCR, methylation specific PCR combined with a fluorogenic hybridization probe, real time methylation specific PCR, or hybridization to an array. In some embodiments, the detection in the sample is indicative that the subject is at high risk of progression to esophageal neoplasia (e.g., esophageal cancer). In some embodiments, the subject is monitored by endoscopy. In some embodiments, a sample from a subject in which DNA methylation of at least one of any of the sequences disclosed herein is detected, is indicative that the subject should be administered a particular treatment. In some embodiments, the treatment is selected from the group consisting of endoscopic removal or ablation of an esophageal neoplasia, and/or surgery, radiation, or chemotherapy treatment of esophageal adenocarcinoma. In some embodiments, the sequence is any one or more sequence selected from the group consisting of a sequence having at least 80%, 85%, 90%, 91%, 92%, 93%, 94%, 95%, 96%, 97%, 98%, 99% or 100% identity to any of the following sequences: SEQ ID NOs: 1-856, 2569-3424, 5137-5926: 7507-7558, 7663-7714, 7819-7866, 7963-7990, 8047-8074, 8131-8156, 8209-8222, 8251-8264, 8293-8306, 8335-8348, 8405-8409, and 8420-8424, or fragments or complements thereof.

The present disclosure also contemplates methods of selecting an individual to undergo a diagnostic procedure to determine presence of Barrett's esophagus with low-grade dysplasia, Barrett's esophagus with high grade dysplasia or of esophageal adenocarcinoma, by obtaining a biological sample from an individual, and determining in the sample the presence of DNA methylation in at least one of any of the sequences disclosed herein. In some embodiments, the sequence is any one or more sequence selected from the group consisting of sequences having at least 80%, 85%, 90%, 91%, 92%, 93%, 94%, 95%, 96%, 97%, 98%, 99% or 100% identity to any of the following sequences: SEQ ID NOs: 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, or 12656-12658, or fragments or complements thereof. The present disclosure further contemplates that the method may further comprise determining the status of somatic mutation(s) in TP53 in the sample. For example, a method comprising determining the status of methylation of chromosomal loci e.g. Up15-1, Up35-1, Up35-2, Up3, Up27, and Up100 in a sample; and determining the presence or absence of somatic mutation(s) in TP53 in the sample is contemplated.

The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated. In certain embodiments, the method optionally further comprises detecting the presence or absence of a somatic mutation in TP53. In certain embodiments, the TP53 somatic mutation, as described herein, is any one or more mutation at any one or more amino acid residue corresponding to amino acid residue 72, 105, 108, 110, 113, 124, 127, 132, 144, 152, 163, 175, 183, 194, 213, 214, 218, 232, 234, 248, 265, 273, 278, 306, 337, 347, or 639 of SEQ ID NO: 16205. In certain embodiments, the TP53 somatic mutation is any non-synonymous somatic mutation known in the art. In certain embodiments, the TP53 somatic mutation is any one or more mutation selected from the group consisting of: Leu194Arg, Gly105Asp, Arg273His, Tyr163His, Ile232Thr, Arg213Ter, Arg273His. Arg248Gln, Arg175His, Arg110delinsGlnSer, Ser183Ter, Arg248Gln, Arg337Leu, Lys132Arg, Leu265ThrfsTer7, Arg306Ter, Cys124TrpfsTer25, Pro72Arg, Val218Glu, His214Leu, Gln144Ter, Phe113Ser, Tyr234His, Ser127Phe, Pro278Ala, Ala347Thr, and Pro152Leu of SEQ ID NO: 16205 In certain embodiments, the TP53 mutation is any one or more non-synonymous somatic mutation at any one or more nucleotide position corresponding to nucleotide position 108, 215, 314, 338, 380, 395, 430, 455, 487, 524, 548, 581, 637, 639, 641, 653, 695, 700, 743, 818, 832, 916, 1010, or 1039 of SEQ ID NO: 16206.

The present disclosure also contemplates methods of selecting an individual to undergo a treatment for Barrett's esophagus, Barrett's esophagus with low grade dysplasia. Barrett's esophagus with high grade dysplasia or for esophageal adenocarcinoma, by obtaining a biological sample from an individual, and determining in the sample the presence of DNA methylation in at least one of any of the sequences disclosed herein. In some embodiments, the sequence is any one or more sequence selected from the group consisting of sequence having at least 80%, 85%, 90%, 91%, 92%, 93%, 94%, 95%, 96%, 97%, 98%, 99% or 100% identity to any of the following sequences: SEQ ID NOs: 1-856, 2569-3424, 5137-5926: 7507-7558, 7663-7714, 7819-7866, 7963-7990, 8047-8074, 8131-8156, 8209-8222, 8251-8264, 8293-8306, 8335-8348, 8405-8409, or 8420-8424, or fragments or complements thereof. In some embodiments, the present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated.

The present disclosure also contemplates methods of selecting an individual to undergo a treatment for Barrett's esophagus, Barrett's esophagus with low-grade dysplasia, Barrett's esophagus with high grade dysplasia or for esophageal adenocarcinoma, by obtaining a biological sample from an individual, and determining in the sample the presence of DNA methylation in at least one of any of the sequences disclosed herein. In some embodiments, the sequence is any one or more sequence selected from the group consisting of sequence having at least 80%, 85%, 90%, 91%, 92%, 93%, 94%, 95%, 96%, 97%, 98%, 99% or 100% identity to any of the following sequences: SEQ ID NOs: 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, or 12656-12658, or fragments or complements thereof. The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated. The present disclosure also contemplates methods of selecting an individual to undergo enhanced surveillance for the development of Barrett's esophagus with low grade dysplasia. Barrett's esophagus with high grade dysplasia or of esophageal adenocarcinoma, by obtaining a biological sample from an individual, and determining in the sample the presence of DNA methylation in at least one of any of the sequences disclosed herein. In some embodiments, the sequence is any one or more sequence selected from the group consisting of a sequence having at least 80%, 85%, 90%, 91%, 92%, 93%, 94%, 95%, 96%, 97%, 98%, 99% or 100% identity to any of the following sequences: SEQ ID NOs: 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, or 12656-12658, or fragments or complements thereof. The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated. The present disclosure also contemplates methods of determining the response of an individual with esophageal cancer to therapy by obtaining a biological sample from an individual with esophageal cancer, and determining the presence of methylation in at least one of any of the sequences disclosed herein. In some embodiments, the sequence is any one or more sequence selected from the group consisting of sequences having at least 80%, 85%, 90%, 91%, 92%, 93%, 94%, 95%, 96%, 97%, 98%, 99% or 100% identity to any of the following sequences: SEQ ID NOs: 1-856, 2569-3424, 5137-5926: 7507-7558, 7663-7714, 7819-7866, 7963-7990, 8047-8074, 8131-8156, 8209-8222, 8251-8264, 8293-8306, 8335-8348, 8405-8409, or 8420-8424, 8447-8818, 9563-9934, 10679-10972; SEQ ID NOs: 11561-11662, 11867-11968, 12173-12266: SEQ ID NOs: 12455-12466, 12491-12502, 12527-12538, 12563-12568, 12581-12586, 12599-12604, 12617-12622, 12647-12649, and 12656-12658, or fragments or complements thereof. In some implementations, an increase in levels of methylation over time is indicative of disease progression and a need for a change in therapy (such as modifying the dosing regime of an exiting therapy, or administering a new therapeutic(s) either alone or in combination with the existing therapy), and an absence of increase in levels of methylation over time or decrease in levels of methylation over time is indicative that a change in therapy is not required. The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated.

The present disclosure also contemplates method of distinguishing EAC and/or low/high grade dysplasia from BE by obtaining a biological sample from an individual, and determining in the sample the presence of DNA methylation in at least one of any of the sequences disclosed herein. In some embodiments, the sequence is any one or more sequence selected from the group consisting of sequences having at least 80%, 85%, 90%, 91%, 92%, 93%, 94%, 95%, 96%, 97%, 98%, 99% or 100% identity to any of the following sequences: SEQ ID NOs: 8447-8818, 9563-9934, 10679-10972; SEQ ID NOs: 11561-11662, 11867-11968, 12173-12266, SEQ ID NOs: 12455-12466, 12491-12502, 12527-12538, 12563-12568, 12581-12586, 12599-12604, 12617-12622, 12647-12649, and 12656-12658, or fragments or complements thereof. The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated. In certain embodiments, the absence of methylation at Up15-1, Up35-1, Up35-2, Up3, Up27, and Up10; and the absence of a somatic mutation in TP53 may be indicative of non-dysplastic Barret's esophagus. In certain embodiments, the presence of methylation at any one of Up15-1, Up35-1, Up35-2, Up3, Up27, and Up10; or the presence of a somatic mutation in TP53 may be indicative of esophageal adenocarcinoma or of Barrett's with high grade dysplasia.

The present disclosure also contemplates method of distinguishing EAC and/or low/high grade dysplasia from BE by obtaining a biological sample from an individual, and determining in the sample the presence of DNA methylation in at least one of any of the sequences disclosed herein. In some embodiments, the sequence is any one or more sequence selected from the group consisting of sequences having at least 80%, 85%, 90%, 91%, 92%, 93%, 94%, 95%, 96%, 97%, 98%, 99% or 100% identity to any of the following sequences: SEQ ID NOs: 8447-8818, 9563-9934, 10679-10972; SEQ ID NOs: 11561-11662, 11867-11968, 12173-12266, SEQ ID NOs: 12455-12466, 12491-12502, 12527-12538, 12563-12568, 12581-12586, 12599-12604, 12617-12622, 12647-12649, and 12656-12658, or fragments or complements thereof. The present disclosure further contemplates that the method may further comprise determining the status of somatic mutation(s) in TP53 in the sample. For example, a method comprising determining the status of methylation of chromosomal loci e.g., Up15-1, Up35-1, Up35-2, Up3, Up27, and Up10 in a sample; and determining the presence or absence of somatic mutation(s) in TP53 in the sample is contemplated. In certain embodiments, the absence of methylation at Up15-1, Up35-1, Up35-2, Up3, Up27, and Up10; and the absence of a somatic mutation in TP53 may be indicative of non-dysplastic Barret's esophagus. In certain embodiments, the presence of methylation at any one of Up15-1, Up35-1, Up35-2, Up3, Up27, and Up10; or the presence of a somatic mutation in TP53 may be indicative of esophageal adenocarcinoma.

The present disclosure also contemplates a method of monitoring the progression (or regression) of esophageal neoplasias over time. The method involves detecting the methylation status of one or more nucleotide sequences selected from the group consisting of sequences having at least 80%, 85%, 90%, 91%, 92%, 93%, 94%, 95%, 96%, 97%, 98%, 99% or 100% identity to any of the following sequences: SEQ ID NOs: 1-856, 2569-3424, 5137-5926; 7507-7558, 7663-7714, 7819-7866, 7963-7990, 8047-8074, 8131-8156, 8209-8222, 8251-8264, 8293-8306, 8335-8348, 8405-8409, and 8420-8424, 8447-8818, 9563-9934, 10679-10972: SEQ ID NOs: 11561-11662, 11867-11968, 12173-12266; SEQ ID NOs: 12455-12466, 12491-12502, 12527-12538, 12563-12568, 12581-12586, 12599-12604, 12617-12622, 12647-12649, and 12656-12658, or fragments or complements thereof in samples from a subject at a first time and at a later time. In certain embodiments, neoplasia regression may be indicated by the absence of methylation in the nucleotide sequence taken at a later time and the presence of methylation in the nucleotide sequence taken at the first time. In certain embodiments, neoplasia progression may be indicated by the presence of methylation in the nucleotide sequence taken at a later time and the absence of methylation in the nucleotide sequence taken at the first time. The present disclosure further contemplates that the method may further comprise determining the status of somatic mutation(s) in TP53 in the samples. In some embodiments, neoplastic regression may be indicated by the presence of methylated chromosomal loci e.g., methylation of Up15-1, Up35-1, Up35-2, Up3, Up27, and/or Up10 or the presence of a somatic mutation in TP53 in a first sample; and the absence of methylated chromosomal loci e.g., unmethylated Up15-1, Up35-1, Up35-2, Up3, Up27, and Up10, and the absence of somatic mutation(s) in TP53 in a later sample. In some embodiments, neoplastic progression may be indicated by the presence of unmethylated chromosomal loci e.g., unmethylated Up15-1, Up35-1, Up35-2, Up3, Up27, and Up10; and the absence of somatic mutation(s) in TP53 in a first sample; and the presence of methylated chromosomal loci e.g., methylated Up15-1, Up35-1, Up35-2, Up3, Up27, and/or Up10, or the presence of a somatic mutation in TP53 in a later sample.

The present disclosure also provides sequences that will hybridize under highly stringent conditions to the nucleotide sequences of any one or more of SEQ ID NOs: 1-8444 and 8447-16204, or fragments or complements thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

In other embodiments, the disclosure also provides the methylated forms of the nucleotide sequences of any one or more of SEQ ID NOs: 1-8444 and 8447-16204, or fragments thereof, wherein the cytosine bases of the CpG islands present in the sequences are methylated. In other words, the nucleotide sequences listed of any one or more of SEQ ID NOs: 1-8444 or 8447-16204 or fragments or complements thereof may be either in the methylated status (e.g., as seen in neoplasias) or in the unmethylated status (e.g., as seen in normal cells). In further embodiments, the nucleotide sequences of the disclosure can be isolated, recombinant, and/or fused with a heterologous nucleotide sequence, or in a DNA library.

In certain embodiments, the present disclosure provides bisulfite-converted nucleotide sequences, for example, bisulfite-converted sequences selected from any of the sequences disclosed herein. In some embodiments, the sequence is selected from the group consisting of sequences having at least 80%, 85%, 90%, 91%, 92%, 93%, 94%, 95%, 96%, 97%, 98%, 99% or 100% identity to any of the following sequences: SEQ ID NOs: 857-2568, 3425-5136, 5927-7506, 7559-7662, 7715-7818, 7867-7962, 7991-8046, 8075-8130, 8157-8208, 8223-8250, 8265-8292, 8307-8334, 8349-8376, 8410-8419, 8425-8434, and/or fragments thereof, and/or the reverse complements thereof. In yet other embodiments, the disclosure provides bisulfite-converted sequences selected from the group consisting of sequences having at least 80%, 85%, 90%, 91%, 92%, 93%, 94%, 95%, 96%, 97%, 98%, 99% or 100% identity to any of the following sequences: SEQ ID NOs: 8819-9562, 9935-10678, 10973-11560; 11663-11866, 11969-12172, 12267-12454; 12467-12490, 12503-12526, 12539-12562, 12569-12580, 12587-12598, 12605-12616, 12623-12634, 12650-12655, and 12659-12664, and/or fragments thereof, and/or the reverse complements thereof. In yet other embodiments, the disclosure provides bisulfite-converted sequences selected from the group consisting of sequences having at least 80%, 85%, 90%, 91%, 92%, 93%, 94%, 95%, 96%, 97%, 98%, 99% or 100% identity to any of the following sequences: SEQ ID NOs: 13145-14092, 14567-15514, 15561-15652; 15733-15892, 15973-16132, 16143-16162; 16169-16180, 16187-16198, and 16201-16204, and/or fragments thereof, and/or the reverse complements thereof.

A fragment/portion of any of the nucleotide sequences disclosed herein may be of any length, so long as the methylation status of that nucleotide sequence may be determined. In some embodiments, the nucleotide sequence is at least 10, 15, 25, 30, 40, 50, 60, 70, 80, 90, 100, 110, 120, 130, 140, 150, 160, 170, 180, 190, 200, 250, 300, 350, 400, 450, 500, 600, 700, 800, 900, 1000, 1200, 1400, 1500, 1700, or 2000 nucleotides in length. In some embodiments, the nucleotide sequence is at least 10-2000, 10-1000, 10-500, 10-200, 10-150, 10-100, 50-2000, 50-1000, 50-500, 50-200, 50-150, 50-100, 80-2000, 80-1000, 80-500, 80-150, 80-100, 100-2000, 100-1000, 100-500, 100-200, or 100-150 nucleotides in length.

Such bisulfite-converted nucleotide sequences can be used for detecting the methylation status, for example, by an MSP reaction or by direct sequencing (e.g., next generation sequencing). These bisulfite-converted sequences are also of use for designing primers for MSP reactions that specifically detect methylated or unmethylated nucleotide sequences following bisulfite conversion. In yet other embodiments, the bisulfite-converted nucleotide sequences of the disclosure also include nucleotide sequences that will hybridize under highly stringent conditions to any nucleotide sequence of any one or more of SEQ ID NOs: 1-8444 and 8447-16204, or fragments or complements thereof.

In further aspects, the application provides methods for producing such bisulfite-converted nucleotide sequences, for example, the application provides methods for treating a nucleotide sequence with a bisulfite agent such that the unmethylated cytosine bases are converted to a different nucleotide base such as a uracil.

In yet other aspects, the application provides oligonucleotide primers for amplifying a region within the nucleic acid sequence of any one or more of SEQ ID NOs: 1-8444 and 8447-16204. In certain aspects, a pair of the oligonucleotide primers can be used in a detection assay, such as the HpaII assay. In certain aspects, primers used in an MSP reaction can specifically distinguish between methylated and non-methylated DNA.

The primers of the disclosure have sufficient length and appropriate sequence so as to provide specific initiation of amplification nucleic acids. Primers of the disclosure are designed to be "substantially" complementary to each strand of the nucleic acid sequence to be amplified. In some embodiments, the primer is selected from the group consisting of sequences having 80%, 85%, 90%, 91%, 92%, 93%, 94%, 95%, 96%, 97%, 98%, 99%, or 100% identity to any of SEQ ID NOs: 8377-8404, 8435-8446, 12635-12646, and 12665-12670. In some embodiments, the primer comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 consecutive nucleotides of any of the primer sequences of SEQ ID NOs: 8377-8404, 8435-8446, 12635-12646, and 12665-12670. While exemplary primers include the sequences of any sequence having at least 80%, 85%, 90%, 91%, 92%, 93%, 94%, 95%, 96%, 97%, 98%, 99%, or 100% identity to any of SEQ ID NOs: 8377-8404, 8435-8446, 12635-12646, and 12665-12670, or fragments thereof, it is understood that any primers that hybridize with the bisulfite-converted sequence of any one or more of SEQ ID NOs: 1-8444 and 8447-16204 are included within the scope of this disclosure and is useful in the method of the disclosure for detecting methylated nucleic acid, as described. Similarly, it is understood that any primers that would serve to amplify a methylation sensitive restriction site or sites within the differentially methylated region of the informative loci of any of the sequences of SEQ ID NOs: 1-8444 or 8447-16204, or fragments or complements thereof are included within the scope of this disclosure and is useful in the method of the disclosure for detecting nucleic methylated nucleic acid, as described.

The oligonucleotide primers of the disclosure may be prepared by using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859-1862, 1981). One method of synthesizing oligonucleotides on a modified solid support is described in U.S. Pat. No. 4,458,066.

IV. Assays and Drug Screening Methodologies

In certain aspects, the application provides assays and methods using any of the informative loci, or bisulfite converted methylated or unmethylated sequences thereof, disclosed herein. In some embodiments, the informative loci comprise a sequence having at least 80%, 85%, 90%, 91%, 92%, 93%, 94%, 95%, 96%, 97%, 98%, 99%, or 100% identity to any of the sequences of SEQ ID NOs: 1-428, 2569-2996, 5137-5531, 7507-7532, 7663-7668, 7819-7842, 7963-7976, 8047-8060, 8131-8143, 8209-8222, 8293-8306, 8405-8409, 8447-8632, 9563-9748, 10679-10825, 11561-11611, 11867-11917, 12173-12219, 12455-12460, 12491-12496, 12527-12532, 12563-12568, 12599-12604, 12647-12649, 12671-12908, 14093-14329, 15515-15537, 15653-15692, 15893-15932, 16133-16137, 16163-16165, 16181-16183, 16199, 429-856, 2997-3424, 5532-5926, 7533-7558, 7689-7714, 7843-7866, 7977-7990, 8061-8074, 8144-8156, 8251-8264, 8335-8348, 8420-8424, 8633-8818, 9749-9934, 10826-10972, 11612-11662, 11918-11968, 12220-12266, 12461-12466, 12497-12502, 12533-12538, 12581-12586, 12617-12622, 12656-12658, 12909-13144, 14330-14566, 15538-15560, 15693-15732, 15933-15972, 16138-16142, 16166-16168, 16184-16186 or 16200 or any fragments or complements thereof. In some embodiments, the informative loci are used as molecular markers to distinguish between healthy cells and metaplastic cells (e.g., Barrett's esophageal cells). In some embodiments, the informative loci are used as molecular markers to distinguish between healthy cells and neoplastic cells (e.g., cancer cells). In particular embodiments, the informative loci are used as molecular markers to distinguish between healthy cells and esophageal adenocarcinoma cells. In some embodiments, the informative loci are used as molecular markers to distinguish between Barrett's esophagus cells and cancer cells. In some embodiments, the informative loci are used as molecular markers to distinguish between Barrett's esophagus cells and esophageal adenocarcinoma cells. For example, in one embodiment, the application provides methods and assays using any of the informative loci comprising a sequence having at least 80%, 85%, 90%, 91%, 92%, 93%, 94%, 95%, 96%, 97%, 98%, 99%, or 100% identity to any one or more of SEQ ID NOs: 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, OR 12656-12658, or any fragments or complements thereof as markers that distinguish between healthy cells and neoplasia cells. In other embodiments, the application provides methods and assays using the informative loci comprising a sequence having at least 80%, 85%, 90%, 91%, 92%, 93%, 94%, 95%, 96%, 97%, 98%, 99%, or 100% identity to any one or more of SEQ ID NOs: 1-856, 2569-3424, 5137-5926, 7507-7558, 7663-7714, 7819-7866, 7963-7990, 8047-8047, 8131-8156, 8209-8222, 8251-8264, 8293-8306, 8335-8348, 8405-8409, 8420-8424, 8447-8818, 9563-9934, 10679-10972, 11561-11662, 11867-11968, 12173-12266, 12455-

12466, 12491-12502, 12527-12538, 12563-12568, 12581-12586, 12599-12604, 12617-12622, 12647-12649, 12656-12658, 12671-13144, 14093-14566, 15515-15560, 15653-15732, 15893-15972, 16135-16142, 16163-16168, 16181-16186 and/or 16199-16200 or any fragments or complements thereof as markers that distinguish between healthy cells and cells derived from neoplasias of the upper gastrointestinal tract. In one aspect, a molecular marker of the invention is a differentially methylated sequence of an informative locus. In certain aspects, the application provides assays and methods using the informative loci comprising a sequence having at least 80%, 85%, 90%, 91%, 92%, 93%, 94%, 95%, 96%, 97%, 98%, 99%, or 100% identity to any one or more of SEQ ID NOs: 1-856, 2569-3424, 5137-5926, 7507-7558, 7663-7714, 7819-7866, 7963-7990, 8047-8047, 8131-8156, 8209-8222, 8251-8264, 8293-8306, 8335-8348, 8405-8409, 8420-8424, 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, 12656-12658, 12671-13144, 14093-14566, 15515-15560, 15653-15732, 15893-15972, 16135-16142, 16163-16168, 16181-16186 and/or 16199-16200 or any fragments or complements thereof in combination with the status of somatic mutation(s) in TP53 as molecular markers that distinguish between healthy cells and cancer cells. For example, in one embodiment, the application provides methods and assays using the informative loci comprising a sequence having at least 80%, 85%, 90%, 91%, 92%, 93%, 94%, 95%, 96%, 97%, 98%, 99%, or 100% identity to any one or more of SEQ ID NOs: 1-856, 2569-3424, 5137-5926, 7507-7558, 7663-7714, 7819-7866, 7963-7990, 8047-8047, 8131-8156, 8209-8222, 8251-8264, 8293-8306, 8335-8348, 8405-8409, 8420-8424, 8447-8818, 9563-9934, 10679-10972, 11561-11662, 11867-11968, 12173-12266, 12455-12466, 12491-12502, 12527-12538, 12563-12568, 12581-12586, 12599-12604, 12617-12622, 12647-12649, 12656-12658, 12671-13144, 14093-14566, 15515-15560, 15653-15732, 15893-15972, 16135-16142, 16163-16168, 16181-16186 and/or 16199-16200 or any fragments or complements thereof and the status of somatic mutation(s) in TP53 as markers that distinguish between healthy cells and neoplasia cells (e.g. cancer/esophageal adenocarcinoma cells). In other embodiments, the application provides methods and assays using the informative loci disclosed herein (e.g., chromosomal loci Up15-1, Up35-1, Up35-2, Up3, Up27, and Up10) and the status of somatic mutation(s) in TP53 as markers that distinguish between healthy cells and cells derived from neoplasias of the upper gastrointestinal tract. In one aspect, a molecular marker of the invention is a differentially methylated sequence of an informative locus.

In certain embodiments, the application provides assays for detecting differentially methylated nucleotide sequences (e.g., vimentin and/or SqBE18). Thus, a differentially methylated nucleotide sequence, in its methylated state, can serve as a target for detection using various methods described herein and the methods that are well within the purview of the skilled artisan in view of the teachings of this application.

In certain aspects, such methods for detecting methylated nucleotide sequences (e.g., vimentin and/or SqBE18) are based on treatment of genomic DNA with a chemical compound which converts non-methylated C, but not methylated C (i.e., 5 mC), to a different nucleotide base. One such compound is sodium bisulfite (also referred to simply as "bisulfite" herein), which converts C, but not 5 mC, to U. Methods for bisulfite treatment of DNA are known in the art (Herman, et al., 1996, *Proc Natl Acad Sci USA*, 93:9821-6; Herman and Baylin, 1998. *Current Protocols in Human Genetics*, N. E. A. Dracopoli, ed., John Wiley & Sons, 2:10.6.1-10.6.10: U.S. Pat. No. 5,786,146). To illustrate, when a DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a particular embodiment, the present invention provides a method of detecting U in compound-converted DNA sequences by using "methylation sensitive PCR" (MSP) (see, e.g., Herman, et al., 1996, *Proc. Natl. Acad. Sci. USA*, 93:9821-9826; U.S. Pat. Nos. 6,265,171; 6,017,704; 6,200,756). In MSP, one set of primers (i.e., comprising a forward and a reverse primer) amplifies the compound-converted template sequence if C bases in CpG dinucleotides within the DNA are methylated. This set of primers is called "methylation-specific primers." Another set of primers amplifies the compound-converted template sequence if C bases in CpG dinucleotides within the 5' flanking sequence are not methylated. This set of primers is called "unmethylation-specific primers."

In MSP, the reactions use the compound-converted DNA from a sample in a subject. In assays for methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA is not methylated, the methylation-specific primers will not amplify the compound-converted template sequence in the presence of a polymerase and an MSP product will not be produced. In some embodiments, any of the bisulfite converted methylated sequences disclosed herein is used as a marker for a particular indication.

It is often also useful to run a control reaction for the detection of unmethylated DNA. The reaction uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA is methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethylation specific signal is often of use as a control reaction, but does not in this instance imply the absence of neoplasia as indicated by the positive signal derived from reactions using the methylation specific primers. In some embodiments, any of the bisulfite converted unmethylated sequences disclosed herein are used as controls. In some embodiments, the unmethylated control sequences are any of the bisulfite converted sequences of SEQ ID NOs: 857-1284, 3425-3852, 5927-6321, 7559-7584, 7715-7740, 7867-7890, 7991-8004, 8075-8088, 8157-8169, 8223-8236, 8307-8320, 8410-8414, 8819-9004, 9935-10120, 10973-11119, 11663-11713, 11969-

12019, 12267-12313, 12467-12472, 12503-12508, or 12539-12544, 12569-12574, 12605-12610, 12650-12652, 1713-2140, 4281-4708, 6717-7111, 7611-7636, 7767-7792, 7915-7938, 8019-8032, 8103-8116, 8183-8195, 8265-8278, 8349-8362, 8425-8429, 9191-9376, 10307-10492, 11267-11413, 11765-11815, 12071-12121, 12361-12407, 12479-12484, 12515-12520, 12551-12556, 12587-12592, 12623-12628, or 12659-12661 in which every "Y" position is a "T."

Primers for a MSP reaction are derived from the compound-converted template sequence. Herein, "derived from" means that the sequences of the primers are chosen such that the primers amplify the compound-converted template sequence in a MSP reaction. Each primer comprises a single-stranded DNA fragment which is at least 8 nucleotides in length. In some embodiments, the primers are less than 50 nucleotides in length, or in some embodiments, from 15 to 35 nucleotides in length. Because the compound-converted template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted template sequence, and therefore the product of the MSP reaction, is, in some embodiments, between 20 to 3000 nucleotides in length. In other embodiments, the product of the MSP reaction is between 50 to 1000 nucleotides in length. In other embodiments, the product of the MSP reaction is between 50 to 500 nucleotides in length. In other embodiments, the product of the MSP reaction is between 80-150 nucleotides in length. In some embodiments, the product of the MSP reaction is at least 20, 30, 40, 50, 60, 70, 80, 90, 100, 110, 120, 130, 140, 150, 160, 170, 180, 190, 200, 210, 220, 230, 240 or 250 nucleotides in length. In some embodiments, the methylation-specific primers result in an MSP product of a different length than the MSP product produced by the unmethylation-specific primers.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oregon) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TaqMan probes and molecular beacons. Quantitation may be on an absolute basis, or may be relative to a constitutively methylated DNA standard, or may be relative to an unmethylated DNA standard. In one instance the ratio of methylated derived product to unmethylated derived product may be constructed.

Methods for detecting methylation of the DNA according to the present disclosure are not limited to MSP, and may cover any assay for detecting DNA methylation. Another example method of detecting methylation of the DNA is by using "methylation-sensitive" restriction endonucleases. Such methods comprise treating the genomic DNA isolated from a subject with a methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, *Cancer Res.* 57:808-11). No sodium bisulfite is used in this technique.

Yet another exemplary method of detecting methylation of the DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the DNA include the MS-SnuPE methods. This method uses compound-converted DNA as a template in a primer extension reaction wherein the primers used produce a product, dependent upon whether the compound-converted template contains CpG dinucleotides or UpG dinucleotides (see e.g., Gonzalgo, et al., 1997, *Nucleic Acids Res.*, 25:2529-31).

Another exemplary method of detecting methylation of the DNA is called COBRA (i.e., combined bisulfite restriction analysis). This method has been routinely used for DNA methylation detection and is well known in the art (see, e.g., Xiong, et al., 1997, *Nucleic Acids Res*, 25:2532-4). In this technique, methylation-sensitive restriction endonucleases recognize and cleave a specific sequence within the DNA if C bases within the recognition sequence are methylated. If C bases within the recognition sequence of the restriction endonuclease are not methylated, the DNA will not be cleaved. In some embodiments, the method utilizes methylation-sensitive restriction endonucleases.

Another exemplary method of detecting methylation of DNA requires hybridization of a compound converted DNA to arrays that include probes that hybridize to sequences derived from a methylated template.

Another exemplary method of detecting methylation of DNA includes precipitation of methylated DNA with antibodies that bind methylated DNA or with other proteins that bind methylated DNA, and then detection of DNA sequences in the precipitate. The detection of DNA could be done by PCR based methods, by hybridization to arrays, or by other methods known to those skilled in the art.

Another exemplary method of detecting methylated DNA is bisulfite sequencing that involves amplification of a target region of bisulfite converted DNA using methylation indifferent PCR primers that amplify converted DNAs derived from both methylated and unmethylated templates. The methylation indifferent primers are often designed to be both methylation indifferent and bisulfite specific, i.e. to amplify only bisulfite converted target DNAs and not to amplify non-converted target sequences. In some embodiments, the amplified DNAs then may be characterized by Next Generation Sequencing methods that allow each cytosine base in the original template to be assessed within each DNA sequence read for the presence of methylation (retention of cytosine) or the absence of methylation (conversion to thymidine). The percent of methylation at each cytosine base in the original template can then be calculated by the percent of DNA reads in which the cytosine is preserved as cytosine versus is converted to thymidine. Similarly, the percent of methylation across a region of interest can be assessed by determining a rule for assessing the region as methylated or unmethylated in an individual DNA read (i.e. determining a cutoff for methylation in the region that will categorize the region as "methylated"), and then determining the percent of DNA reads in which the region qualifies as methylated.

In certain embodiments, the disclosure provides methods that involve directly sequencing the product resulting from an MSP reaction to determine if the compound-converted template sequence contains CpG dinucleotides or UpG dinucleotides. Molecular biology techniques such as directly sequencing a PCR product are well known in the art.

In some embodiments, methylation of DNA may be measured as a percentage of total DNA. High levels of methylation may be 1-100% methylation, for example, 1%, 10%, 20%, 30%, 40%, 50%, 60%, 70%, 80%, 90%, or 100% methylation. Low levels of methylation may be 0%-0.99% methylation, for example, 0%, 0.1%, 0.5%, 0.6%, 0.7%, 0.8%, 0.9%. At least some normal tissues, for example, normal esophagus samples, may not have any detectable methylation.

The skilled artisan will appreciate that the present disclosure is based in part, on the recognition that any one of the informative loci disclosed herein may include nucleotide sequences that encode polypeptides that, for example, may function as a tumor suppressor gene. Accordingly, the application further provides methods for detecting such polypeptides in cell samples. In some embodiments, the disclosure provides detection methods by assaying such polypeptides so as to determine whether a patient has or does not have a disease condition. Further, such a disease condition may be characterized by decreased levels of such polypeptides. In certain embodiments, the disclosure provides methods for determining whether a patient is or is not likely to have cancer by detecting such polypeptides. In further embodiments, the disclosure provides methods for determining whether the patient is having a relapse or determining whether a patient's cancer is responding to treatment.

Optionally, such methods involve obtaining a quantitative measure of the protein in the sample. In view of this specification, one of skill in the art will recognize a wide range of techniques that may be employed to detect and optionally quantitate the presence of a protein. In some embodiments, a protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent. Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain embodiments, be separated into fractions such as plasma and serum.

In certain embodiments, a method of the disclosure comprises detecting the presence of an informative loci-expressed nucleic acid, such as an mRNA, in a sample. Optionally, the method involves obtaining a quantitative measure of the informative loci-expressed nucleic acid in the sample. In view of this specification, one of skill in the art will recognize a wide range of techniques that may be employed to detect and optionally quantitate the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances, detection involves an amplification as well. Northern blots, dot blots, microarrays, quantitative PCR, and quantitative RT-PCR are all well known methods for detecting a nucleic acid in a sample.

In certain embodiments, the disclosure provides nucleic acid probes that bind specifically to an informative loci nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

Immunoscintigraphy using monoclonal antibodies directed at the informative loci may be used to detect and/or diagnose a cancer. For example, monoclonal antibodies against the informative loci labeled with $^{99}$Technetium, $^{111}$Indium, $^{125}$Iodine—may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, 1-10 millicuries, or often 2-5 millicuries are administered. Thus, compositions according to the present invention useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

A variety of methods can be used to determine if TP53 contains a somatic mutation, as will be evident to the skilled artisan. In some embodiments, the TP53 gene or protein sequence is determined and any change in the determined sequence relative to the wildtype sequence is detected. In some embodiments, the TP53 gene sequence is determined by PCR, RT-PCR, Northern Blot, Southern Blot, and/or in situ hybridization. Another way to determine if TP53 contains a somatic mutation may involve the use of an antibody-based detection assay (e.g. ELISA, immunohistochemistry, and/or Western Blot). In some embodiments, the antibody-based detection assay utilizes an antibody that binds to a mutant TP53 protein with a tighter affinity than it binds to a wildtype TP53 protein. The skilled artisan will also readily appreciate methods of determining somatic mutations in TP53 based on the disclosures of U.S. Pat. Nos. 5,843,654, 5,620,848, EP0390323 and U.S. Pat. No. 5,527,676, all of which are herein incorporated by reference in their entirely.

In some embodiments, the disclosure provides for a device useful for detecting the methylation status of any of the informative loci, or fragments or complements thereof, disclosed herein. In some embodiments, the disclosure provides for a kit comprising components useful for detecting the methylation status of the informative loci, or fragments, or complements thereof, disclosed herein. In some embodiments, the kit comprises a swallowable balloon for collecting an esophageal sample from the subject. In some embodiments, the kit comprises any of the swallowable balloon devices disclosed in WO 2015/089422, which is incorporated herein in its entirety. In some embodiments, the disclosure provides for a kit comprising primers for amplifying any of the informative loci described herein, and instructions for performing any of the methods disclosed herein. In some embodiments, the kit further comprises bisulfite. In some embodiments, the kit further comprises an object suitable for collecting a sample from a subject (e.g., a brush and or balloon). In some embodiments, the disclosure provides for a kit comprising any of the therapeutic agents disclosed herein and instructions for performing any of the therapeutic methods disclosed herein.

In certain embodiments, the present disclosure provides drug screening assays for identifying test compounds which potentiate the tumor suppressor function of polypeptides encoded by sequences located in the informative loci disclosed herein. In one aspect, the assays detect test compounds which potentiate the expression level of polypeptides encoded by sequences located in the informative loci disclosed herein. In another aspect, the assays detect test compounds which inhibit the methylation of DNA. In certain embodiments, drug screening assays can be generated which detect test compounds on the basis of their ability to interfere with stability or function of polypeptides encoded by sequences located in the informative loci disclosed herein.

A variety of assay formats may be used and, in light of the present disclosure, those not expressly described herein will nevertheless be considered to be within the purview of ordinary skill in the art. Assay formats can approximate such conditions as protein expression level, methylation status of nucleotide sequences, tumor suppressing activity, and may be generated in many different forms. In many embodiments, the disclosure provides assays including both cell-free systems and cell-based assays which utilize intact cells.

Compounds to be tested can be produced, for example, by bacteria, yeast or other organisms (e.g., natural products), produced chemically (e.g., small molecules, including peptidomimetics), or produced recombinantly. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In certain embodiments, test compounds identified from these assays may be used in a therapeutic method of treating cancer.

Still another aspect of the application provides transgenic non-human animals which express a gene located within any one of the informative loci disclosed herein, or which have had one or more of such genomic gene(s) disrupted in at least one of the tissue or cell-types of the animal.

In another aspect, the application provides an animal model for cancer, which has a mis-expressed allele of a gene located within any one of the informative loci disclosed herein. Such a mouse model can then be used to study disorders arising from mis-expression of genes located within any one of the informative loci disclosed herein.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the polypeptides. For example, excision of a target sequence which interferes with the expression of a recombinant gene can be designed to activate expression of that gene. This interference with expression of the protein can result from a variety of mechanisms, such as spatial separation of the gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *Proc. Natl. Acad. Sci. USA* 89:6232-6236; Orban et al., (1992) *Proc. Natl. Acad. Sci. USA* 89:6861-6865) or the FLP recombinase system of *Saccharomyces cerevisiae* (O'Gorman et al., (1991) *Science* 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509-1514); catalyzing the excision of the target sequence when the loxP sequences are oriented as direct repeats and catalyzes inversion of the target sequence when loxP sequences are oriented as inverted repeats.

V. Subjects and Samples

In certain aspects, the invention relates to a subject suspected of having or has: a cancer, a metaplasia, or a neoplasia of the upper gastrointestinal tract (e.g., esophageal cancer). Alternatively, a subject may be undergoing routine screening and may not necessarily be suspected of having such metaplasia or neoplasia. In some embodiments, the subject is a human subject, and the neoplasia is a neoplasia of the upper gastrointestinal tract, such as the esophagus. In some embodiments, the subject is a human subject, and the metaplasia is Barrett's esophagus.

Assaying for biomarkers discussed above in a sample from subjects not known to have, e.g., a metaplasia or neoplasia of the upper or lower gastrointestinal tract can aid in diagnosis of such a metaplasia or neoplasia in the subject. To illustrate, detecting the methylation status of the nucleotide sequences by MSP can be used by itself, or in combination with detecting the somatic mutation status of TP53 or other various assays, to improve the sensitivity and/or specificity for detecting, e.g., a neoplasia of the upper or lower gastrointestinal tract. In some embodiments, such detection is made at an early stage in the development of cancer, so that treatment is more likely to be effective.

In some embodiments, an informative loci in a subject is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma) if the loci is at least 10%, 20%, 30%, 40%, 50%, 60%, 70%, 80%, 90%, or 100% methylated. In some embodiments, a DNA sample from a subject is treated with bisulfite, and the resulting bisulfite sequence corresponds to any of the nucleotide sequences disclosed herein comprising a "Y" nucleotide. In some embodiments, if at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues of the bisulfite-converted sequence have a C, the sequence is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma). In some embodiments, a DNA sample from a subject is treated with bisulfite, and the resulting bisulfite sequence corresponds to any of the nucleotide sequences disclosed herein comprising a "Y" nucleotide. In some embodiments, if at least 10%, 20%, 30%, 40%, 50%, 60%, 70%, 80%, 90%, or 100% of the Y residues of the bisulfite-converted sequence have a C, the sequence is considered "methylated" for the purposes of determining whether or not the subject is prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma). In some embodiments, a subject is determined to be prone to developing and/or has developed a metaplasia in the esophagus (e.g., Barrett's esophagus) or neoplasia (e.g., Barrett's esophagus with dysplasia such as high-grade or low-grade dysplasia) (e.g., esophageal cancer such as esophageal adenocarcinoma) if a certain number of "Y" nucleotides in a bisulfite converted sequence are cytosines. In some embodiments, the certain number is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the Y residues of the bisulfite-converted sequence. In some embodiments, the certain number is least 10%, 20%, 30%, 40%, 50%, 60%, 70%, 80%, 90%, or 100% of the Y residues of the bisulfite-converted sequence. In certain embodiments, a subject is determined to be prone to developing and/or has developed a metaplasia in the esophagus (e.g., Barrett's esophagus) or neoplasia (e.g., esophageal cancer such as esophageal adenocarcinoma) (e.g., Barrett's esophagus with dysplasia such as high-grade or low-grade dysplasia) if a certain percentage of DNA molecules from a sample from a subject are determined to be "methylated." as defined herein. In some embodiments, the certain percentage of DNA molecules is at least 10%, 20%, 30%, 40%, 50%, 60%, 70%, 80%, 90%, or 100% of the DNA molecules from the sample are determined to be "methylated." In some embodiments, the percentage of methylated DNA molecules is determined using next-generation sequencing. Exemplary cut-offs of DNA methylation and DNA molecule percentages may be found in the Examples section provided herein.

In particular embodiments, a vimentin sequence is considered "methylated" or a "methylated read" if at least 70%, 75%, 80%, 90% or 100% of the CpG cytosines in a vimentin sequence, or portion thereof, are methylated. In some embodiments, if at least 8, 9 or 10 of the "Y" nucleotides in a portion of a vimentin sequence (such as the sequence of SEQ ID NOs: 16207 and/or 16208, or a portion thereof, such as the sequence of SEQ ID NOs: 16209 and/or 16210) have a C, then the vimentin sequence is considered "methylated" or a "read." In some embodiments, the primers used to amplify the portion of the vimentin nucleic acid sequence comprise the nucleotide sequences of SEQ ID NOs: 16209 and/or 16210. In some embodiments, if at least 0.5%, 0.8%, 0.9%, 1%, 2%, 3%, 4%, 5%, 6%, 7%, 8%, or 9% of the vimentin nucleic acid sequences in a sample from a subject are considered methylated or a read, then the subject is determined to have an esophageal metaplasia and/or neoplasia. In particular embodiments, if at least 1% (e.g., at least 1.05%) of the vimentin nucleic acid sequences in a sample from a subject are considered methylated or a read, then the subject is determined to have an esophageal metaplasia and/or neoplasia.

In particular embodiments, a SqBE18 sequence is considered "methylated" or a "methylated read" if at least 65%, 70%, 75%, 80%, 90% or 100% of the CpG cytosines in a SqBE18 sequence (e.g., a nucleotide sequence at least 80%, 85%, 90%, 91%, 92%, 93%, 94%, 95%, 96%, 97%, 98%, 99% or 100% identity to the sequence of SEQ ID NO: 8220, 8262, 8304 or 8346), or a portion thereof, are methylated. In some embodiments, if at least 0.5%, 0.8%, 0.9%, 1%, 2%, 3%, 4%, 5%, 6%, 7%, 8%, or 9% of the SqBE18 nucleic acid sequences in a sample from a subject are considered methylated or a read, then the subject is determined to have an esophageal metaplasia and/or neoplasia. In particular embodiments, if at least 2%, 2.5%, or 3% (e.g., at least 3.11%) of the SqBE18 nucleic acid sequences in a brushing sample from a subject are considered methylated or a read, then the subject is determined to have an esophageal metaplasia and/or neoplasia. In particular embodiments, if at least 1% of the SqBE18 nucleic acid sequences in a balloon sample from a subject are considered methylated or a read, then the subject is determined to have an esophageal metaplasia and/or neoplasia.

In some embodiments, the disclosure provides for a method of diagnosing whether a subject has an esophageal neoplasia or metaplasia, comprising: obtaining a sample from a subject; measuring the amount of methylated cytosines in CpG dinucleotides in a vimentin nucleic acid sequence, or portion thereof, obtained from the sample; wherein if at least 65%, at least 70%, at least 75%, or preferably at least 80% of the cytosines in CpG dinucleotides in the vimentin nucleic acid sequence, or portion thereof, are methylated, than the vimentin nucleic acid sequence, or portion thereof, is considered a read; and measuring the number of reads present in the sample; wherein if at least 1% of the vimentin nucleic acid sequences, or portions thereof, in the sample are reads, than the subject is determined to have an esophageal neoplasia or metaplasia. In some embodiments, the vimentin nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the bisulfite converted vimentin nucleic acid sequence obtained from the subject. In some embodiments, the amplified portion comprises 10 CpGs. In some embodiments, the primers used to amplify the portion of the vimentin nucleic acid sequence comprise SEQ ID NOs: 16209 and 16210. In some embodiments, the amplified portion comprises the nucleotide sequence of SEQ ID NOs: 16207 and/or 16208, and the region between the amplification primers comprises the nucleotide sequences of SEQ ID Nos: 16209 and/or 162010. In some embodiments, if at least 0.5% to 5% of the vimentin nucleic acid sequences, or portions thereof, in the sample are reads, than the subject is determined to have an esophageal neoplasia or metaplasia. In some embodiments, if at least 0.5% to 3% of the vimentin nucleic acid sequences, or portions thereof, in the sample are reads, than the subject is determined to have an esophageal neoplasia or metaplasia. In some embodiments, if at least 0.5% to 1.5% of the vimentin nucleic acid sequences, or portions thereof, in the sample are reads, than the subject is determined to have an esophageal neoplasia or metaplasia. In some embodiments, if at least 0.95% to 1.16% of the vimentin nucleic acid sequences, or portions thereof, in the sample are reads, than the subject is determined to have an esophageal neoplasia or metaplasia. In some embodiments, if at least 1.02% of the vimentin nucleic acid sequences, or portions thereof, in the sample are reads, than the subject is determined to have an esophageal neoplasia or metaplasia. In some embodiments, if at least 3% of the vimentin nucleic acid sequences, or portions thereof, in the sample are reads, than the subject is determined to have an esophageal neoplasia or metaplasia. In some embodiments, if at least 5% of the vimentin nucleic acid sequences, or portions thereof, in the sample are reads, than the subject is determined to have an esophageal neoplasia or metaplasia. In some embodiments, if the sample is obtained from a brushing, and if at least 0.5% to 1.5% of the vimentin nucleic acid sequences, or portions thereof, in the sample are reads, than the subject is determined to have an esophageal neoplasia or metaplasia. In some embodiments, if the sample is obtained from a brushing, and if at least 1.05% of the vimentin nucleic acid sequences, or portions thereof, in the sample are reads, than the subject is determined to have an esophageal neoplasia or metaplasia. In some embodiments, if the sample is obtained from a balloon, and if at least 0.5% to 1.5% of the vimentin nucleic acid sequences, or portions thereof, in the sample are reads, than the subject is determined to have an esophageal neoplasia or metaplasia. In some embodiments, if the sample is obtained from a balloon, and if at least 0.95% to 1.16% of the vimentin nucleic acid sequences, or portions thereof, in the sample are reads, than the subject is determined to have an esophageal neoplasia or metaplasia. In some embodiments, if the sample is obtained from a balloon, and if at least 1% of the vimentin nucleic acid sequences, or portions thereof, in the sample are reads, than the subject is determined to have an esophageal neoplasia or metaplasia. In some embodiments, if the subject is determined to have an esophageal neoplasia or metaplasia, then the subject may be administered any of cryotherapy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the disclosure provides for a method of diagnosing whether a subject has an esophageal neoplasia or metaplasia, comprising: obtaining a sample from a subject; measuring the amount of methylated cytosines in CpG dinucleotides in a SqBE18 nucleic acid sequence, or portion thereof, obtained from the sample; wherein if at least 65%, at least 70%, or at least 75% (e.g., at least 71% or at least 76%) of the cytosines in CpG dinucleotides in the SqBE18 nucleic acid sequence, or portion thereof, are methylated, than the SqBE18 nucleic acid sequence, or portion thereof, is considered a read, and measuring the number of reads present in the sample; wherein if at least 0.5%, at least 1%, at least 2%, or at least 3% (e.g. least 3.11%) of the SqBE18 nucleic acid sequences, or portions thereof, in the sample are reads, than the subject is determined to have an esophageal neoplasia or metaplasia. In some embodiments, the SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the bisulfite converted SqBE18 nucleic acid sequence obtained from the subject. In some embodiments, if at least 0.5% to 50% of the SqBE18 nucleic acid sequences, or portions thereof, in the sample are reads, than the subject is determined to have an esophageal neoplasia or metaplasia. In some embodiments, if at least 0.5% to 3.5% of the SqBE18 nucleic acid sequences, or portions thereof, in the sample are reads, than the subject is determined to have an esophageal neoplasia or metaplasia. In some embodiments, if at least 1% to 3.11% of the SqBE18 nucleic acid sequences, or portions thereof, in the sample are reads, than the subject is determined to have an esophageal neoplasia or metaplasia. In some embodiments, if at least 0.76% to 1.06% of the SqBE18 nucleic acid sequences, or portions thereof, in the sample are reads, than the subject is determined to have an esophageal neoplasia or metaplasia. In some embodiments, if at least 3.11% of the SqBE18 nucleic acid sequences, or portions thereof, in the sample are reads, than the subject is determined to have an esophageal neoplasia or metaplasia. In some embodiments, if at least 0.1% of the SqBE18 nucleic acid sequences, or portions thereof, in the sample are reads, than the subject is determined to have an esophageal neoplasia or metaplasia. In some embodiments, if at least 1% of the SqBE18 nucleic acid sequences, or portions thereof, in the sample are reads, than the subject is determined to have an esophageal neoplasia or metaplasia. In some embodiments, if the sample is obtained from a brushing, and if at least 2% to 3.11% of the SqBE18 nucleic acid sequences, or portions thereof, in the sample are reads, than the subject is determined to have an esophageal neoplasia or metaplasia. In some embodiments, if the sample is obtained from a brushing, and if at least 3.11% of the SqBE18 nucleic acid sequences, or portions thereof, in the sample are reads, than the subject is determined to have an esophageal neoplasia or metaplasia. In some embodiments, if the sample is obtained from a balloon, and if at least 0.5% to 1.5% of the SqBE18 nucleic acid sequences, or portions thereof, in the sample are reads, than the subject is determined to have an esophageal neoplasia or metaplasia. In some embodiments, if the sample is obtained from a balloon, and if at least 0.76% to 1.06% of the SqBE18 nucleic acid sequences, or portions thereof, in the sample are reads, than the subject is determined to have an esophageal neoplasia or metaplasia. In some embodiments, if the sample is obtained from a balloon, and if at least 1% of the SqBE18 nucleic acid sequences, or portions thereof, in the sample are reads, than the subject is determined to have an esophageal neoplasia or metaplasia. In some embodiments, if the subject is determined to have an esophageal neoplasia or metaplasia, then the subject may be administered any of cryotherapy, photodynamic therapy (PDT); radiofrequency ablation (RFA); laser ablation; argon plasma coagulation (APC); electrocoagulation (electrofulguration); esophageal stent, surgery, and/or a therapeutic agent.

In some embodiments, the disclosure provides for a method of diagnosing whether a subject has an esophageal neoplasia or metaplasia, comprising: obtaining a sample from a subject; measuring the amount of methylated cytosines in CpG dinucleotides in a vimentin nucleic acid sequence and in a SqBE18 nucleic acid sequence, or portions thereof, obtained from the sample; wherein if at least 65%, at least 70%, at least 75%, or preferably at least 80% of the cytosines in CpG dinucleotides in the vimentin nucleic acid sequence, or portion thereof, are methylated, than the vimentin nucleic acid sequence, or portion thereof, is considered a read for VIM (vimentin); wherein if at least 65%, at least 70%, or at least 75% (e.g., at least 71% or at least 76%) of the cytosines in CpG dinucleotides in the SqBE18 nucleic acid sequence, or portion thereof, are methylated, than the SqBE18 nucleic acid sequence, or portion thereof, is considered a read for SqBE18; and measuring the number of VIM and SqBE18 reads present in the sample; wherein if at least 1% of the vimentin nucleic acid sequences, or portions thereof, in the sample are VIM reads and if at least 0.5%, at least 1%° at least 2%, or at least 3% (e.g. least 3.11%) of the SqBE18 nucleic acid sequences, or portions thereof, in the sample are SqBE18 reads, than the subject is determined to have an esophageal neoplasia or metaplasia. In some embodiments, the vimentin or SqBE18 nucleic acid sequences from the sample are treated with bisulfite. In some embodiments, the sequence of the bisulfite converted nucleic acid sequences is determined by next-generation sequencing. In some embodiments, the level of methylated cytosines is determined in an amplified portion of the bisulfite converted vimentin or SqBE18 nucleic acid sequence obtained from the subject. In some embodiments, the amplified vimentin portion comprises 10 CpGs. In some embodiments, the amplified SqBE18 portion comprises 21 CpGs. In some embodiments, the primers used to amplify the portion of the bisulfite converted vimentin nucleic acid sequence comprise SEQ ID NOs: 16209 and 16210. In some embodiments, the amplified portion comprises the nucleotide sequence of SEQ ID NOs: 16207 and/or 16208, and the region between the amplification primers comprises the nucleotide sequences of SEQ ID Nos: 16209 and/or 16210. In some embodiments, the primers used to amplify the portion of the bisulfite converted SqBE18 nucleic acid sequence comprise SEQ ID NOs: 8388 and 8402. In some embodiments, the amplified portion comprises the nucleotide sequence of SEQ ID NOs: 8318 and/or 8360, or fragments and/or reverse complements thereof. In some embodiments, the amplified portion comprises the nucleotide sequences of SEQ ID NOs: 8332 and/or 8374, or fragments and/or reverse complements thereof, which may be generated from fully methylated parental templates. In some embodiments, if at least 0.5% to 5% of the vimentin nucleic acid sequences, or portions thereof, in the sample are VIM reads, and if at least 0.50% to 5% of the SqBE18 nucleic acid sequences, or portions thereof, in the sample are SqBE18 reads, than the subject is determined to have an esophageal neoplasia or metaplasia. In some embodiments, if at least 0.5% to 3% of the vimentin nucleic acid sequences, or portions thereof, in the sample are VIM reads, and if at least 0.5% to 3.5% of the SqBE18 nucleic acid sequences, or portions thereof, in the sample are SqBE18 reads, than the subject is determined to have an esophageal neoplasia or metaplasia. In some embodiments, if at least 0.5% to 1.5% of the vimentin nucleic acid sequences, or portions thereof, in the sample are VIM reads, and if at least 1% to 3.11% of the SqBE18 nucleic acid sequences, or portions thereof, in the sample are SqBE18 reads, than the subject is determined to have an esophageal neoplasia or metaplasia. In some embodiments, if at least 1% of the vimentin nucleic acid sequences, or portions thereof, in the sample are VIM reads, and if at least 1% of the SqBE18 nucleic acid sequences, or portions thereof, in the sample are SqBE18 reads, than the subject is determined to have an esophageal neoplasia or metaplasia. In some embodiments, if at least 1.05% of the vimentin nucleic acid sequences, or portions thereof, in the sample are VIM reads, and if at least 3.11% of the SqBE18 nucleic acid sequences, or portions thereof, in the sample are SqBE18 reads, than the subject is determined to have an esophageal neoplasia or metaplasia. In some embodiments, if the sample is obtained from a brushing, and if at least 0.5% to 1.5% of the vimentin nucleic acid sequences, or portions thereof, in the sample are VIM reads, and if at least 2% to 3.11% of the SqBE18 nucleic acid sequences, or portions thereof, in the sample are SqBE18 reads, than the subject is determined to have an esophageal neoplasia or metaplasia. In some embodiments, if the sample is obtained from a brushing, and if at least 1.05% of the vimentin nucleic acid sequences, or portions thereof, in the sample are VIM reads, and if at least 3.11% of the SqBE18 nucleic acid sequences, or portions thereof, in the sample are SqBE18 reads, than the subject is determined to have an esophageal neoplasia or metaplasia. In some embodiments, if the sample is obtained using a balloon, and if at least 0.5% to 1.5% of the vimentin nucleic acid sequences, or portions thereof, in the sample are VIM reads, and if at least 0.5% to 1.5% of the SqBE18 nucleic acid sequences, or portions thereof, in the sample are SqBE18 reads, than the subject is determined to have an esophageal neoplasia or metaplasia. In some embodiments, if the sample is obtained using a balloon, and if at least 0.95% to 1.16% of the vimentin nucleic acid sequences, or portions thereof, in the sample are reads, and if at least 0.76% to 1.06% of the SqBE18 nucleic acid sequences, or portions thereof, in the sample are SqBE18 reads, than the subject is determined to have an esophageal neoplasia or metaplasia. In some embodiments, if the sample is obtained from a balloon, and if at least 1% of the vimentin nucleic acid sequences, or portions thereof, in the sample are reads, and if at least 1% of the SqBE18 nucleic acid sequences, or portions thereof, in the sample are SqBE18 reads, than the subject is determined to have an esophageal neoplasia or metaplasia. In some embodiments, if the subject is determined to have an esophageal neoplasia or metaplasia, then the subject may be administered any of cryotherapy, photodynamic therapy (PDT); radiofrequency ablation (RFA); laser ablation; argon plasma coagulation (APC); electrocoagulation (electrofulguration); esophageal stent, surgery, and/or a therapeutic agent.

In addition to diagnosis, assaying of a marker in a sample from a subject not known to have, e.g., a metaplasia or neoplasia of the upper gastrointestinal tract, can be prognostic for the subject (i.e., indicating the probable course of the disease). To illustrate, subjects having a predisposition to develop a metaplasia or neoplasia of the upper gastrointestinal tract may possess methylated nucleotide sequences. Assaying of methylated informative loci (e.g., vimentin and/or SqBE18) in a sample from subjects either by itself, or in combination with assaying for somatic mutation(s) in TP53, can also be used to select a particular therapy or therapies which are particularly effective against, e.g., a neoplasia or metaplasia of the upper gastrointestinal tract in the subject, or to exclude therapies that are not likely to be effective.

Assaying of methylated informative loci (e.g., vimentin and/or SqBE18) in samples from subjects that are known to have, or to have had, a cancer is also useful. For example, the present methods can be used to identify whether therapy is effective or not for certain subjects. One or more samples are taken from the same subject prior to and following therapy, and assayed for any one or more of the informative loci markers either by itself or themselves, or in combination with assaying for somatic mutation(s) in TP53. A finding that an informative locus is methylated in the sample taken prior to therapy and absent (or at a lower level) after therapy may indicate that the therapy is effective and need not be altered. In those cases where the informative locus is methylated in the sample taken before therapy and in the sample taken after therapy, it may be desirable to alter the therapy to increase the likelihood that the cancer will be reduced in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of a cancer associated with silencing of genes located in the informative loci disclosed herein. For subjects in whom a cancer is progressing, there can be no DNA methylation in some or all samples when the first sample is taken and then appear in one or more samples when the second sample is taken. For subjects in which cancer is regressing, DNA methylation may be present in one or a number of samples when the first sample is taken and then be absent in some or all of these samples when the second sample is taken.

Samples for use with the methods described herein may be essentially any biological material of interest, e.g., a collection of cells taken from a subject. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immuno-compromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc. In some embodiments, a sample is obtained by means of a cytology brushing and/or a balloon. In some embodiments, the sample is obtained from a subject's gastroesophageal junction.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In some embodiments, the bodily fluid may be derived from the stomach, for example, gastric secretions, acid reflux, or vomit. In other embodiments, the bodily fluid may be a fluid secreted by the pancreas or bladder. In other embodiments, the body fluid may be saliva, spit, or an esophageal washing. In certain embodiments, a tissue sample is a biopsy taken from the mucosa of the gastrointestinal tract. In other embodiments, a tissue sample is the brushings from, e.g., the esophagus of a subject.

A subject is in some embodiments a human subject, but it is expected that the molecular markers disclosed herein, and particularly their homologs from other animals, are of similar utility in other animals. In certain embodiments, it may be possible to detect a biomarker described herein (e.g., DNA methylation or protein expression level) directly in an organism without obtaining a separate portion of biological material. In such instances, the term "sample" is intended to encompass that portion of biological material that is contacted with a reagent or device involved in the detection process.

In certain embodiments, DNA which is used as the template is obtained from a bodily fluid sample. Examples of bodily fluids are blood, saliva, spit or an esophageal washing. Other body fluids can also be used. Because they can be easily obtained from a subject and can be used to screen for multiple diseases, blood or blood-derived fractions are especially useful. Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

In some embodiments, DNA is isolated from samples. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

VI. Therapeutic Methods

In some embodiments, the disclosure provides for a method of determining whether a subject has any one or more of the methylated informative loci disclosed herein (e.g., vimentin and/or SqBE18) that are indicative of the presence of a metaplasia in the esophagus (e.g., Barrett's esophagus), wherein if the subject is determined to have a metaplasia in the esophagus (e.g., Barrett's esophagus), the subject is treated with an agent that treats the metaplasia in the esophagus (e.g., Barrett's esophagus). In some embodiments, the disclosure provides for a method of treating a subject determined to have a metaplasia in the esophagus (e.g., Barrett's esophagus). In some embodiments, the treatment of a metaplasia in the esophagus (e.g, Barrett's esophagus) encompasses administration of any one or more of the following compounds: proton pump inhibitors (PPIs) such as omeprazole (Prilosec, Zegerid), lansoprazole (Prevacid), pantoprazole (Protonix), rabeprazole (AcipHex), esomeprazole (Nexium), dexlansoprazole (Dexilant). Histamine H2 receptor blocking agents such as cimetidine (Tagamet), ranitidine (Zantac), famotidine (Pepcid) and nizatidine (Axid). Tums, Rolaids, or other quick-acting reflux medications. Prokinetic agents, or drugs that help move food through the gastrointestinal tract more quickly, offer an attractive alternative either alone or in combination with acid inhibition. In some embodiments, the treatment of a metaplasia in the esophagus (e.g., Barrett's esophagus) is endoscopic mucosal resection (EMR); photodynamic therapy (PDT), radiofrequency ablation (RFA); argon plasma coagulation (APC); cryotherapy, and/or surgery (e.g. esophagectomy, anti-reflux surgery).

In some embodiments, the disclosure provides for a method of determining whether a subject has any one or more of the methylated informative loci disclosed herein that are indicative of esophageal neoplasia (e.g., esophageal cancer), wherein if the subject is determined to have an esophageal neoplasia (e.g., esophageal cancer), the subject is treated with an agent that treats the esophageal neoplasia (e.g., esophageal cancer). In some embodiments, the disclosure provides for a method of determining whether a subject has any one or more of the methylated informative loci disclosed herein in combination with any of the TP53 somatic mutations disclosed herein that are indicative of esophageal neoplasia (e.g., esophageal cancer), wherein if the subject is determined to have an esophageal neoplasia (e.g., esophageal cancer), the subject is treated with an agent that treats the esophageal neoplasia (e.g., esophageal cancer). In some embodiments, the disclosure provides for a method of treating a subject determined to have esophageal neoplasia (e.g., esophageal cancer). In some embodiments, the esophageal neoplasia is Barrett's esophagus with low grade dysplasia, Barrett's esophagus with high grade dysplasia (HGD) and/or esophageal adenocarcinoma (EAC). In some embodiments, the treatment of esophageal neoplasia (e.g., esophageal cancer) encompasses surgery (e.g. esophagectomy), radiation therapy, chemoradiation therapy and/or chemotherapy. In some embodiments, the treatment of esophageal neoplasia (e.g., esophageal cancer) encompasses administering one or more chemotherapeutic agent, such as any one or more therapeutic agent selected from the group consisting of: carboplatin and paclitaxel (Taxol®) (which may be combined with radiation); cisplatin and 5-fluorouracil (5-FU) (often combined with radiation): ECF: epirubicine (Ellence®), cisplatin, and 5-FU (especially for gastroesophageal junction tumors); DCF: docetaxel (Taxoteret®), cisplatin, and 5-FU; Cisplatin with capecitabine (Xeloda®); oxaliplatin and either 5-FU or capecitabine: doxorubicin (Adriamycin®), bleomycin, mitomycin, methotrexate, vinorelbine (Navelbine®), topotecan, and irinotecan (Camptosar®). In some embodiments, for some esophagus cancers that overexpress the HER2 protein on the surface of their cells, chemotherapy may be used along with the targeted drug trastuzumab. Ramucirumab may be used to treat cancers that start at the gastroesophageal (GE) junction when they are advanced. In some embodiments, the treatment encompasses endoscopic treatments, such as endoscopic mucosal resection (EMR) followed by treatment with proton pump inhibitors, photodynamic therapy (PDT); radiofrequency ablation (RFA); laser ablation; argon plasma coagulation (APC); electrocoagulation (electrofulguration); or esophageal stent.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

Treating a metaplasia (e.g., Barrett's esophagus) and/or a neoplasia (e.g., esophageal cancer) in a subject refers to improving (improving the subject's condition), alleviating, delaying or slowing progression or onset, decreasing the severity of one or more symptoms associated with a metaplasia (e.g., Barrett's esophagus) and/or a neoplasia (e.g., esophageal cancer). For example, treating a metaplasia or neoplasia includes any one or more of: reducing growth, proliferation and/or survival of metaplastic/neoplastic cells, killing metaplastic/neoplastic cells (e.g., by necrosis, apoptosis or autophagy), decreasing metaplasia/neoplasia size, decreasing rate of metaplasia/neoplasia size increase, halting increase in metaplasia/neoplasia size, improving ability to swallow, decreasing internal bleeding, decreasing incidence of vomiting, reducing fatigue, decreasing the number of metastases, decreasing pain, increasing survival, and increasing progression free survival.

EXEMPLIFICATION

The invention now being generally described, it will be more readily understood by reference to the following examples, which are included merely for purposes of illustration of certain aspects and embodiments of the present invention, and are not intended to limit the invention.

Example 1: Identification of Esophageal Cancer Informative Loci

Methylated informative loci were initially identified using the technique of reduced representation bisulfite sequencing (RRBS) in a discovery set of 23 paired biopsies of normal squamous esophagus and matched esophageal adenocarcinomas, along with biopsies of 8 Barrett's esophagus tissue, and along with brushings of 8 Barrett's esophagus tissues (one BE brushing case also having a matched biopsy).

Discovery data were initially analyzed for each individual CpG residue in the RRBS data set. Individual CpGs were considered methylated in EAC if they showed methylation in less than 10% of DNA sequence reads in all of the informative squamous samples, where at least 4 squamous samples were informative, where an informative sample had equal to or greater than 20 reads covering the CpG, and if 8 or more of the informative EAC samples demonstrated percent methylation at a level that was at least 20 percentage points greater than the methylation level of the most methylated normal squamous sample. CpGs were similarly defined as methylated in Barrett's esophagus if they showed methylation of less than 10% of DNA sequence reads of all informative squamous samples, where an informative sample had equal to or greater than 20 reads covering the CpG, and if 3 or more of the informative BE samples demonstrated percent methylation at a level that was at least 20 percentage points greater than the methylation level of the most methylated normal squamous sample. CpGs meeting criteria for methylation in both EACs and BE were defined as methylated in both EAC and BE. Such methylated CpGs were then aggregated into patches by grouping together methylated CpGs that were within 200 bp of one another. Patches may consist of 1 CpG up to any number of CpGs that meet the above criteria.

The names assigned to 428 genomic patches defined as methylated in both EAC and BE by the criteria above were recorded, and the sequences of these loci correspond to SEQ ID NOs: 1-856. The genomic coordinates of the genomic patches defined as methylated by the above criteria were also recorded. The genomic sequences of these patches on the respective genomic (+) and (−) strands were determined and recorded. (Upper and lower case designations were used according to those of the UCSC browser, where lower case sequences are lower complexity DNA sequences). The bisulfite converted sequences of these corresponding patches (i.e. the bisulfite converted sequence of the (+) strand and the bisulfite converted sequence of the (−) strand) were determined and recorded (see sequences of SEQ ID NOs: 857-1281 and 1713-2140 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding patches (i.e. in which all Y bases in every bisulfite converted sequence are retained as a C), corresponding to the (+) strand the (−) strand were determined and recorded (see sequences of SEQ ID NOs: 1285-1712 and 2141-2568 for the bisulfite converted sequences of the fully methylated form of the (+) and (−) strands respectively of the corresponding patches). The reverse complements of the bisulfite converted methylated (+) stand and (−) stand sequences will be obvious to one of ordinary skill in the art and are also included by implication in this disclosure.

Patches were expanded by 100 base pairs on either side so as to accommodate either the design of amplification primers or to enclude additional presumptively methylated bases. The sequences of these expanded patches correspond to SEQ ID NOs: 2569-3424 and their genomic coordinates were also recorded. The genomic sequences of these expanded patches on the respective genomic (+) and (−) strands were determined and recorded. (Upper and lower case designations were used according to those of the UCSC browser, where lower case sequences are lower complexity DNA sequences). The bisulfite converted sequences of these corresponding expanded patches (i.e. the bisulfite converted sequence of the (+) strand and the bisulfite converted sequence of the (−) strand) were determined and recorded (see sequence of SEQ ID NOs: 3425-3852 and 4281-4708 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding expanded patches (i.e. in which all Y bases in every bisulfite converted sequence are retained as a C), corresponding to the (+) strand the (−) strand were determined and recorded (see sequences of SEQ ID NOs: 3853-4280 and 4789-5136 for the bisulfite converted sequences of the fully methylated form of the (+) and (−) strands respectively of the corresponding expanded patches). The reverse complements of the bisulfite converted methylated (+) stand and (−) stand sequences will be obvious to one of ordinary skill in the art and are also included by implication in this disclosure.

CpG islands overlapping patches that may contain additional CpGs that are methylated coordinately with patches were also defined. The sequences of these CpG islands correspond to SEQ ID NOs: 5137-5926. The genomic coordinates of the CpG islands were also recorded. The genomic sequences of these expanded patches on the respective genomic (+) and (−) strands were determined and recorded. (Upper and lower case designations were used according to those of the UCSC browser, where lower case sequences are lower complexity DNA sequences). The bisulfite converted sequences of these corresponding CpG islands (i.e. the bisulfite converted sequence of the (+) strand and the bisulfite converted sequence of the (−) strand) were determined and recorded (see sequences of SEQ ID NOs: 5927-6321 and 6717-7111 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding CpG islands (i.e. in which all Y bases in every bisulfite converted sequence are retained as a C), corresponding to the (+) strand the (−) strand were determined and recorded (see sequences of SEQ ID NOs: 6322-6716 and 7112-7506 for the bisulfite converted sequences of the fully methylated form of the (+) and (−) strands respectively of the corresponding CpG islands). The reverse complements of the bisulfite converted methylated (+) stand and (−) stand sequences will be obvious to one of ordinary skill in the art and are also included by implication in this disclosure.

Regions of Interest (ROI) were defined that provided preferred regions for design of PCR amplicons that would encompass preferred patches. The genomic coordinates of the ROI were also recorded. The sequences of the (+) strands of the Regions of Interest correspond to SEQ ID NOs: 8209-8222, and the sequences of the (−) strands Regions of Interest correspond to SEQ ID NOs: 8251-8261. (Upper and lower case designations were used according to those of the UCSC browser, where lower case sequences are lower complexity DNA sequences). The bisulfite converted sequences of these corresponding Regions of Interest (i.e. the bisulfite converted sequence of the (+) strand and the bisulfite converted sequence of the (−) strand) were determined and recorded (see sequences of SEQ ID NOs: 8223-8236 and 8265-8278 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the Regions of Interest (i.e. in which all Y bases in every bisulfite converted sequence are retained as a C), corresponding to the (+) strand the (−) strand were determined and recorded (see sequences of SEQ ID NOs: 8237-8250 and 8279-8292 for the bisulfite converted sequences of the fully methylated form of the (+) and (−) strands respectively of the corresponding Regions of Interest). The reverse complements of the bisulfite converted methylated (+) stand and (−) stand sequences will be obvious to one of ordinary skill in the art and are also included by implication in this disclosure.

Specific PCR Amplicons were defined within the Regions of Interest (ROI). The genomic coordinates of the Amplicons were recorded. The sequences of the (+) strands of the Amplicons correspond to SEQ ID NOs: 8293-8306 and 8405-8409, and the sequences of the (−) strands of the Amplicons correspond to SEQ ID NOs: 8335-8348 and 8420-8424. (Upper and lower case designations were used according to those of the UCSC browser, where lower case sequences are lower complexity DNA sequences). The bisulfite converted sequences of these Amplicons (i.e. the bisulfite converted sequence of the (+) strand and the bisulfite converted sequence of the (−) strand) were determined and recorded (see sequences of SEQ ID NOs: 8307-8320 and 8410-8414 for the bisulfite converted sequences of the (+) strands and see sequences of SEQ ID NOs: 8349-8362 and 8425-8429 and for the bisulfite converted sequences of the (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the Amplicons (i.e. in which all Y bases in every bisulfite converted sequence are retained as a C), corresponding to the (+) strand the (−) strand were determined and recorded (see sequences of SEQ ID NOs: 8321-8334 and 8415-8419 for the bisulfite converted sequences of the fully methylated form of the (+) strands and see sequences of SEQ ID NOs: 8363-8376 and 8430-8434 for the bisulfite converted sequences of the fully methylated form of the (−) strands). The reverse complements of the bisulfite converted methylated (+) stand and (−) stand sequences will be obvious to one of ordinary skill in the art and are also included by implication in this disclosure. Sequences of PCR primers used in amplification of the Amplicons are provided as SEQ ID NOs: 8377-8404 and 8435-8444.

Confirmatory analysis of candidate loci was then done using bisulfite sequencing of candidate loci that were amplified using bisulfite specific but methylation independent amplification primers. This employed a new sample set of biopsies from: 23 EACs, 8 HGD, 15 non-dysplastic BE from individuals without known higher grade lesions. In addition, biopsies were obtained from 5 cases of BE adjacent to HGD, and from 11 cases of BE adjacent to an EAC. These were not included in analyses of non-dysplastic BE. In addition biopsies were obtained from 33 normal squamous mucosa samples.

Table 1 describes the performance in the confirmatory sample set using bisulfite sequencing analysis of amplicons of select loci having strong performance characteristics and identified in the studies discussed above. In Table 1, columns C-S disclose the performance of the select amplicons. For each DNA sequence read across each amplicon, the number of CpGs that were methylated between the amplification primers was counted, and the read was classified as methylated or unmethyled using cutoffs for a required number of methylated CpGs on the amplicon. Table 1, row 3 lists the number of CpGs between the amplification primers for each of the amplicons. Table 1, row 4 lists the number of CpGs that need to be methylated on an individual read to count that read as methylated (e.g. for SqBE 2 there are 16 CpG residues between the primers, and 14+(meaning >=14) CpGs must be methylated on a read to score it as methylated. Table 1, rows 6, 7, and 8 record the sensitivity for detecting esophageal adenocarcinomas (EACs) (row 6), high grade dysplasias (HGD) (row 7) and non-dysplastic Barrett's esophagus (non-dysplastic BE) (row 8), using criteria in which a sample was detected if it demonstrated methylation in greater than 10% (0.1) of all DNA reads. Table 1, row 9 records the specificity of each amplicon for not detecting normal squamous mucosa again using criteria in which a sample was detected if it demonstrated methylation in greater than 10% (0.1) of all DNA reads. Table 1, row 11 records the specificity of each amplicon for not detecting normal squamous mucosa now using criteria in which a sample was detected if it demonstrated methylation in greater than 1% (0.01) of all DNA reads. As a comparator, Table 1, column B provides the same data for detecting methylation in the Vimentin (VIM) locus amplified using primers disclosed in Li et al. (Li M. et al. (2009) Sensitive digital quantification of DNA methylation in clinical samples. Nat Biotechnol 27(9):858-863). These primers correspond to SEQ ID NOs: 8445-8446. The amplicon amplified using these primers is derived from the parental (−) strand and is as follows:

```
Vimentin amplicon (-) strand (SEQ ID NO: 16208):
GtTGtttAGGtTGTAGGTGYGGGTGGAYGTAGTtAYGTAGtTtYGGtT GGAGtTYGGtYGGtTYGYGGTGttYGGGtYGtYGAAtATttTGYGGTA

GGAGGAYGAG
```

The reverse complement of SEQ ID NO: 16208 is also generated.

The region of this amplicon lying between the amplification primers, in which methylation is analyzed, is as follows:

```
Vimentin amplicon (-) strand (SEQ ID NO: 16212):
GGAYGTAGTtAYGTAGtTtYGGtTGGAGtTYGGtYGGtTYGYGGTGtt YGGGtYGtYGA
```

The reverse complement of SEQ ID NO: 16212 is also generated and analyzed.

For reference, the bisulfite converted sequence that would be derived from amplifying the corresponding bisulfite converted region derived from the Vimentin (+) strand would be.

```
Vimentin amplicon (+) strand (SEQ ID NO: 16207):
tTYGTttTttTAtYGtAGGATGTTYGGYGGttYGGGtAtYGYGAGtYG GtYGAGtTttAGtYGGAGtTAYGTGAtTAYGTttAttYGtAttTAtAG ttTGGGtAGt
```

Along with the reverse complement of SEQ ID NO: 16207. And the corresponding portion of SEQ ID NO: 16211 that falls between the primers used to amplify the Vimentin (−) strand amplicon is:

```
Vimentin amplicon (+) strand (SEQ ID NO: 16211):
TYGGYGGttYGGGtAtYGYGAGtYGGtYGAGtTttAGtYGGAGtTAYG TGAtTAYGTtt
```

Along with reverse complement of SEQ ID NO: 16211.

Amplicons (and patches) need not be used individually, but can be combined into panels for detection of esophageal neoplasia. Examples of such panels, and their associated performance statistics, are provided in Table 1, columns T through AG that provide the markers in the panel and the sensitivity and specificity resulting from the marker combination (when the combination is positive if any member of the combination is positive).

The sensitivity for detection of EAC (100%), HGD (88%), and BE (100%) is the same among the combinations shown of: all amplicons, 17 amplicons, 15 amplicons, 4 amplicons, three of four combinations of 3 amplicons (columns Y, Z, AA), and for one combination of 2 amplicons (column AF). Specificity for not detecting normal squamous (97%), at a detection cutoff of 10% of reads being methylated, is the same for all combinations shown of: 15 amplicons, 4 amplicons, 3 amplicons, or 2 amplicons. When specificity is determined using a cutoff of 1% of reads being methylated, then among amplicons with the highest sensitivity, the highest specificity is 94%, demonstrated by the combination of 3 amplicons of Table 1, column Z, followed by 91% specificity demonstrated by combinations shown of: 4 amplicons, two combinations of three amplicons, and one combination of 2 amplicons.

TABLE 1A

| A | B VIM | C SqBE 2 | D SqBE 5 | E SqBE 7 | F SqBE 9 | G SqBE 10 | H SqBE 11-1 | I SqBE 11-2 | J SqBE 13 | K SqBE 14-2 | L SqBE 15 | M SqBE 16-1 | N SqBE 16-2 | O SqBE 17-1 | P SqBE 18 | Q SqBE 22-1 | R SqBE 22-2 | S SqBE 23 |
|---|---|---|---|---|---|---|---|---|---|---|---|---|---|---|---|---|---|---|
| Number of CpGs in amplicon analysis | 10 | 16 | 15 | 27 | 31 | 10 | 17 | 10 | 19 | 22 | 11 | 26 | 26 | 22 | 21 | 9 | 20 | 10 |
| Number of CpGs used for methylation call Cut-off = 0.1 | 5+ | 14+ | 8+ | 10+ | 16+ | 5+ | 8+ | 5+ | 10+ | 14+ | 5+ | 9+ | 8+ | 12+ | 9+ | 6+ | 11+ | 6+ |
| Sensitivity EAC | 70% | 74% | 100% | 40% | 65% | 96% | 4% | 87% | 38% | 64% | 74% | 52% | 9% | 74% | 91% | 87% | 82% | 59% |
| Sensitivity HGD | 63% | 50% | 100% | 57% | 50% | 75% | 0% | 63% | 33% | 43% | 63% | 50% | 0% | 63% | 63% | 88% | 88% | 43% |
| Sensitivity for non-dysplastic Barrets | 100% | 81% | 70% | 56% | 69% | 88% | 0% | 94% | 21% | 56% | 100% | 44% | 13% | 100% | 81% | 100% | 88% | 63% |
| Specificity Sq Cut-off = 0.01 | 97% | 97% | 100% | 100% | 97% | 97% | 100% | 97% | 97% | 97% | 94% | 97% | 100% | 97% | 97% | 97% | 97% | 97% |
| Specificity Sq | 91% | 94% | 100% | 100% | 94% | 94% | 91% | 91% | 93% | 91% | 91% | 94% | 94% | 94% | 94% | 94% | 94% | 94% |

TABLE 1B

| A | T<br>All amplicon together, including VIM | U<br>All 17 SqBE amplicons:<br>SqBE 2<br>SqBE 5<br>SqBE 7<br>SqBE 9<br>SqBE 10<br>SqBE 11-1<br>SqBE 11-2<br>SqBE 13<br>SqBE 14-2<br>SqBE 15<br>SqBE 16-1<br>SqBE 16-2<br>SqBE 17-1<br>SqBE 18<br>SqBE 22-1<br>SqBE 22-2<br>SqBE 23 | V<br>15 SqBE amplicons:<br>SqBE 5<br>SqBE 7<br>SqBE 9<br>SqBE 10<br>SqBE 11-1<br>SqBE 11-2<br>SqBE 13<br>SqBE 14-2<br>SqBE 16-1<br>SqBE 16-2<br>SqBE 17-1<br>SqBE 18<br>SqBE 22-1<br>SqBE 22-2<br>SqBE 23 | W<br>4 best amplicons with highest EAC calls (SqBE 10 SqBE 11-2 SqBE 18 SqBE 22-1) perform as well as 16 amplicons | X<br>trio1<br>(SqBE 10<br>SqBE 11-2<br>SqBE 18) | Y<br>trio2<br>(SqBE 10<br>SqBE 11-2<br>SqBE 22-1) | Z<br>trio3<br>(SqBE 10<br>SqBE 18<br>SqBE 22-1) | AA<br>trio4<br>(SqBE 11-2<br>SqBE 18<br>SqBE 22-1) | AB<br>double 1<br>(SqBE 10<br>SqBE 11-2) | AC<br>double 2<br>(SqBE 10<br>SqBE 18) | AD<br>double 3<br>(SqBE 11-2<br>SqBE 18) | AE<br>double 4<br>(SqBE 10<br>SqBE 22-1) | AF<br>double 5<br>(SqBE 11-2<br>SqBE 22-1) | AG<br>double 6<br>(SqBE 18<br>SqBE 22-1) |
|---|---|---|---|---|---|---|---|---|---|---|---|---|---|
| Number of CpGs in amplicon analysis | | | | | | | | | | | | | |
| Number of CpGs used for methylation call | | | | | | | | | | | | | |
| Cut-off = 0.1 | | | | | | | | | | | | | |
| Sensitivity EAC | 100% | 100% | 100% | 100% | 100% | 100% | 100% | 100% | 100% | 100% | 100% | 96% | 100% | 96% |
| Sensitivity HGD | 88% | 88% | 88% | 88% | 75% | 88% | 88% | 88% | 75% | 75% | 63% | 88% | 88% | 88% |
| Sensitivity for non-dysplastic Barrets | 100% | 100% | 100% | 100% | 100% | 100% | 100% | 100% | 100% | 94% | 100% | 100% | 100% | 100% |
| Specificity Sq | 91% | 91% | 97% | 97% | 97% | 97% | 97% | 97% | 97% | 97% | 97% | 97% | 97% | 97% |

Confirmatory analysis of candidate loci was further done using bisulfite sequencing of candidate loci that were amplified using the bisulfite specific but methylation independent amplification primers described above. This employed a new sample set of esophageal brushings obtained using a cytology brush under endoscopic guidance that were obtained first from 59 control subjects with or without symptomatic gastroesophageal reflux disease (GERD), but all without Barrett's esophagus (BE). These controls included persons with normal endoscopic findings or with erosive esophagitis. In these controls brushings were obtained from the gastroesophageal junction to sample the glandular mucosa, and brushings were also obtained from squamous esophagus mucosa. Brushing were also obtained from esophageal lesions of 107 cases that included 60 individuals with cancers, either adenocarcinoma of the esophagus (EAC) (N=46) or adenocarcinoma of the gastroesophageal junction (JCA) (N=14), and included 47 individuals with BE. Of BE cases, 12 had non-dysplastic short-segment BE (SSBE, <3 cm), 17 had nondysplastic long segment BE (LSBE 23 cm), 8 had low-grade dysplasia (LGD), and 10 had high-grade dysplasia (HGD).

Table 1.5 Columns B-F disclose the performance of individual amplicons of select loci having strong performance characteristics and identified in the studies discussed above in the esophageal brushings sample set analyzed using bisulfite sequencing performed on a Next Generation DNA sequencing instrument (an Illumina MiSeq instrument). Table 1.5, row 3 lists the number of CpGs between the amplification primers for each of the amplicons. Table 1.5, row 4, provides the coordinates in hg19 of the genomic interval that covers the the CpGs that lie between the primers (and that may include several non CpG bases within the primers). Table 1.5, row 5 lists the number of CpGs lying between the primers that were required to be methylated on an individual DNA read to count that read as methylated (e.g. for VIM there are 10 CpG residues between the primers, and 8+(meaning >=8) CpGs were required to be methylated on a read to score the read as methylated). Table 1.5 row 6 lists the minimum percent of methylated reads (cut-off) identified by bisulfite sequencing that were required in order to score a sample as methylated and thus detected (e.g. for VIM>=0.0102 fraction of total reads were required to be methylated). Table 1.5 rows 7, 8, 9, 10 and 11 record the sensitivity of each amplicon for detecting: esophageal adenocarcinomas (EACs) (row 7), adenocarcinomas of the gastroesophageal junction (JCAs) (row 8), low grade dysplasias (LGD) (row 9), high grade dysplasias (HGD) (row 10), and non-dysplastic Barrett's esophagus (non-dysplastic BE) (row 11), using criteria in which a sample was detected if it demonstrated methylation at greater than the cut-off value of row 5. Table 1.5 row 12 records the specificity of each amplicon for not detecting normal squamous esophagus mucosa (normal Sq) and row 13 records the specificity of each amplicon for not detecting normal gastroesophageal junction (GEJ).

In Table 1.5, column B provides data for detecting methylation in the Vimentin (VIM) locus amplified using primers disclosed in Li et al. (Li M, et al. (2009) Sensitive digital quantification of DNA methylation in clinical samples. Nat Biotechnol 27(9):858-863). These primers are:

```
Forward Primer:
                                         (SEQ ID 16209)
CTCRTCCTCCTACCRCAAAATATTC
``` and

```
Reverse Primer:
                                         (SEQ ID 16210)
GTTGTTTAGGTTGTAGGTGYGGG
```

(In these notations R denotes alternative sequences that may have either an A or G base, and Y denotes alternative sequences that may have either a C or T base).

The amplicon amplified using these primers is derived from the parental (−) strand and is as follows:

```
Vimentin amplicon (-) strand (SEQ ID NO: 16208):
GtTGtttAGGtTGTAGGTGYGGGTGGAYGTAGTtAYGTAGtTtYGGtT GGAGtTYGGtYGGtTYGYGGTGttYGGGtYGtYGAAtATttTGYGGTA

GGAGGAYGAG
```

The reverse complement of SEQ ID NO: 16208 is also generated.

The region of this amplicon lying between the amplification primers, in which methylation is analysed, is as follows:

```
Vimentin amplicon (-) strand (SEQ ID NO: 16212):
GGAYGTAGTtAYGTAGtTtYGGtTGGAGtTYGGtYGGtTYGYGGTGtt YGGGtYGtYGA
```

The reverse complement of SEQ ID NO: 16212 is also generated and analyzed.

For reference, the bisulfite converted sequence that would be derived from amplifying the corresponding bisulfite converted region derived from the Vimentin (+) strand would be.

```
Vimentin amplicon (+) strand (SEQ ID NO: 16207):
tTYGTtttTttTAtYGtAGGATGTTYGGYGGttYGGGtAtYGYGAGtYG GtYGAGtTtttAGtYGGAGtTAYGTGAtTAYGTttAttYGtAttTAtAG ttTGGGtAGt
```

Along with the reverse complement of SEQ ID NO: 16207. And the corresponding portion of SEQ ID NO: 16211 that falls between the primers used to amplify the Vimentin (−) strand amplicon is:

```
Vimentin amplicon (+) strand (SEQ ID NO: 16211):
TYGGYGGttYGGGtAtYGYGAGtYGGtYGAGtTttAGtYGGAGtTAYG TGAtTAYGTtt
```

Along with reverse complement of SEQ ID NO: 16211.

DNA sequencing reads from each sample were aligned to bisulfite converted and unconverted versions of the human reference genome (hg18) using Bowtie2, and the aligned reads were classified as methylated if they had 8 or more CpG dinucleotides methylated (out of total of 10 CpGs present between the primers in the VIM Bisulfite-seq PCR fragment). These analyses were facilitated by the Bismark software, developed for processing bisulfite-sequencing data.

A sample was considered methylated for VIM if the methylated vimentin allele frequency was greater than 1.02%, i.e. if more than 1.02% of the sequence reads were classified as methylated (a cut-off that maximized the sum of sensitivity plus specificity on the receiver operating curve of all the samples studied). Alternative cutoffs in the range of 0.5-3.0% are also possible. The performance of VIM methylation in detecting esophageal lesions is shown in rows 3-12. Overall, at the cutoff of 1.02% methylation, VIM methylation showed sensitivity of 90.7% for identifying BE or esophageal neoplasia and showed specificity for rejecting normal gastroesophageal junction of 93%. When the cutoff for VIM methylation is varied from 0-100%, and sensitivity is plotted versus (100−specificity) (a receiver operating curve), the area under the curve for the VIM assay=0.949.

In this same sample set, we compared assay of VIM methylation by next generation bisulfite sequencing and the analysis algorithm above (in which >=8 methylated CpG is required to score a read as methylated and >1% of methylated reads defines a cutoff of scoring a sample as methylated and detected) versus performing assay of VIM methylation by quantitative methylated specific PCR (qMSP) (as described in Moinova et al. Cancer Epidemiol Biomarkers Prev. 2012; 21(4):594-600.). The bisulfite sequencing method showed superiority with both better sensitivity and better specificity. In particular, area under the receiver operating curve for the qMSP assay=0.925, and at the optimal cutoff of 2.2% VIM methylation measured by qMSP (as defined by the receiver operating curve), assay sensitivity was 82.9% and assay specificity was 91.3%, which are all inferior to the results obtained with the next generation bisulfite sequencing assay and the analysis algorithm laid out in Table 1.5.

Amplicons need not be used individually, but can be combined into panels for detection of esophageal neoplasia. Examples of such panels, and their associated performance statistics, are provided in Table 1.5, columns G through L, that specify the markers in the panel and the sensitivity and specificity resulting from the marker combination (when the combination is scored positive if any member of the combination is positive). In these marker combinations, each individual member of the panel is analysed using the conditions specified for that marker individually in rows 4 and 5 of columns B-F. The marker combination of methylation in amplicons of VIM or of SqBE18 is of particular interest, as the combination of these two markers show detection of 96% of esophageal adenocarcinomas, 93% of carcinomas of the gastroesophageal junction, 100% of high grade dysplasias, 100% of low grade dysplasias, and 94% of non-dysplastic long segment Barrett's esophagus, while preserving a specificity of 91% for normal gastroesophageal junction.

TABLE 1.5

| A | B<br>VIM | C<br>SqBE 5 | D<br>SqBE 16-1 | E<br>SqBE 18 |
|---|---|---|---|---|
| Number of CpGs in amplicon analysis | 10 | 15 | 26 | 21 |
| hg19 Interval covering CpGs in the amplicon analysis | chr10:<br>17271466-17271524 | chr5:<br>1,883,203-1,883,380 | chr11:<br>110,582,495-110,582,696 | chr13:<br>37,005,877-37,006,009 |
| Number of CpGs used for methylation call | 8+ | 13+ | 15+ | 16+ |
| Cut-off = | 0.0105 | 0.0046 | 0.0106 | 0.0312 |
| Sensitivity EAC | 89% | 86% | 80% | 96% |
| Sensitivity JCA | 79% | 57% | 50% | 86% |
| Sensitivity LGD | 88% | 63% | 75% | 86% |
| Sensitivity HGD | 100% | 78% | 80% | 100% |
| Sensitivity for non-dysplastic Barrets | 94% | 89% | 67% | 78% |
| Specificity Normal Sq | 87% | 97% | 93% | 98% |
| Specificity Normal GEJ | 93% | 93% | 97% | 98% |

| A | F<br>VIM +<br>SqBE 5 | F<br>VIM +<br>SqBE 16-1 | F<br>VIM +<br>SqBE 18 | I<br>SqBE +<br>SqBE 16-1 | J<br>SqBE 5 +<br>SqBE 18 | K<br>SqBE 16-1 +<br>SqBE 18 | L<br>SqBE 5 +<br>SqBE 16-1 +<br>SqBE 18 |
|---|---|---|---|---|---|---|---|
| Number of CpGs in amplicon analysis | | | | | | | |
| hg19 Interval covering CpGs in the amplicon analysis | | | | | | | |
| Number of CpGs used for methylation call | | | | | | | |
| Cut-off = | | | | | | | |
| Sensitivity EAC | 96% | 89% | 96% | 90% | 98% | 96% | 98% |
| Sensitivity JCA | 79% | 79% | 93% | 64% | 86% | 93% | 93% |
| Sensitivity LGD | 88% | 88% | 100% | 75% | 86% | 86% | 86% |
| Sensitivity HGD | 100% | 100% | 100% | 89% | 100% | 100% | 100% |
| Sensitivity for non-dysplastic Barrets | 100% | 94% | 94% | 100% | 100% | 78% | 100% |
| Specificity Normal Sq | 83% | 83% | 87% | 93% | 95% | 92% | 92% |
| Specificity Normal GEJ | 86% | 89% | 91% | 92% | 93% | 97% | 90% |

Figure 1D:
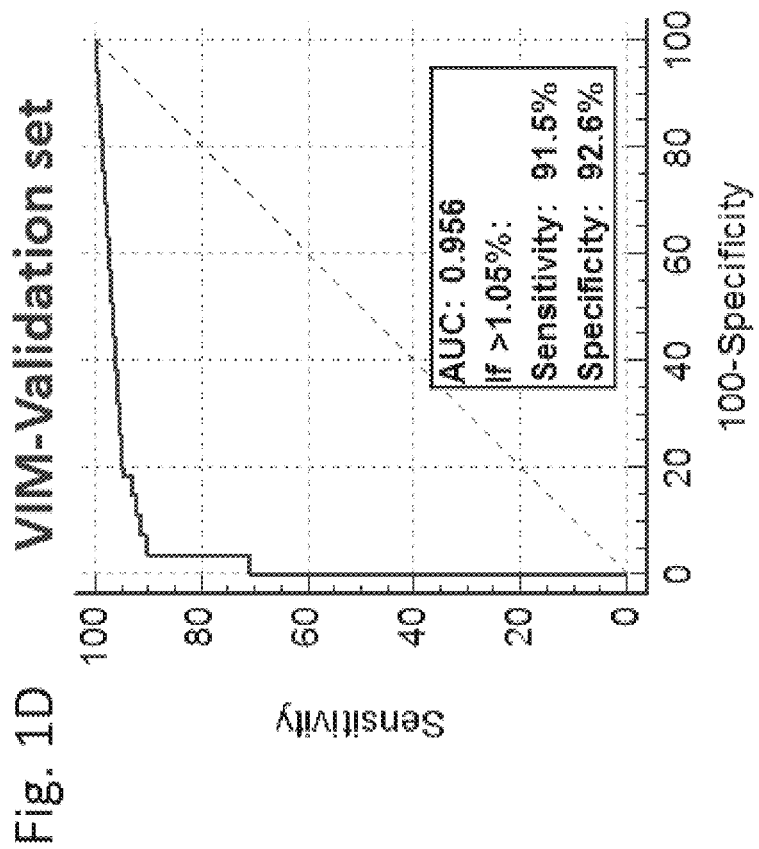
FIG. 1D shows a ROC curve based on Next-Generation Bisulfite Sequencing VIM assay in the validation set of 27 controls and 117 cases. Area under the curve (AUC), and the sensitivity and specificity of the assay at the optimal cutpoint are listed for each of FIGS. 1A-1D. The numbers of cases and controls for each marker in the training and validation set reflect the number of samples that were sequenced with the depth of greater than 80 reads for each marker. (median read depth was 3,809 for SqBE18, and 10,021 for VIM).
Figure 2A:
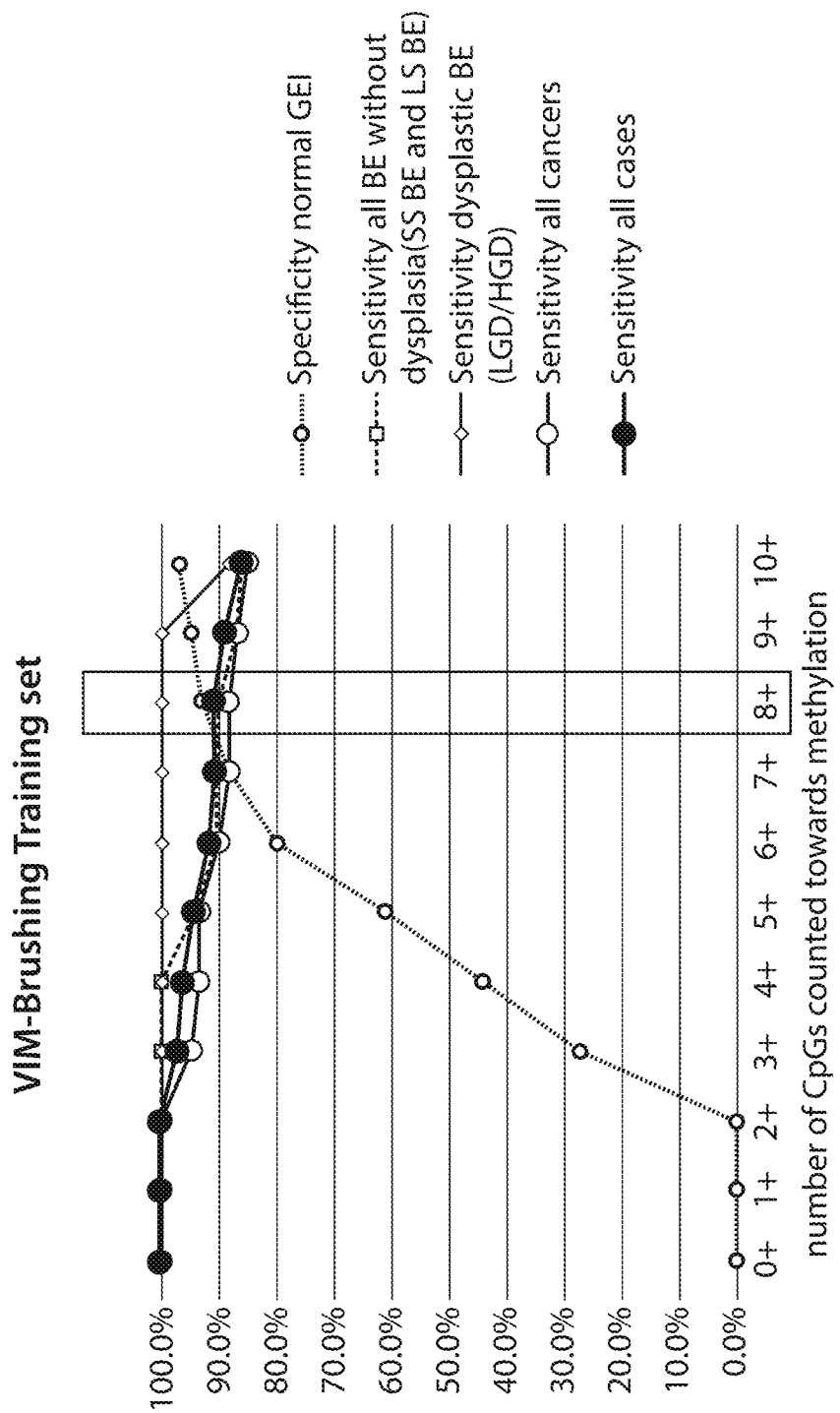
FIGS. 2A and 2B show VIM and SqBE18 performance at different numbers of CpG cutoff for positivity, using the ROC cutoff for percent methylation.

The marker combination of methylation in amplicons of VIM or of SqBE18 was further assessed in esophageal cytology brushings of normal-appearing gastroesophageal junction (GEJ) or of endoscopically visualized BE or EAC. In these experiments, the same vimentin amplicons described above were used and contained 10 CpGs. Vimentin specificity for Normal GEJ samples increases with the requirement that more CpGs in the read should be unmethylated, in order for the sample to be called "unmethylated." Conversely, Vimentin Sensitivity for BE/Cancer decreases with the requirement that more CpGs in the read are required to be called "methylated." The 8+ CpG cutoff (blue box in FIG. 2A), maximizes the sum of specificity for controls and sensitivity for cases. As such, a VIM read was considered methylated if any 8 CpGs out of 10 were methylated. The output for each sample was the fraction of methylated reads in the total number of reads for each sample. These values were then used to generate the Receiver Operating Characteristic (ROC) curve. See FIGS. 1B and 1D that respectively describe training and validation sets of esophageal brushings samples.

Figure 2B:
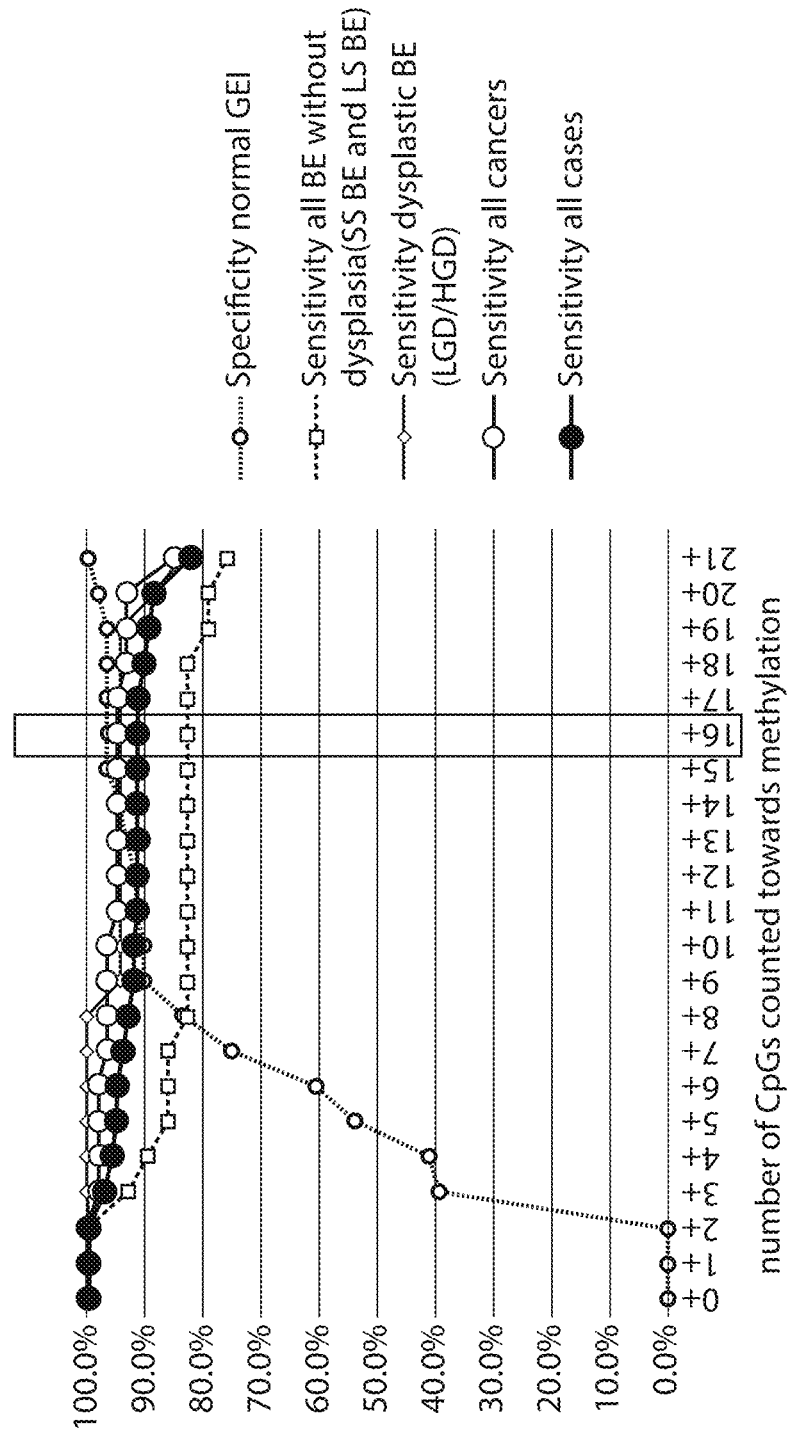

The SqBE18 amplicon used on the same samples described in the paragraph above contained 21 CpGs. These amplicons were generated as described above, and were obtained by amplifying bisulfite converted DNA with PCR primers having the nucleotide sequence of SEQ ID Nos: 8388 and 8402 to derive amplicon sequences having the nucleotide sequence of SEQ ID NO: 8318. SqBE 8 specificity for Normal GEJ samples increases with the requirement that more CpGs in the read should be unmethylated, in order for the sample to be called "unmethylated." Conversely, SqBE18 Sensitivity for BE/Cancer decreases with the requirement that more CpGs in the read are required to be called "methylated." The 15+, 16+, and 17+ CpG cutoffs offer identical maximum sensitivity+specificity sum for SqBE18, 16+ CpGs (blue box of FIG. 2B), was chosen as the middle of this range. As such, a read was considered methylated for the SqBE18 amplicon if any 16 CpGs out of 21 were methylated. The output for each sample was the fraction of methylated reads in the total number of reads for each sample. These values were then used to generate the ROC curve. See FIGS. 1A and 1C.

Due to the patchy nature of methylation, normal samples can contain a few random methylated CpGs, while, conversely, the methylated DNA could contain some unmethylated CpGs. Different CpG islands have different methylation density, and as a result, a cutoff was established for each region that would optimally differentiate methylated and unmethylated DNA. In this study, if greater than 1.05% of VIM reads were methylated, this sample was considered "positive" for VIM methylation, and if greater than 3.11% of SqBE18 reads were methylated, this sample was considered "positive" for VIM methylation.

Vimentin and SqBE18 gene methylation (mVLM and mSqBE18) was assayed in DNA samples from either a training set or a validation set of cytology brushings of the distal esophagus. Both the training and validation sets of brushings of the distal esophagus were from: Unaffected controls (individuals with GERD, erosive esophagitis, or no pathology detected during endoscopy—each brushed at the GE Junction); SSBE (short-segment Barrett's Esophagus (1 to 3 cm)); LSBE (Barrett's Esophagus (3 cm or more); LGD (Barret's Esophagus with Low-Grade Dysplasia); HGD (Barrett's Esophagus with High-Grade Dysplasia); Cancer—includes EAC (Esophageal adenocarcinoma) and JCA (Junctional cancer of the esophagus). In the case of the training sets, samples were scored as methylated when the mVIM methylated allele frequency was measured as >1.05%, and mSqBE 8 methylated allele frequency was measured as >3, 11% by bisulfite sequencing (representing the ROC cutpoints that provide optimal performance for each of these assays, respectively). In the case of the validation sets, samples were scored as methylated when the mVIM methylated allele frequency was measured as >1.05%, and mSqBE18 methylated allele frequency was measured as >3.11% by bisulfite sequencing (representing the ROC cutpoints from the training set of brushings for each of these assays, respectively). For the combination of the two markers, the calculations were performed in two ways:

One-marker fails censored: if either mVIM or mSqBE18 sequencing failed, the sample was excluded from analysis One-marker fails allowed: if one marker failed, the sample was still included in the analysis and scored as positive or negative based on the performance of the one working marker.

The data from the training set analyses are summarized in FIG. 3, and the data from the validation set analyses are summarized in FIG. 4.

All the samples from the training and validation sets of brushings described in the paragraph above were combined and then scored as methylated when the mVIM methylated allele frequency was measured as >1.05%, and mSqBE18 methylated allele frequency was measured as >3.11% by bisulfite sequencing (representing the ROC cutpoints from the training set of brushings for each of these assays, respectively). For the combination of the two markers, the calculations were performed as follows:

Controls—One-marker fails censored: if either mVIM or mSqBE18 sequencing failed, the sample was excluded from analysis. This underscores the specificity of the assay.

Cases—One-marker falls allowed: if one marker failed, the sample was still included in the analysis and scored as positive or negative based on the performance of the one working marker. This underscores the sensitivity of the assay.

For controls: if one marker failed, the sample was censored in order not to overestimate the specificity. For cases: if one marker failed, and the other marker worked, the sample was still counted. The results of these analyses are provided in FIG. 5.

Figure 6A:
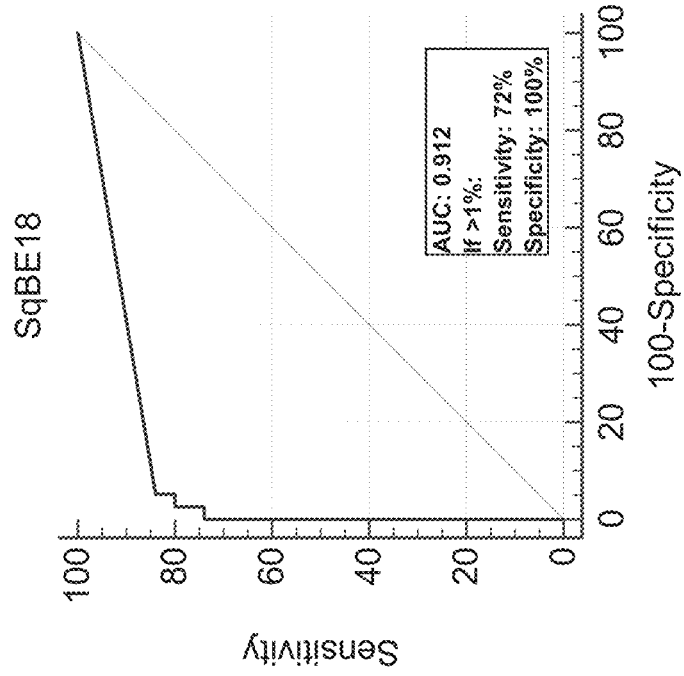
FIGS. 6A and 6B show Receiver Operating Characteristic (ROC) curves of methylated VIM assayed on esophageal balloon samplings of the distal esophagus.

Esophageal balloon samplings of the distal esophagus were assayed for VIM methylation and ROC curves were obtained. FIG. 6A shows a ROC curve based on next-generation bisulfite sequencing assay for VIM in the training set of 38 controls and 50 cases. Similar to the experiments described above, the vimentin amplicon that was used contained 10 CpGs, and a read was considered methylated, if any 8 CpGs out of 10 are methylated (based on the analysis of data in slide 3). The output for each sample was the fraction of methylated reads in the total number of reads for each sample. These values were then used to generate the ROC curve. Optimal ROC cutpoint for mVIM assay on balloons was between 0.95% and 1.16%, and 1% was chosen as a convenient number in the middle of this range. The actual cutoff picked by MedCalc for VIM balloons was 0.95%.

Figure 6B:
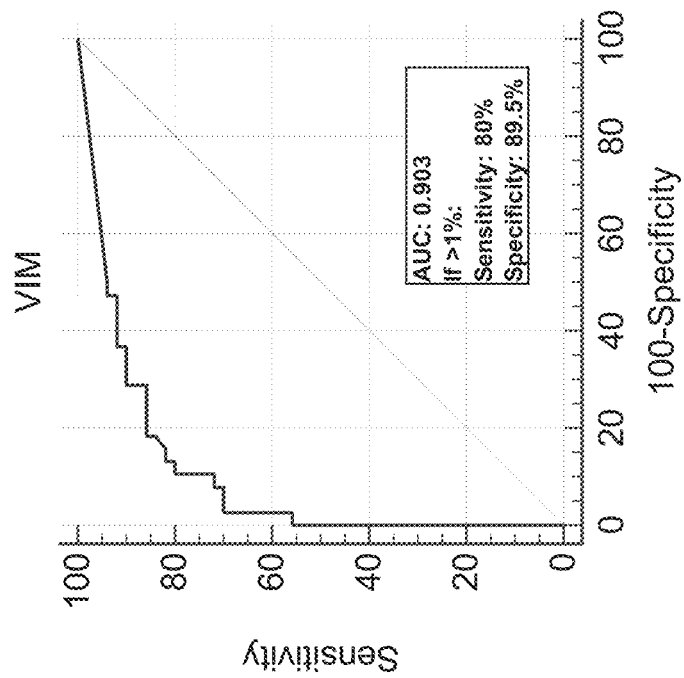

Esophageal balloon samplings of the distal esophagus were also assayed for SqBE18 methylation and ROC curves were obtained. FIG. 6B shows a ROC curve based on next-generation bisulfite sequencing SqBE18 assay in the training set of 38 controls and 50 cases. Similar to the experiments described above, the SqBE18 amplicon that was used contained 21 CpGs, and a read was considered methylated if any 16 CpGs out of 21 were methylated. The output for each sample was the fraction of methylated reads in the total number of reads for each sample. These values were then used to generate the ROC curve. Optimal ROC cutpoint for SqBE18 assay on balloons was between 0.1%, based on maximizing the sum of sensitivity and specificity. However, a higher cutpoint was chosen to maintain higher specificity of the assay. Any cutpoint between 0.76% and 1.06%, would give the same value of sensitivity and specificity. 1% was chosen as the convenient number in the middle of this range. The actual cutoff picked by MedCalc for SqBE18 balloons was 0.1%. However, 1% was chosen as the cutoff to maximize specificity. Any number between 0.76% and 1.06% would have worked the same as 1%. If >0, 1%, then the sensitivity: 84.0%, and the specificity: 94.7%.

Vimentin and SqBE18 gene methylation (mVIM and mSqBE 8) was assayed in esophageal balloon DNA samples of the distal esophagus from: Unaffected controls (individuals with GERD, erosive esophagitis, or no pathology detected during endoscopy; SSBE (short-segment Barrett's Esophagus (1 cm to less than 3 cm)); LSBE (Barrett's Esophagus (3 cm or more); LGD (Barret's Esophagus with Low-Grade Dysplasia); HGD (Barrett's Esophagus with High-Grade Dysplasia); Cancer—includes EAC (Esophageal adenocarcmnoma) and JCA (Junctional cancer of the esophagus). Samples were scored as methylated when die mVIM and SqBE18 methylated allele frequency was measured as >1%, based on balloon ROC curves described in the preceding two paragraphs. The results from these analyses are provided in FIG. 7.

Example 2: Identification of Esophageal Cancer Informative Loci to Detect Progression of Esophageal Neoplasia Discovery data were also analyzed for each individual CpG residue in the RRBS data set to identify loci that could be used to distinguish EAC from BE. Individual CpGs were considered methylated in EAC versus BE if they showed methylation of less than 10% of reads of all informative BE samples, where at least 3 BE samples were informative, and if they showed methylation of less than 10% of reads of all informative normal squamous samples, and where an informative sample had equal to or greater than 20 reads covering the CpG, and if 6 or more of the EAC samples demonstrated percent methylation at a level that was at least 20 percentage points greater than the methylation level of the most methylated BE sample. CpGs meeting criteria for methylation in EAC versus and BE are defined as methylated in EAC vs BE. Such methylated CpGs were then aggregated into patches in instances in which methylated CpGs were within 200 bp one another.

186 genomic patches defined as methylated in EACs versus BE in the discovery set were identified (see SEQ ID NOs: 8447-8818). The genomic coordinates of the genomic patches defined as methylated by the above criteria were also recorded. The genomic sequences of these patches on the respective genomic (+) and (−) strands were determined and recorded. (Upper and lower case designations were used according to those of the UCSC browser, where lower case sequences are lower complexity DNA sequences). The bisulfite converted sequences of these corresponding patches (i.e. the bisulfite converted sequence of the (+) strand and the bisulfite converted sequence of the (−) strand) were determined and recorded (see sequences of SEQ ID NOs: 8819-9004 and 9191-9376 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding patches (i.e. in which all Y bases in every bisulfite converted sequence are retained as a C), corresponding to the (+) strand the (−) strand were determined and recorded (see sequences of SEQ ID NOs: 9005-9190 and 9377-9562 for the bisulfite converted sequences of the fully methylated form of the (+) and (−) strands respectively of the corresponding patches). The reverse complements of the bisulfite converted methylated (+) stand and (−) stand sequences will be obvious to one of ordinary skill in the art and are also included by implication in this disclosure.

Patches were expanded by 100 base pairs on either side so as to accommodate either the design of amplification primers or to enclude additional presumptively methylated bases. The sequences of these expanded patches correspond to SEQ ID NOs: 9563-9934 and their genomic coordinates were also recorded. The genomic sequences of these expanded patches on the respective genomic (+) and (−) strands were determined and recorded. (Upper and lower case designations were used according to those of the UCSC browser, where lower case sequences are lower complexity DNA sequences). The bisulfite converted sequences of these corresponding expanded patches (i.e. the bisulfite converted sequence of the (+) strand and the bisulfite converted sequence of the (−) strand) were determined and recorded (see sequences of SEQ ID NOs: 9935-10120 and 10307-10492 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding expanded patches (i.e. in which all Y bases in every bisulfite converted sequence are retained as a C), corresponding to the (+) strand the (−) strand were determined and recorded (see sequences of SEQ ID NOs: 10121-10306 and 10493-10678 for the bisulfite converted sequences of the fully methylated form of the (+) and (−) strands respectively of the corresponding expanded patches). The reverse complements of the bisulfite converted methylated (+) stand and (−) stand sequences will be obvious to one of ordinary skill in the art and are also included by implication in this disclosure.

CpG islands overlapping patches that may contain additional CpGs that are methylated coordinately with patches were also defined. The sequences of these CpG islands correspond to SEQ ID NOs: 10679-10972. The genomic coordinates of the CpG islands were also recorded. The genomic sequences of these expanded patches on the respective genomic (+) and (−) strands were determined and recorded. (Upper and lower case designations were used according to those of the UCSC browser, where lower case sequences are lower complexity DNA sequences). The bisulfite converted sequences of these corresponding CpG islands (i.e. the bisulfite converted sequence of the (+) strand and the bisulfite converted sequence of the (−) strand) were determined and recorded (see sequences of SEQ ID NOs: 10973-11119 and 11267-11413 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the corresponding CpG islands (i.e. in which all Y bases in every bisulfite converted sequence are retained as a C), corresponding to the (+) strand the (−) strand were determined and recorded (see sequences of SEQ ID NOs: 11120-11266 and 11414-11266 for the bisulfite converted sequences of the fully methylated form of the (+) and (−) strands respectively of the corresponding CpG islands). The reverse complements of the bisulfite converted methylated (+) stand and (−) stand sequences will be obvious to one of ordinary skill in the art and are also included by implication in this disclosure.

Regions of Interest (ROI) were defined that provided preferred regions for design of PCR amplicons that would encompass preferred patches. The genomic coordinates of the ROI were also recorded. The sequences of the (+) strands of the Regions of Interest correspond to SEQ ID NOs: 12563-12568, and the sequences of the (−) strands Regions of Interest correspond to SEQ ID NOs: 12581-12586. (Upper and lower case designations were used according to those of the UCSC browser, where lower case sequences are lower complexity DNA sequences). The bisulfite converted sequences of these corresponding Regions of Interest (i.e. the bisulfite converted sequence of the (+) strand and the bisulfite converted sequence of the (−) strand) were determined and recorded (see sequences of SEQ ID NOs: 12569-12574 and 12587-12592 for the bisulfite converted sequences of the respective (+) and (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the Regions of Interest (i.e. in which all Y bases in every bisulfite converted sequence are retained as a C), corresponding to the (+) strand the (−) strand were determined and recorded (see sequences of SEQ ID NOs: 12575-12580 and 12593-12598 for the bisulfite converted sequences of the fully methylated form of the (+) and (−) strands respectively of the corresponding Regions of Interest). The reverse complements of the bisulfite converted methylated (+) stand and (−) stand sequences will be obvious to one of ordinary skill in the art and are also included by implication in this disclosure.

Specific PCR Amplicons were defined within the Regions of Interest (ROI). The genomic coordinates of the Amplicons were recorded. The sequences of the (+) strands of the Amplicons correspond to SEQ ID NOs: 12599-12604 and 12647-12649, and the sequences of the (−) strands of the Amplicons correspond to SEQ ID NOs: 12617-12622 and 12656-12658. (Upper and lower case designations were used according to those of the UCSC browser, where lower case sequences are lower complexity DNA sequences). The bisulfite converted sequences of these Amplicons (i.e. the bisulfite converted sequence of the (+) strand and the bisulfite converted sequence of the (−) strand) were determined and recorded (see sequences of SEQ ID NOs: 12605-12610 and 12650-12652 for the bisulfite converted sequences of the (+) strands and see sequences of SEQ ID NOs: 12623-12628 and 12659-12661 and for the bisulfite converted sequences of the (−) strands). C residues that may be methylated or unmethylated, and hence may be bisulfite converted to T (if unmethylated) or remain as a C (if methylated), were designated with a Y (where Y denotes C or T), and where, after bisulfite conversion, actual maintenance of a Y designated base as a C was scored as methylation at that base. Thus, these sequences represent the group of all combinations of all sequences in which 0, 1, or more than one Y is converted to a T. The reverse complements of the bisulfite converted sequences of the (+) and (−) strands will be obvious to one of ordinary skill in the art and are also included by implication in this disclosure. The bisulfite converted sequences of the fully methylated form of the Amplicons (i.e. in which all Y bases in every bisulfite converted sequence are retained as a C), corresponding to the (+) strand the (−) strand were determined and recorded (see sequences of SEQ ID NOs: 12611-12616 and 12653-12655 for the bisulfite converted sequences of the fully methylated form of the (+) strands and see sequences of SEQ ID NOs: 12629-12634 and 12662-12664 for the bisulfite converted sequences of the fully methylated form of the (−) strands). The reverse complements of the bisulfite converted methylated (+) stand and (−) stand sequences will be obvious to one of ordinary skill in the art and are also included by implication in this disclosure. Sequences of PCR primers used in amplification of the Amplicons are provided as SEQ ID NOs: 12635-12646 and 12665-12670.

Confirmatory analysis of candidate loci was then done using bisulfite sequencing of candidate loci that were amplified using bisulfite specific but methylation independent amplification primers. This employed a new sample set of biopsies from: 23 EACs, 8 HGD, 15 non-dysplastic BE from individuals without known higher grade lesions. In addition, biopsies were obtained from 5 cases of BE adjacent to HGD, and from 11 cases of BE adjacent to an EAC. These are not included in analyses of non-dysplastic BE. In addition biopsies were obtained from 33 normal squamous mucosa samples.

Table 2 describes the performance in the confirmatory sample set using bisulfite sequencing analysis of amplicons from select loci defined as methylated in EACs versus BE and having preferred marker characteristics. In Table 2, Columns B-J disclose the performance of the amplicons in the confirmatory data set. In this data set, methylation was calculated as the average level of methylation of all CpGs in between the primers for amplifying the amplicon. For each read across each amplicon the number of CpGs that were methylated was counted and the read was classified as methylated or unmethylated using cutoffs for a required number of methylated CpGs on the amplicon. Table 2, row 3 lists the number of CpGs between the amplification primers for each of the amplicons. Table 2, row 4 lists the number of CpGs that need to be methylated on an individual read to count that read as methylated (e.g. for Up3 there are 36 CpG residues between the primers, and 25+(meaning >=25) CpGs must be methylated on a read to score it as methylated). Table 2, rows 6 and 7 record the sensitivity for detecting EACs (row 6) and HGD (row 7) using criteria in which a sample was detected if it demonstrated methylation in greater than 10% (0.1) of all DNA reads. Table 2, rows 8 and 9 record the specificity of each amplicon for not detecting non-dysplastic BE (row 8) and for not detecting normal squamous mucosa (row 9) again using criteria in which a sample was detected if it demonstrated methylation in greater than 10% (0.1) of all DNA reads. Table 2, rows 11 and 12 record the specificity of each amplicon for not detecting non-dysplastic BE (row 11) and for not detecting normal squamous mucosa (row 12) using criteria in which a sample was detected if it demonstrated methylation in greater than 1% (0.01) of all DNA reads. Amplicons (and patches) need not be used individually, but can be combined into panels for detection of esophageal neoplasia. Performance statistics of selected panels of amplicons are provided in Table 2 columns K through V that provides the sensitivity and specificity of the panels (when the combination is positive if any member of the combination is positive).

TABLE 2A

| A | B<br>Up3 | C<br>Up10 | D<br>Up15_ampl1 | E<br>Up15_ampl2 | F<br>Up20_ampl2 | G<br>Up20_ampl2 | H<br>Up27 | I<br>Up35_ampl1 | J<br>Up35_ampl2 |
|---|---|---|---|---|---|---|---|---|---|
| Number of CpGs in amplicon analysis | 36 | 30 | 25 | 26 | 21 | 16 | 21 | 26 | 18 |
| Number of CpGs used for methylation call | 25+ | 17+ | 15+ | 15+ | 11+ | 6+ | 11+ | 14+ | 10+ |
| Cut-off = 0.1 | | | | | | | | | |
| Sensitivity EAC | 15% | 40% | 22% | 26% | 37% | 0% | 20% | 45% | 30% |
| Sensitivity HGD | 0% | 25% | 13% | 0% | 33% | 0% | 17% | 17% | 25% |
| Specificity for non-dysplastic BE | 100% | 100% | 100% | 94% | 100% | 100% | 100% | 100% | 100% |
| Specificity Sq | 100% | 100% | 100% | 97% | 100% | 100% | 97% | 100% | 100% |
| Cut-off = 0.01 | | | | | | | | | |
| Specificity for non-dysplastic BE | 100% | 100% | 100% | 94% | 94% | 100% | 100% | 100% | 100% |
| Specificity Sq | 100% | 88% | 100% | 91% | 90% | 100% | 93% | 100% | 100% |

TABLE 2B

| A | K<br>All amplicons together:<br>Up3, Up10, Up15-1, Up15-2, Up20-1, Up20-2, Up27, Up35-1, Up35-2 | L<br>6 core amplicon:<br>Up3, Up15-1, Up15-2, Up27, Up35-1 | M<br>7 amplicon: combo 1:<br>up10 and Up3, Up15-1, Up15-2, Up20-1, Up27, Up35-1 | N<br>7 amplicon combo 2:<br>Up35-2 and Up3, Up15-1, Up15-2, Up20-1, Up27, Up35-1 | O<br>2 amplicon combo 1:<br>Up15-1, Up35-1 | P<br>3 amplicon combo:<br>Up15-1, Up35-1, Up10 | Q<br>3 amplicon combo 2:<br>Up15-1, Up35-1, Up20-1 | R<br>4 amplicon combo 1:<br>Up15-1, Up35-1, Up10, Up15-2 | S<br>4 amplicon combo 2:<br>Up15-1, Up35-1, Up10, Up27 | T<br>4 amplicon combo 3:<br>Up15-1, Up35-1, Up15-2, Up20-1 | U<br>4 amplicon combo 4:<br>Up15-1, Up35-1, Up15-2, Up27 | V<br>4 amplicon combo 5:<br>Up15-1, Up35-1, Up20-1, Up27 |
|---|---|---|---|---|---|---|---|---|---|---|---|---|
| Number of CpGs in amplicon analysis | | | | | | | | | | | | |
| Number of CpGs used for methylation call | | | | | | | | | | | | |
| Cut-off = 0.1 | | | | | | | | | | | | |
| Sensitivity EAC | 65% | 65% | 65% | 65% | 52% | 57% | 57% | 61% | 61% | 61% | 61% | 61% |

TABLE 2B-continued

| A | K All amplicons together: Up3, Up10, Up15-1, Up15-2, Up20-1, Up20-2, Up27, Up35-1, Up35-2 | L 6 core amplicon: Up3, Up15-1, Up15-2, Up20-1, Up27, Up35-1 | M 7 amplicon combo 1: up10 and Up3, Up15-1, Up15-2, Up20-1, Up27, Up35-1 | N 7 amplicon combo 2: Up35-2 and Up3, Up15-1, Up15-2, Up20-1, Up27, Up35-1 | O 2 amplicon combo: Up15-1, Up35-1 | P 3 amplicon combo 1: Up15-1, Up35-1, Up10 | Q 3 amplicon combo 2: Up15-1, Up35-1, Up20-1 | R 4 amplicon combo 1: Up15-1, Up35-1, Up10, Up15-2 | S 4 amplicon combo 2: Up15-1, Up35-1, Up10, Up27 | T 4 amplicon combo 3: Up15-1, Up35-1, Up15-2, Up20-1 | U 4 amplicon combo 4: Up15-1, Up35-1, Up15-2, Up27 | V 4 amplicon combo 5: Up15-1, Up35-1, Up20-1, Up27 |
|---|---|---|---|---|---|---|---|---|---|---|---|---|
| Sensitivity HGD | 50% | 38% | 50% | 50% | 25% | 38% | 38% | 38% | 38% | 38% | 25% | 38% |
| Specificity for non-dysplastic BE | 94% | 94% | 94% | 94% | 100% | 100% | 100% | 94% | 100% | 94% | 94% | 100% |
| Specificity Sq Cut-off = 0.01 | 94% | 94% | 94% | 94% | 100% | 100% | 100% | 97% | 97% | 97% | 94% | 97% |
| Specificity for non-dysplastic BE | 88% | 88% | 88% | 88% | 100% | 100% | 94% | 94% | 100% | 88% | 94% | 94% |
| Specificity Sq | 82% | 82% | 82% | 82% | 100% | 94% | 91% | 88% | 91% | 85% | 88% | 88% |

In addition, RRBS discovery data was analyzed to identify CpG residues that demonstrated: i) at least 3 informative BE, which in every informative BE demonstrated at least 90% methylation; and where ii) no more than 5% of informative normal squamous samples demonstrated methylation level below 90%; and that iii) demonstrated at least 6 informative EAC, where in these informative EACs the level of methylation was at least 20 percentage points lower than the methylation level of the least methylated BE. CpGs meeting these criteria are defined as unmethylated in EAC versus BE. Such unmethylated CpGs were then aggregated into patches by grouping together unmethylated CpGs that were within 200 bp of one another. Unmethylated in EAC patches may consist of 1 CpG up to any number of CpGs that meet the above criteria.

Example 3: Identification of Esophageal Cancer Informative Loci to Detect Progression of Esophageal Neoplasia Biopsy samples (that overlapped with the confirmatory biopsy sample set) were further analyzed in tests of panels of markers for detecting the progression of Barrett's esophagus to Barrett's esophagus high grade dysplasia (HGD) or to esophageal adenocarcinoma (EAC). Three panels of markers were selected for study. The first marker panel consisted of detecting at least one of the following four methylated markers: Up15-1, Up35-1, Up27, and Up10 (using bisulfite sequencing analysis of the corresponding amplicons and using the criteria for detection specified in table 2A). The second panel consisted of testing for somatic non-synonymous mutations in TP53 in assays in which TP53 was amplified from genomic DNA using a set of PCR amplicons that spanned the TP53 coding region and in which Next Generation DNA Sequencing was then used to compare TP53 sequences from esophageal lesions versus matched normal esophagus tissue. Samples were classified as detected if a TP53 mutant allele frequency of greater than or equal to 10% was identified. The third panel was a combination of detection of methylation in any of Up15-1, Up35-1, Up27, and Up10 or detection of mutation in TP53.

Table 3 shows the individual performance of biomarkers in detecting the different sample types of the 1st validation biopsies set using different cut-off criteria for methylation than the analysis of table 2. Shown is the performance for detection of different sample types of 5 different methylated DNA markers tested by bisulfite sequencing analysis of the corresponding amplicons (Up3, Up10, Up27, Up35-1, Up35-2). Table 3 specifies the number of CpGs required to be methylated on a DNA sequence read to classify that read as methylated for this analysis. Results are presented when samples are considered methylated if greater than or equal to 1% of all DNA sequence reads are classified as methylated, or if greater than or equal to 10% of all DNA sequence reads are classified as methylated. Also shown is the performance for detecting samples of testing for non-synonymous somatic mutation in assays in which TP53 was amplified from genomic DNA using a set of PCR amplicons that spanned the TP53 coding region and in which Next Generation DNA Sequencing was then used to compare TP53 sequences from esophageal lesions versus matched normal esophagus tissue. Shown are rates of sample detection (expressed as sensitivity or specificity) when samples are classified as TP53 mutant if greater than or equal to 3% of TP53 reads are scored as mutant, or if greater than or equal to 100% of TP53 reads are scored as mutant.

TABLE 3

| Category | Unchanged CpG # cut-off applied to all sample sets | | | Updated CpG # Cut-off applied to all sample sets | | |
|---|---|---|---|---|---|---|
| | Up3 25+ CpGs >1% = positive | Up35-1 14+CpGs >1% = positive | Up35-2 10+CpGs >1% = positive | Up10 26+CpGs >1% = positive | Up27 15+CpGs >1% = positive | p53 >3% |
| Sensitivity EAC | 20% | 50% | 35% | 30% | 20% | 70% |
| Sensitivity for BEs synchronous to EAC or HGD | 7% | 20% | 19% | 0% | 7% | 25% |
| Sensitivity HGD | 17% | 33% | 38% | 0% | 17% | 25% |
| Specificity Sq | 100% | 100% | 100% | 100% | 97% | 100% |
| Specificity for non-dysplastic BE | 100% | 100% | 100% | 100% | 100% | 100% |
| | >10% = positive | >1.0% = positive | >10% = positive | >10% = positive | >1.0% = positive | >10% = positive |
| Sensitivity EAC | 15% | 45% | 30% | 10% | 15% | 61% |
| Sensitivity for BEs matching higher pathologies, either EAC or HGD | 7% | 7% | 6% | 0% | 7% | 19% |
| Sensitivity HGD | 0% | 17% | 25% | 0% | 17% | 25% |

Table 4 shows the performance of selected combinations of the methylated DNA markers (Up3, Up10, Up27, Up35-1, Up35-2) for detection of different sample types in the experiment presented in Table 3. Samples are scored as methylated if any member of the marker combination panel scores the sample as methylated. Results are presented when the individual markers are considered methylated if greater than or equal to 1% of all DNA sequence reads are classified as methylated, or if greater than or equal to 10% of all DNA sequence reads are classified as methylated.

TABLE 4A

| Cut-off for positivity (e.i. samples is positive if more than this % of reads are methylated at the given number of CpGs) | Category | Up3 and Up35-1 | Up3 and Up35-2 | Up3 and Up10 | Up3 and Up27 | Up35-1 and Up35-2 | Up35-1 and Up10 | Up35-1 and Up27 | Up35-2 and Up10 | Up35-2 and Up27 | Up10 and Up27 | Up3. Up35-1, Up35-2 | Up3. Up354, Up10 |
|---|---|---|---|---|---|---|---|---|---|---|---|---|---|
| 1% | Sensitivity EAC | 50% | 45% | 50% | 35% | 50% | 60% | 60% | 50% | 50% | 40% | 50% | 60% |
| 1% | Sensitivity for BEs synchronous to EAC or HGD | 20% | 20% | 11% | 13% | 27% | 11% | 20% | 11% | 27% | 0% | 27% | 11% |
| 1% | Sensitivity HGD | 33% | 33% | 25% | 33% | 33% | 50% | 50% | 50% | 50% | 0% | 33% | 50% |
| 1% | Specificity Sq | 100% | 100% | 100% | 97% | 97% | 100% | 97% | 100% | 97% | 94% | 100% | 100% |
| 1% | Specificity for non-dysplastic BE | 100% | 100% | 100% | 100% | 100% | 100% | 100% | 100% | 100% | 100% | 100% | 100% |

TABLE 4A-continued

| Cut-off for positivity (e.i. samples is positive if more than this % of reads are methylated at the given number of CpGs) | Category | Up3 and Up35-1 | Up3 and Up35-2 | Up3 and Up10 | Up3 and Up27 | Up35-1 and Up35-2 | Up35-1 and Up10 | Up35-1 and Up27 | Up35-2 and Up10 | Up35-2 and Up27 | Up10 and Up27 | Up3. Up35-1, Up35-2 | Up3. Up354, Up10 |
|---|---|---|---|---|---|---|---|---|---|---|---|---|---|
| 10% | Sensitivity EAC | 45% | 35% | 30% | 25% | 45% | 50% | 50% | 30% | 40% | 20% | 45% | 50% |
|  | Sensitivity for BEs matching higher pathologies, either EAC or HGD | 13% | 13% | 11% | 13% | 7% | 0% | 13% | 0% | 13% | 0% | 13% | 11% |
| 10% | Sensitivity GD | 17% | 33% | 0% | 17% | 33% | 25% | 33% | 50% | 50% | 0% | 33% | 25% |

TABLE 4B

| Cut-off for positivity (e.i. samples is positive if more than this % of reads are methylated at the given CpGs) | Category | Up3, Up35-1, Up27 | Up3, Up35-2, Up10 | Up3, Up35-2, Up27 | Up3, Up10, Up27 | Up35-1, Up10, up27 | Up35-2, Up10, up27 | Up3, Up35-1, Up35-2, Up10 | Up3, Up35-1, Up35-2, Up27 | Up35-1, Up35-2, Up10, Up27 | Up3, Up35-2, Up10, Up27 | Up3, Up35-1, Up10, Up27 | All 5 markers together |
|---|---|---|---|---|---|---|---|---|---|---|---|---|---|
| 1% | Sensitivity EAC | 60% | 60% | 55% | 60% | 70% | 60% | 60% | 60% | 70% | 70% | 70% | 70% |
| 1% | Sensitivity for BEs synchronous to EAC or HGD | 20% | 11% | 27% | 11% | 11% | 11% | 11% | 27% | 11% | 11% | 11% | 11% |
| 1% | Sensitivity HGD | 50% | 50% | 50% | 25% | 50% | 50% | 50% | 50% | 50% | 50% | 50% | 50% |
| 1% | Specificity Sq | 97% | 100% | 97% | 94% | 94% | 94% | 100% | 97% | 94% | 94% | 94% | 94% |
| 1% | Specificity for non-dysplastic BE | 100% | 100% | 100% | 100% | 100% | 100% | 100% | 100% | 100% | 100% | 100% | 100% |
| 10% | Sensitivity EAC | 50% | 30% | 40% | 40% | 60% | 40% | 50% | 50% | 40% | 40% | 60% | 60% |
| 10% | Sensitivity for BEs matching higher pathologies, either EAC or HGD | 20% | 11% | 20% | 11% | 0% | 0% | 11% | 20% | 11% | 11% | 11% | 11% |
| 10% | Sensitivity HGD | 33% | 50% | 50% | 0% | 25% | 50% | 50% | 50% | 50% | 50% | 25% | 50% |

Samples summarized in Table 3 and Table 4 were additionally tested for non-synonymous somatic mutations in TP53. Table 5 shows performance of selected combinations of methylated DNA markers (Up3, Up100, Up27, Up35-1, Up35-2) plus testing for mutations in TP53 (p53) for detection of different sample types. Samples are scored as detected if any member of the marker combination panel scores the sample as methylated or if analysis for TP53 mutations scores the sample as TP53 mutant. Shown is the performance of the marker panel in which samples are scored as detected if any methylation marker is detected as methylated at greater than or equal to 1% of DNA reads, or if TP53 is detected as mutant at greater than or equal to 10% of the DNA sequence reads. Also shown is the performance of the marker panel in which samples are scored as detected if any methylation marker is detected as methylated at greater than or equal to 10% of DNA reads, or if TP53 is detected as mutant at greater than or equal to 10% of the DNA sequence reads.

TABLE 5A

| Cut-off for positivity (e.i. sample is positive if more than this % of reads are methylated at the given number of CpGs) | P53 cut-off | Category | Up3 and p53 | Up35-1 and p53 | Up-3 and P53 | Up10 and P53 | Up27 and p53 |
|---|---|---|---|---|---|---|---|
| 1% | 10% | Sensitivity EAC | 70% | 80% | 70% | 60% | 70% |
| 1% | 10% | Sensitivity for BEs synchronous to EAC or HGD | 20% | 20% | 19% | 11% | 27% |
| 1% | 10% | Sensitivity HGD | 33% | 50% | 38% | 25% | 33% |
| 1% | 10% | Specificity Sq | 100% | 100% | 100% | 100% | 97% |
| 1% | 10% | Specificity for non-dysplastic BE | 100% | 100% | 100% | 100% | 100% |
| | | Individual Methylation Markers + P53 | | | | | |
| 10% | 10% | Sensitivity EAC | 70% | 80% | 70% | 60% | 70% |
| | 10% | Sensitivity for BEs matching higher pathologies, either EAC or HGD | 20% | 20% | 19% | 11% | 27% |
| 10% | 10% | Sensitivity GD | 33% | 50% | 38% | 25% | 33% |

TABLE 5B

| Cut-off for positivity (e.i. sample is positive if more than this % of reads are methylated at the given number of CpGs) | P53 cut-off | Category | Up3 and Up35-2 and p53 | Up3 and Up10 and p53 | Up3 and Up27 and p53 | Up35-2 and Up10 and p53 | Up35-2 and Up27 and p53 | Up10 and Up27 and p53 | Up3, Up35-2, Up10 and p53 | Up3, Up35-2, Up27 and p53 | Up3, Up10, Up27 and p53 | Up35-2, Up10, Up27 and p53 | Up35-1, Up35-2, Up10 Up27 and p53 | Up3, Up35-2, Up10 Up27 and p53 |
|---|---|---|---|---|---|---|---|---|---|---|---|---|---|---|
| 1% | 10% | Sensitivity EAC | 80% | 80% | 80% | 70% | 80% | 80% | 60% | 85% | 90% | 80% | 90% | 90% |
| 1% | 10% | Sensitivity for BEs synchronous to EAC or HGD | 20% | 11% | 27% | 11% | 27% | 11% | 11% | 27% | 11% | 11% | 11% | 11% |
| 1% | 10% | Sensitivity HGD | 50% | 25% | 33% | 50% | 50% | 25% | 50% | 50% | 25% | 50% | 50% | 50% |
| 1% | 10% | Specificity Sq | 100% | 100% | 97% | 100% | 97% | 94% | 100% | 97% | 94% | 94% | 94% | 94% |
| 1% | 10% | Specificity for non-dysplastic BE | 100% | 100% | 100% | 100% | 100% | 100% | 100% | 100% | 100% | 100% | 100% | 100% |
| | | Methylation Marker Combinations Merged with P53 Mutation | | | | | | | | | | | | |
| 10% | 10% | Sensitivity EAC | 75% | 70% | 75% | 70% | 80% | 70% | 30% | 80% | 80% | 80% | 80% | 80% |
| | 10% | Sensitivity for BEs matching higher pathologies, either EAC or HGD | 20% | 11% | 27% | 11% | 27% | 11% | 11% | 27% | 11% | 11% | 11% | 11% |
| 10% | 10% | Sensitivity HGD | 50% | 25% | 33% | 50% | 50% | 25% | 50% | 50% | 25% | 50% | 50% | 50% |

DNA was also extracted from esophageal samples that were also obtained by cytology brushings of the esophagus. The sample set included brushings from 49 esophageal adenocarcinomas (EAC); 14 carcinomas of the gastro-sophageal junction (JCA); 8 Barrett's esophagus with low grade dysplasia (LGD); 9 Barrett's esophagus with high-grade dysplasia (HGD); 33 cases of Barrett's esophagus without dysplasia from cases without HGD or EAC, otherwise termed non-dysplastic BE, that included 13 cases of short segment Barrett's esophagus (SSBE). Also included were brushings of the gastroesophageal junction (normal GEJ) from 62 individuals without Barrett's esophagus, without HGD, without EAC. This included individuals with gastroesophageal reflux disease, with eosinophilic esophagitis, or without any disease. Also included were 176 brushings of normal squamous esophagus from each of the above individuals. These DNA samples were analyzed for methylation by bisulfite sequencing of selected amplicons and were also analyzed for non-synonymous somatic mutations in TP53.

Table 6 shows the individual performance of biomarkers in detecting the different sample types of the validation brushings set. Shown is the performance for detection of different sample types of 5 different methylated DNA markers analyzed by bisulfite sequencing of selected amplicons (Up3, Up10, Up27, Up35-1, Up35-2). The table specifies the number of CpGs required to be methylated on a DNA sequence read to classify that read as methylated. Results are presented when samples are considered methylated if greater than or equal to 1% of all DNA sequence reads are classified as methylated, or if greater than or equal to 10% of all DNA sequence reads are classified as methylated. Also shown is the performance for detecting samples of testing for somatic mutation in assays in which TP53 was amplified from genomic DNA using a set of PCR amplicons that spanned the TP53 coding region and in which Next Generation DNA Sequencing was then used to compare TP53 sequences from esophageal lesions versus matched normal esophagus tissue. Shown are rates of sample detection (expressed as sensitivity or specificity) when samples are classified as TP53 mutant if greater than or equal to 3% of TP53 reads are scored as mutant, or if greater than or equal to 10% of TP53 reads are scored as mutant.

TABLE 6A

| | Unchanged CpG # cut-off applied to all sample sets | | |
|---|---|---|---|
| Category | Up-3 25 + CpGs >1% = positive | Up35-1 14 + CpGs >1% = positive | Up35-2 10 + CpGs >1% = positive |
| Sensitivity EAC | 44% | 57% | 57% |
| Sensitivity JCA | 14% | 43% | 21% |
| Sensitivity LGD | 25% | 38% | 25% |
| Sensitivity HGD | 67% | 56% | 50% |
| Specificity normal GEJ | 98% | 98% | 98% |
| Specificity for "non-dysplastic BE"- excluding SSBE | 95% | 100% | 100% |
| Specificity for all BE without dysplasia (including SSBE and non-dysplastic BE) | 97% | 85% | 94% |
| | >10% = positive | >10% = positive | >10% = positive |
| Sensitivity EAC | 21% | 57% | 45% |
| Sensitivity JCA | 7% | 29% | 7% |
| Sensitivity LGD | 13% | 38% | 25% |
| Sensitivity HGD | 33% | 56% | 30% |
| Specificity normal GEJ | 100% | 100% | 100% |
| Specificity for "non-dysplastic BE"- excluding SSBE | 100% | 100% | 100% |
| Specificity for all BE without dysplasia (including SSBE and non-dysplastic BE) | 100% | 88% | 97% |

TABLE 6B

| | Updated CpG # Cut-off applied to all sample sets | | |
|---|---|---|---|
| Category | Up10 26 + CpGs >1% = positive | Up27 15 + CpGs >1% = positive | p53 >3% |
| Sensitivity EAC | 31% | 43% | 59% |
| Sensitivity JCA | 43% | 14% | 50% |
| Sensitivity LGD | 0% | 13% | 13% |
| Sensitivity HGD | 22% | 20% | 40% |
| Specificity normal GEJ | 98% | 100% | 100% |
| Specificity for "non-dysplastic BE"- excluding SSBE | 100% | 95% | 100% |
| Specificity for all BE without dysplasia (including SSBE mid non-dysplastic BE) | 100% | 94% | 97% |
| | >10% = positive | >10% = positive | >10% = positive |
| Sensitivity EAC | 25% | 29% | 47% |
| Sensitivity JCA | 29% | 7% | 29% |
| Sensitivity LGD | 0% | 13% | 0% |
| Sensitivity HGD | 11% | 20% | 40% |
| Specificity normal GEJ | 100% | 100% | 100% |
| Specificity for "non-dysplastic BE"- excluding SSBE | 100% | 95% | 100% |
| Specificity for all BE without dysplasia (including SSBE and non-dysplastic BE) | 100% | 97% | 97% |

Table 7 shows the performance of selected combinations of the methylated DNA markers (Up3, Up10, Up27, Up35-1, Up35-2) for detection of different sample types in the esophageal brushings samples presented in Table 6. Samples are scored as methylated if any member of the marker combination panel scores the sample as methylated. Results are presented when the individual markers are considered methylated if greater than or equal to 1% of all DNA sequence reads are classified as methylated, or if greater than or equal to 10% of all DNA sequence reads are classified as methylated.

TABLE 7A

| Cut-off for positivity (e.i. sample is positive if more than this % of reads are methylated at the given number of CpGs) | Category | Up3 and Up35-1 | Up3 and Up35-2 | Up3 and Up10 | Up3 and Up27 | Up35-1 and Up35-2 | Up35-1 and Up10 | Up35-1 and Up27 | Up35-2 and Up10 | Up35-2 and Up27 | Up10 and Up27 | Up3, Up35-1, Up35-2 |
|---|---|---|---|---|---|---|---|---|---|---|---|---|
| 1% | Sensitivity EAC | 63% | 60% | 57% | 56% | 61% | 71% | 67% | 71% | 63% | 58% | 63% |
| 1% | Sensitivity JCA | 43% | 21% | 50% | 29% | 43% | 57% | 50% | 50% | 56% | 43% | 45% |
| 1% | Sensitivity LGD | 58% | 58% | 14% | 25% | 33% | 29% | 38% | 29% | 25% | 14% | 38% |
| 1% | Sensitivity HGD | 78% | 78% | 78% | 67% | 56% | 78% | 67% | 67% | 60% | 33% | 78% |
| 1% | Specificity normal GEJ | 98% | 98% | 97% | 98% | 98% | 97% | 98% | 97% | 98% | 98% | 98% |
| 1% | Specificity for non-dysplastic BE | 95% | 95% | 95% | 90% | 100% | 100% | 95% | 100% | 95% | 95% | 95% |
| 1% | Specificity all BE without dysplasia(Including SSBE, and non-dysplastic BE) | 84% | 94% | 97% | 91% | 85% | 85% | 82% | 94% | 91% | 94% | 84% |

TABLE 7A-continued

| Cut-off for positivity (e.i. sample is positive if more than this % of reads are methylated at the given number of CpGs) | Category | Up3 and Up35-1 | Up3 and Up35-2 | Up3 and Up10 | Up3 and Up27 | Up35-1 and Up35-2 | Up35-1 and Up10 | Up35-1 and Up27 | Up35-2 and Up10 | Up35-2 and Up27 | Up10 and Up27 | Up3, Up35-1, Up35-2 |
|---|---|---|---|---|---|---|---|---|---|---|---|---|
| 10% | Sensitivity EAC | 56% | 48% | 38% | 38% | 57% | 67% | 65% | 58% | 55% | 42% | 63% |
| 10% | Sensitivity JCA | 59% | 7% | 29% | 14% | 29% | 43% | 36% | 29% | 14% | 36% | 29% |
| 10% | Sensitivity LGD | 38% | 38% | 0% | 25% | 38% | 29% | 38% | 29% | 25% | 14% | 38% |
| 10% | Sensitivity HGD | 67% | 44% | 33% | 44% | 56% | 67% | 67% | 44% | 50% | 22% | 78% |

TABLE 7B

| Cut-off for positivity (e.i. sample is positive if more than this % of reads are methylated at the given number of CpGs) | Category | Up3, Up35-1, Up10 | Up3, Up35-1, Up27 | Up3, Up35-2, Up10 | Up3, Up35-2, Up27 | Up3, Up10, Up27 | Up35-1, Up10, Up27 | Up35-2, Up10, up27 | Up3, Up35-1, Up35-2, Up10 | Up3, Up35-1, Up35-2, Up27 | Up3, Up35-1, Up35-2, Up10 Up27 | Up3, Up35-2, Up10 Up27 | Up3, Up35-1, Up10 Up27 | All 5 markers together |
|---|---|---|---|---|---|---|---|---|---|---|---|---|---|---|
| 1% | Sensitivity EAC | 72% | 69% | 70% | 67% | 64% | 77% | 75% | 72% | 69% | 74% | 74% | 77% | 77% |
| 1% | Sensitivity JCA | 57% | 50% | 50% | 36% | 50% | 57% | 50% | 57% | 50% | 50% | 50% | 57% | 57% |
| 1% | Sensitivity LGD | 29% | 38% | 29% | 38% | 14% | 29% | 29% | 29% | 36% | 29% | 29% | 29% | 29% |
| 1% | Sensitivity HGD | 89% | 78% | 89% | 73% | 78% | 89% | 78% | 89% | 78% | 89% | 89% | 89% | 89% |
| 1% | Specificity normal GEJ | 97% | 98% | 97% | 98% | 97% | 97% | 97% | 97% | 98% | 97% | 97% | 97% | 97% |
| 1% | Specificity for non-dyspl BE | 95% | 90% | 95% | 90% | 90% | 95% | 95% | 95% | 90% | 90% | 90% | 90% | 90% |
| 1% | Specificity all BE without dysplasia(Including SSBE, and non-dysplastic BE) | 84% | 81% | 94% | 91% | 91% | 82% | 91% | 84% | 81% | 91% | 91% | 81% | 81% |
| 10% | Sensitivity EAC | 66% | 65% | 57% | 56% | 49% | 71% | 63% | 66% | 65% | 62% | 62% | 70% | 70% |
| 10% | Sensitivity JCA | 43% | 36% | 29% | 14% | 36% | 50% | 36% | 43% | 36% | 36% | 36% | 50% | 50% |
| 10% | Sensitivity LGD | 29% | 38% | 29% | 38% | 14% | 29% | 29% | 29% | 38% | 29% | 29% | 29% | 29% |
| 10% | Sensitivity HGD | 67% | 78% | 44% | 56% | 44% | 78% | 56% | 67% | 78% | 56% | 56% | 78% | 78% |

Table 8 shows the performance of selected combinations of methylated DNA markers (Up3, Up10, Up27, Up35-1, Up35-2) plus testing for mutations in TP53 (p53) for detection of different sample types in the esophageal brushings samples presented in Tables 6 and 7. Samples are scored as detected if any member of the marker combination panel scores the sample as methylated or if analysis for TP53 mutations scores the sample as TP53 mutant. Shown is the performance of the marker panel in which samples are scored as detected if any methylation marker is detected as methylated at greater than or equal to 1% of DNA reads, or if TP53 is detected as mutant at greater than or equal to 3% or at greater than or equal to 10% of the DNA sequence reads. Also shown is the performance of the marker panel in which samples are scored as detected if any methylation marker is detected as methylated at greater than or equal to 10% of DNA reads, or if TP53 is detected as mutant at greater than or equal to 3% or at greater than or equal to 10% of the DNA sequence reads. Marker combination with greater than 90% specificity in all BE without dysplasia are preferred yellow. Marker combinations that additionally show superior sensitivity for EAC are further preferred. Particularly preferred marker combinations are: Up35-2 methylation plus TP53 mutation; Up35-2 methylation plus Up3 methylation plus TP53 mutation; Up10 methylation plus Up3 methylation plus TP53 mutation; Up35-2 methylation plus Up10 methylation plus TP53 mutation; Up10 methylation plus Up27 methylation plus TP53 mutation; Up35-2 methylation plus Up3 methylation plus Up10 methylation plus TP53 mutation.

TABLE 8A

| Methyl cut-off (samples are positive if more than this % of reads are methylated at the required number of CpGs) | P53 cut-off | Category | Up-3 and p53 | Up35-1 and p53 | Up35-2 and p53 | Up10 and p53 | Up27 and p53 | Up3 Up35-2 and p53 | Up3 and Up10 and p53 | Up3 and Up27 and p53 |
|---|---|---|---|---|---|---|---|---|---|---|
| 1% | 1% | Sensitivity EAC | 81% | 84% | 86% | 75% | 80% | 88% | 85% | 85% |
| 1% | 1% | Sensitivity JCA | 50% | 64% | 50% | 57% | 57% | 50% | 57% | 57% |
| 1% | 1% | Sensitivity LGD | 25% | 38% | 25% | 14% | 13% | 38% | 14% | 25% |
| 1% | 1% | Sensitivity HGD | 78% | 78% | 70% | 33% | 50% | 89% | 78% | 78% |
| 1% | 1% | Specificity normal GEJ | 98% | 98% | 98% | 98% | 100% | 98% | 97% | 98% |
| 1% | 1% | Specificity for non-dysplastic BE | 95% | 100% | 100% | 100% | 95% | 95% | 95% | 90% |
| 1% | 1% | Specificity all BE without dysplasia (Including SSBE, and non-dysplastic BE) | 94% | 82% | 91% | 97% | 91% | 91% | 94% | 88% |
| 1% | 3% | Sensitivity EAC | 77% | 82% | 84% | 73% | 78% | 85% | 83% | 83% |
| 1% | 3% | Sensitivity JCA | 50% | 64% | 50% | 57% | 57% | 50% | 57% | 57% |
| 1% | 3% | Sensitivity LGD | 25% | 38% | 25% | 14% | 13% | 38% | 14% | 25% |
| 1% | 3% | Sensitivity HGD | 78% | 78% | 70% | 33% | 50% | 89% | 78% | 78% |
| 10% | 3% | Sensitivity EAC | 69% | 82% | 80% | 71% | 71% | 79% | 79% | 75% |
| 10% | 3% | Sensitivity JCA | 50% | 57% | 50% | 57% | 50% | 50% | 57% | 50% |
| 10% | 3% | Sensitivity LGD | 25% | 38% | 25% | 14% | 13% | 38% | 14% | 25% |
| 10% | 3% | Sensitivity HGD | 44% | 78% | 60% | 33% | 50% | 56% | 44% | 56% |
| 10% | 10% | Sensitivity EAC | 60% | 73% | 69% | 60% | 65% | 71% | 70% | 69% |
| 10% | 10% | Sensitivity JCA | 29% | 43% | 29% | 43% | 29% | 29% | 43% | 29% |
| 10% | 10% | Sensitivity LGD | 13% | 38% | 25% | 0% | 13% | 38% | 0% | 25% |
| 10% | 10% | Sensitivity HGD | 44% | 78% | 60% | 33% | 50% | 56% | 44% | 56% |

TABLE 8B

| Methyl cut-off (samples are positive if more than this % of reads are methylated at the required number of CpGs) | P53 cut-off | Category | Up35-2 and Up10 and p53 | Up35-2 and Up27 and p53 | Up10 and Up27 and p53 | Up3, Up35-2, Up10 and p53 | Up3, Up35-2, Up27 and p53 | Up3, Up10, Up27 and p53 | Up35-2, Up10, Up27 and p53 | Up35-1, Up35-2, Up10 Up27 and p53 | Up3, Up35-2, Up10 Up27 and p53 |
|---|---|---|---|---|---|---|---|---|---|---|---|
| 1% | 1% | Sensitivity EAC | 92% | 90% | 85% | 91% | 92% | 87% | 94% | 94% | 94% |
| 1% | 1% | Sensitivity JCA | 57% | 57% | 57% | 57% | 57% | 57% | 57% | 57% | 57% |
| 1% | 1% | Sensitivity LGD | 29% | 25% | 14% | 29% | 38% | 14% | 29% | 29% | 29% |
| 1% | 1% | Sensitivity HGD | 67% | 80% | 44% | 89% | 89% | 78% | 78% | 89% | 89% |
| 1% | 1% | Specificity normal GEJ | 97% | 98% | 98% | 97% | 98% | 97% | 97% | 97% | 97% |
| 1% | 1% | Specificity for non-dysplastic BE | 100% | 95% | 95% | 95% | 90% | 90% | 95% | 90% | 90% |
| 1% | 1% | Specificity all BE without dysplasia (Including SSBE, and non-dysplastic BE) | 91% | 88% | 91% | 91% | 88% | 88% | 88% | 88% | 88% |
| 1% | 3% | Sensitivity EAC | 90% | 88% | 83% | 89% | 90% | 85% | 92% | 91% | 91% |
| 1% | 3% | Sensitivity JCA | 57% | 57% | 57% | 57% | 57% | 57% | 57% | 57% | 57% |
| 1% | 3% | Sensitivity LGD | 29% | 25% | 14% | 29% | 38% | 14% | 29% | 29% | 29% |
| 1% | 3% | Sensitivity HGD | 67% | 80% | 44% | 89% | 89% | 78% | 78% | 89% | 89% |
| 10% | 3% | Sensitivity EAC | 85% | 86% | 77% | 85% | 85% | 81% | 88% | 87% | 87% |
| 10% | 3% | Sensitivity JCA | 57% | 50% | 57% | 57% | 50% | 57% | 57% | 57% | 57% |
| 10% | 3% | Sensitivity LGD | 29% | 25% | 14% | 29% | 38% | 14% | 29% | 29% | 29% |
| 10% | 3% | Sensitivity HGD | 56% | 70% | 44% | 56% | 67% | 56% | 67% | 67% | 67% |
| 10% | 10% | Sensitivity EAC | 77% | 80% | 71% | 77% | 79% | 74% | 81% | 81% | 81% |
| 10% | 10% | Sensitivity JCA | 43% | 29% | 43% | 43% | 29% | 43% | 43% | 43% | 43% |
| 10% | 10% | Sensitivity LGD | 29% | 25% | 14% | 29% | 38% | 14% | 29% | 29% | 26% |
| 10% | 10% | Sensitivity HGD | 56% | 70% | 44% | 56% | 67% | 56% | 67% | 67% | 67% |

Example 4: Analysis of Esophageal Cancer Informative Loci in Formalin Fixed Paraffin Embedded Tissues Additional studies were performed on DNAs extracted from formalin fixed paraffin embedded (FFPE) tissue samples of the stomach and esophagus that capture different diagnostic categories other than Barrett's with high grade dysplasia and esophageal adenocarcinoma. Bisulfite converted DNAs from each sample were amplified with bisulfite specific methylation indifferent primers corresponding to selected amplicons and the amplicons were then analyzed by bisulfite sequencing to determine methylation status on the parental DNA templates.

Table 9 summarizes the side by side comparison of 8 methylated DNA markers in FFPE tissue samples of the stomach and esophagus that capture different diagnostic categories other than Barrett's with high grade dysplasia and esophageal adenocarcinoma. Intestinal metaplasia is abbreviated as IM. Table 9 denotes for each marker the number of methylated cytosine bases required to be detected on a DNA sequence read to classify that read as methylated. Samples are detected as methylated if greater than or equal to 1% of DNA sequence reads are classified as methylated.

TABLE 9A

| Marker<br>CpG cut-off<br>Value (% positive samples or total number of samples sequenced) | VIM<br>6+ | | SqBE5<br>13+ | | SqBE Up7<br>23+ | | SqBE11-2<br>5+ | |
|---|---|---|---|---|---|---|---|---|
| | % positive | Total number | % positive | Total number | % positive | Total number | % positive | Total number |
| BE (IM) | 90% | 30 | 50% | 12 | 50% | 16 | 83% | 30 |
| GEJ/Cardia with IM | 82% | 11 | 0% | 5 | 33% | 6 | 100% | 11 |
| GEJ/Cardia without IM | 0% | 58 | 0% | 33 | 2% | 47 | 31% | 58 |
| columnar mucosa without IM taken from patients with concurrent IM at the same endoscopy | 30% | 10 | 0% | 4 | 20% | 5 | 30% | 10 |
| Normal Distal Esophagus-Squamous | 9% | 23 | 8% | 13 | 0% | 16 | 13% | 23 |
| Squamous Mucosa with REFLUX Esophagus | 0% | 10 | 0% | 6 | 0% | 5 | 0% | 10 |
| Eosinophilic Eosphagitis | 0% | 15 | 0% | 5 | 0% | 11 | 0% | 15 |
| Gastic Mucosa with IM | 22% | 9 | 0% | 2 | 20% | 5 | 44% | 9 |
| Gastric Fundic Mucosa without IM | 0% | 24 | 0% | 14 | 5% | 21 | 8% | 24 |
| *Helicobactor Pylori* Gastritis without IM | 8% | 13 | 22% | 9 | 13% | 8 | 69% | 13 |

TABLE 9B

| Marker<br>CpG cut-off<br>Value (% positive samples or total number of samples sequenced) | SqBE14-2<br>20+ | | SqBE16<br>14+ | | SqBE17<br>17+ | | SqBE18<br>16+ | |
|---|---|---|---|---|---|---|---|---|
| | % positive | Total number | % positive | Total number | % positive | Total number | % positive | Total number |
| BE (IM) | 50% | 16 | 50% | 26 | 69% | 26 | 86% | 29 |
| GEJ/Cardia with IM | 22% | 9 | 18% | 11 | 73% | 11 | 70% | 10 |
| GEJ/Cardia without IM | 2% | 41 | 2% | 55 | 7% | 55 | 0% | 57 |
| columnar mucosa without IM taken from patients with concurrent IM at the same endoscopy | 0% | 5 | 11% | 9 | 11% | 9 | 11% | 9 |
| Normal Distal Esophagus-Squamous | 10% | 20 | 5% | 22 | 4% | 23 | 4% | 23 |
| Squamous Mucosa with REFLUX Esophagus | 17% | 6 | 0% | 8 | 0% | 9 | 0% | 10 |
| Eosinophilic Eosphagitis | 0% | 8 | 0% | 12 | 8% | 13 | 0% | 12 |
| Gastic Mucosa with IM | 0% | 5 | 0% | 7 | 25% | 8 | 14% | 7 |

TABLE 9B-continued

| Marker CpG cut-off Value (% positive samples or total number of samples sequenced) | SqBE14-2 20+ | | SqBE16 14+ | | SqBE17 17+ | | SqBE18 16+ | |
|---|---|---|---|---|---|---|---|---|
| | % positive | Total number | % positive | Total number | % positive | Total number | % positive | Total number |
| Gastric Fundic Mucosa without IM | 0% | 14 | 0% | 24 | 0% | 24 | 8% | 24 |
| *Helicobactor Pylori* Gastritis without IM | 14% | 7 | 8% | 13 | 46% | 13 | 15% | 13 |

Table 10 summarizes the side by side comparison of 8 methylated DNA markers in FFPE tissue samples of the stomach and esophagus that capture different diagnostic categories other than Barrett's with high grade dysplasia and esophageal adenocarcinoma. Intestinal metaplasia is abbreviated as IM. Table 10 denotes for each marker the number of methylated cytosine bases required to be detected on a DNA sequence read to classify that read as methylated. Samples are detected as methylated if greater than or equal to 10% of DNA sequence reads are classified as methylated.

TABLE 10A

| Marker CpG cut-off Value (% positive samples or total number of samples sequenced) | VIM 6+ | | SqBE5 13+ | | SqBE Up7 23+ | | SqBE11-2 5+ | |
|---|---|---|---|---|---|---|---|---|
| | % positive | Total number | % positive | Total number | % positive | Total number | % positive | Total number |
| BE (IM) | 87% | 30 | 50% | 12 | 44% | 16 | 70% | 30 |
| GEJ/Cardia with IM | 82% | 11 | 0% | 5 | 33% | 6 | 91% | 11 |
| GEJ/Cardia without IM | 0% | 58 | 0% | 33 | 2% | 47 | 16% | 58 |
| columnar mucosa without IM taken from patients with concurrent IM at the same endoscopy | 0% | 10 | 0% | 4 | 0% | 5 | 10% | 10 |
| Normal Distal Esophagus-Squamous | 9% | 23 | 8% | 13 | 0% | 16 | 13% | 23 |
| Squamous Mucosa with REFLUX Esophagus | 0% | 10 | 0% | 6 | 0% | 5 | 0% | 10 |
| Eosinophilic Eosphagitis | 0% | 15 | 0% | 5 | 0% | 11 | 0% | 15 |
| Gastic Mucosa with IM | 11% | 9 | 0% | 2 | 20% | 5 | 22% | 9 |
| Gastric Fundic Mucosa without IM | 0% | 24 | 0% | 14 | 5% | 21 | 4% | 24 |
| *Helicobactor Pylori* Gastritis without IM | 8% | 13 | 22% | 9 | 13% | 8 | 46% | 13 |

TABLE 10B

| Marker CpG cut-off Value (% positive samples or total number of samples sequenced) | SqBE14-2 20+ | | SqBE16 14+ | | SqBE17 17+ | | SqBE18 16+ | |
|---|---|---|---|---|---|---|---|---|
| | % positive | Total number | % positive | Total number | % positive | Total number | % positive | Total number |
| BE (IM) | 50% | 16 | 42% | 26 | 62% | 26 | 76% | 29 |
| GEJ/Cardia with IM | 22% | 9 | 18% | 11 | 64% | 11 | 70% | 10 |
| GEJ/Cardia without IM | 2% | 43 | 2% | 55 | 0% | 55 | 0% | 57 |
| columnar mucosa without IM taken from patients with concurrent IM at the same endoscopy | 0% | 5 | 0% | 9 | 11% | 9 | 11% | 9 |
| Normal Distal Esophagus-Squamous | 10% | 20 | 5% | 22 | 4% | 23 | 4% | 23 |

TABLE 10B-continued

| Marker CpG cut-off Value (% positive samples or total number of samples sequenced) | SqBE14-2 20+ | | SqBE16 14+ | | SqBE17 17+ | | SqBE18 16+ | |
|---|---|---|---|---|---|---|---|---|
| | % positive | Total number | % positive | Total number | % positive | Total number | % positive | Total number |
| Squamous Mucosa with REFLUX Esophagus | 17% | 6 | 0% | 8 | 0% | 9 | 0% | 10 |
| Eosinophilic Eosphagitis | 0% | 8 | 0% | 12 | 0% | 13 | 0% | 12 |
| Gastic Mucosa with IM | 0% | 5 | 0% | 7 | 13% | 8 | 14% | 7 |
| Gastric Fundic Mucosa without IM | 0% | 14 | 0% | 24 | 0% | 24 | 0% | 24 |
| *Helicobactor Pylori* Gastritis without IM | 14% | 7 | 8% | 13 | 46% | 13 | 8% | 13 |

Table 11 summarizes performance of different panels comprised of combinations of methylated DNA markers in FFPE tissue samples of the stomach and esophagus that capture different diagnostic categories other than Barrett's with high grade dysplasia and esophageal adenocarcinoma. Intestinal metaplasia is abbreviated as IM. Tables 9 and 10 denote for each marker the number of methylated cytosine bases required to be detected on a DNA sequence read to classify that read as methylated. Samples are detected as methylated if greater than or equal to 1% of DNA sequence reads are classified as methylated for any member of the marker panel.

TABLE 11A

| Marker combinations | VIM SqBE5 | VIM SqBE7 | VIM SqBE16 | VIM SqBE17 | VIM SqBE18 | SqBE5 SqBE7 | SqBE5 SqBE16 |
|---|---|---|---|---|---|---|---|
| BE (IM) | 92% | 88% | 92% | 88% | 97% | 71% | 70% |
| GEJ/Cardia with IM | 60% | 83% | 82% | 91% | 80% | 50% | 0% |
| GE/Cardia without IM | 0% | 2% | 2% | 7% | 0% | 3% | 3% |
| columnar mucosa without IM taken from patients with concurrent IM at the same endoscopy | 25% | 40% | 33% | 33% | 33% | 25% | 0% |
| Normal Distal Esophagus-Squamous | 8% | 6% | 9% | 9% | 9% | 8% | 8% |
| Squamous Mucosa with REFLUX Esophagus | 0% | 0% | 0% | 0% | 0% | 0% | 0% |
| Eosinophilic Eosphagitis | 0% | 0% | 0% | 8% | 0% | 0% | 0% |
| Gastic Mucosa with IM | 0% | 40% | 14% | 38% | 43% | 0% | 0% |
| Gastric Fundic Mucosa without IM | 0% | 5% | 0% | 0% | 8% | 7% | 0% |
| *Helicobactor Pylori* Gastritis without IM | 33% | 13% | 15% | 46% | 15% | 29% | 22% |

TABLE 11B

| Marker combinations | SqBE5 SqBE17 | SqBE5 SqBE18 | SqBE7 SqBE16 | SqBE7 SqBE17 | SqBE7 SqBE18 | SqBE16 SqBE17 | SqBE16 SqBE18 |
|---|---|---|---|---|---|---|---|
| BE (IM) | 80% | 91% | 57% | 79% | 94% | 78% | 92% |
| GEJ/Cardia with IM | 80% | 40% | 33% | 50% | 83% | 73% | 70% |
| GEJ/Cardia without IM | 9% | 0% | 2% | 9% | 2% | 8% | 2% |
| columnar mucosa without IM taken from patients with concurrent IM at the same endoscopy | 25% | 0% | 40% | 20% | 20% | 22% | 22% |
| Normal Distal Esophagus-Squamous | 8% | 8% | 6% | 0% | 6% | 9% | 5% |
| Squamous Mucosa with REFLUX Esophagus | 0% | 0% | 0% | 0% | 0% | 0% | 0% |
| Eosinophilic Eosphagitis | 20% | 0% | 0% | 10% | 0% | 10% | 0% |
| Gastic Mucosa with IM | 50% | 0% | 25% | 40% | 20% | 33% | 17% |
| Gastric Fundic Mucosa without IM | 0% | 7% | 5% | 5% | 5% | 0% | 8% |
| Helicobactor Pylori Gastritis without IM | 44% | 44% | 25% | 50% | 25% | 46% | 23% |

Table 12 summarizes performance of different panels comprised of combinations of methylated DNA markers in FFPE tissue samples of the stomach and esophagus that capture different diagnostic categories other than Barrett's with high grade dysplasia and esophageal adenocarcinoma. Intestinal metaplasia is abbreviated as IM. Tables 9 and 10 denote for each marker the number of methylated cytosine bases required to be detected on a DNA sequence read to classify that read as methylated. Samples are detected as methylated if greater than or equal to 10% of DNA sequence reads are classified as methylated for any member of the marker panel.

TABLE 12A

| Marker combinations | VIM SqBE5 | VIM SqBE7 | VIM SqBE16 | VIM SqBE17 | VIM SqBE18 | SqBE5 SqBE7 | SqBE5 SqBE16 |
|---|---|---|---|---|---|---|---|
| BE (IM) | 92% | 81% | 88% | 85% | 90% | 71% | 60% |
| GEJ/Cardia with IM | 60% | 83% | 82% | 91% | 80% | 50% | 0% |
| GEJ / Cardia without MI | 0% | 2% | 2% | 0% | 0% | 3% | 3% |
| columnar mucosa without IM taken from patients with concurrent IM at the same endoscopy | 0% | 0% | 0% | 11% | 11% | 0% | 0% |
| Normal Distal Esophagus-Squamous | 8% | 6% | 9% | 9% | 9% | 8% | 8% |
| Squamous Mucosa with REFLUX Esophagus | 0% | 0% | 0% | 0% | 0% | 0% | 0% |
| Eosinophilic Eosphagitis | 0% | 0% | 0% | 0% | 0% | 0% | 0% |
| Gastic Mucosa with IM | 0% | 20% | 14% | 13% | 29% | 0% | 0% |
| Gastric Fundic Mucosa without 1M | 0% | 5% | 0% | 0% | 0% | 7% | 0% |
| *Helicobactor Pylori* Gastritis without IM | 33% | 13% | 15% | 46% | 15% | 29% | 22% |

TABLE 12B

| Marker combinations | SqBE5 SqBE17 | SqBE5 SqBE18 | SqBE7 SqBE16 | SqBE7 SqBE17 | SqBE7 SqBE18 | SqBE16 SqBE17 | SqBE16 SqBE18 |
|---|---|---|---|---|---|---|---|
| BE (IM) | 70% | 91% | 57% | 71% | 81% | 74% | 81% |
| GEJ/Cardia with IM | 80% | 40% | 33% | 50% | 83% | 64% | 70% |
| GEJ/Cardia without FM | 0% | 0% | 2% | 2% | 2% | 2% | 2% |
| columnar mucosa without IM taken from patients with concurrent IM at the same endoscopy | 25% | 0% | 0% | 20% | 0% | 11% | 11% |
| Normal Distal Esophagus-Squamous | 8% | 8% | 6% | 0% | 6% | 9% | 5% |
| Squamous Mucosa with REFLUX Esophagus | 0% | 0% | 0% | 0% | 0% | 0% | 0% |
| Eosinophilic Eosphagitis | 0% | 0% | 0% | 0% | 0% | 0% | 0% |
| Gastic Mucosa with IM | 0% | 0% | 25% | 20% | 20% | 17% | 17% |
| Gastric Fundic Mucosa without IM | 0% | 0% | 5% | 5% | 5% | 0% | 0% |
| *Helicobactor Pylori* Gastritis without IM | 44% | 33% | 25% | 50% | 25% | 46% | 15% |

METHODOLOGIES

Somatic mutations in TP53 were detected using the following method. TP53 exons 2-11 were amplified using a multiplexed series of primer pairs covering all coding sequences and splice junctions. The primers contained additional 5' end sequences that were then used for secondary amplification that introduced barcode sequences and Illumina 15 and 17 sequences into the final PCR products. PCR products were mixed, purified and analyzed on an Illumina MiSeq instrument. Data analysis was performed using CLCBio software (Qiagen) and VariantStudio software (Illumina).

SEQUENCE LISTING

The patent contains a lengthy sequence listing. A copy of the sequence listing is available in electronic form from the USPTO web site (https://seqdata.uspto.gov/?pageRequest=docDetail&DocID=US12258632B2). An electronic copy of the sequence listing will also be available from the USPTO upon request and payment of the fee set forth in 37 CFR 1.19(b)(3).

We claim:

1. A method of identifying a human subject for treatment of esophageal neoplasia or metaplasia and treating, comprising:
    providing an esophageal sample obtained from the subject and treating with bisulfite to generate a plurality of bisulfite converted SqBE18 nucleic acid sequences;
    amplifying the plurality of bisulfite converted SqBE18 nucleic acid sequences to generate amplicons for each bisulfite converted SqBE18 nucleic acid, wherein each amplicon is a read and wherein the amplicon comprises a nucleotide sequence that is at least 90% identical to the nucleotide sequence of SEQ ID NOs: 8318, 8360, 8332, and/or 8374, or a fragment thereof, said fragment comprising at least 50 nucleotides in length;
    identifying methylated reads by measuring the number of methylated cytosines of the CpG dinucleotides in each amplicon of the bisulfite converted SqBE18 nucleic acid sequence, wherein a read is classified as a methylated read when at least 70% of the cytosines in the CpG dinucleotides of the individual amplicon of the bisulfite converted SqBE18 nucleic acid sequence is methylated;
    calculating a percentage of total reads that are methylated reads from the amplifying and measuring steps, wherein the esophageal sample obtained from the subject has at least 0.1% of the total reads that are methylated reads; and,
    administering to the human subject having an esophageal sample with at least 0.1% of the total reads that are methylated reads, cryotherapy, photodynamic therapy (PDT); radiofrequency ablation (RFA); laser ablation; argon plasma coagulation (APC); electrocoagulation (electrofulguration); esophageal stent, endoscopic mucosal resection (EMR), esophagectomy, anti-reflux surgery, and/or a therapeutic agent selected from a proton pump inhibitor, a Histamine H2 receptor blocking agents, an anti-reflux medication, a drug that moves food thru the gastrointestinal tract more quickly, carboplatin and paclitaxel; cisplatin and 5-fluorouracil (5-FU); ECF: epirubicine, cisplatin, and 5-FU; DCF: docetaxel, cisplatin, and 5-FU; Cisplatin with capecitabine; oxaliplatin and either 5-FU or capecitabine; doxorubicin, bleomycin, mitomycin, methotrexate, vinorelbine, topotecan, and irinotecan, trastuzumab, and/or ramucirumab.

2. The method of claim 1, wherein the human subject is administered a therapeutic agent selected from a proton pump inhibitor, a Histamine H2 receptor blocking agents, an anti-reflux medication, a drug that moves food thru the gastrointestinal tract more quickly, carboplatin and paclitaxel; cisplatin and 5-fluorouracil (5-FU); ECF: epirubicine, cisplatin, and 5-FU; DCF: docetaxel, cisplatin, and 5-FU; Cisplatin with capecitabine; oxaliplatin and either 5-FU or capecitabine; doxorubicin, bleomycin, mitomycin, methotrexate, vinorelbine, topotecan, and irinotecan, trastuzumab, and/or ramucirumab.

3. The method of claim 1, wherein the endoscopic mucosal resection (EMR), esophagectomy, and/or anti-reflux surgery is performed on the human subject.

4. The method of claim 1, wherein the sequence of the bisulfite converted nucleic acid sequences is determined by next-generation sequencing.

5. The method of claim 1, wherein the amplified portion comprises 21 dinucleotides that correspond to or are derived from 21 CpG dinucleotides present in the native non-bisulfite converted SqBE18 genomic sequence.

6. The method of claim 1, wherein primers used to amplify the portion of the bisulfite converted SqBE18 nucleic acid sequence comprise SEQ ID NOs: 8388 and/or 8402.

7. The method of claim 1, wherein the amplified portion comprises the nucleotide sequence of SEQ ID NOs: 8318, 8360, 8332 and/or 8374.

8. The method of claim 1, wherein the esophageal sample obtained from the subject is classified as a methylated sample when 1% to 3.5% of the reads are classified as methylated reads.

9. The method of claim 1, wherein the esophageal sample obtained from the subject is classified as a methylated sample when 1% to 3.11% of the reads are classified as methylated reads.

10. The method of claim 1, wherein the esophageal sample obtained from the subject is classified as a methylated sample when at least 3.11% of the reads are classified as methylated reads.

11. The method of claim 1, wherein the esophageal sample obtained from the subject is classified as a methylated sample when 0.5% to 3.5% of the reads are classified as methylated reads.

12. The method of claim 1, wherein the amplicon comprises a nucleotide sequence that is at least 95% identical to the nucleotide sequence of SEQ ID NOs: 8318, 8360, 8332 and/or 8374.

13. A method for detecting methylation status of an esophageal sample from a human subject suspected of having esophageal neoplasia or metaplasia, comprising:
    providing an esophageal sample obtained from the subject and treating with bisulfite to generate a plurality of bisulfite converted SqBE18 nucleic acid sequences;
    amplifying the plurality of bisulfite converted SqBE18 nucleic acid sequences to generate amplicons for each bisulfite converted SqBE18 nucleic acid, wherein each amplicon is a read and wherein the amplicon comprises a nucleotide sequence that is at least 90% identical to the nucleotide sequence of SEQ ID NOs: 8318, 8360, 8332, and/or 8374, or a fragment thereof, said fragment comprising at least 50 nucleotides in length;

measuring the number of methylated cytosines of the CpG dinucleotides in each amplicon of the bisulfite converted SqBE18 nucleic acid sequence, wherein a read is classified as a methylated read when at least 70% of the cytosines in the CpG dinucleotides of the individual amplicon of the bisulfite converted SqBE18 nucleic acid sequence is methylated;

calculating a percentage of total reads that are methylated reads from the amplifying and measuring steps, wherein the esophageal sample obtained from the human subject has at least 0.1% of the total reads that are methylated reads, whereby the esophageal sample obtained from the subject is classified as a methylated sample; and administering an endoscopy to the human subject with a methylated sample.

14. A method of diagnosing a subject that has an esophageal neoplasia or metaplasia, comprising:

providing an esophageal sample obtained from the subject and treating with bisulfite to generate a plurality of bisulfite converted SqBE18 nucleic acid sequences;

amplifying the plurality of bisulfite converted SqBE18 nucleic acid sequences to generate amplicons for each bisulfite converted SqBE18 nucleic acid, wherein each amplicon is a read and wherein the amplicon comprises a nucleotide sequence that is at least 90% identical to the nucleotide sequence of SEQ ID NOs: 8318, 8360, 8332, and/or 8374, or a fragment thereof, said fragment comprising at least 50 nucleotides in length;

wherein primers used to amplify the portion of the bisulfite converted SqBE18 nucleic acid sequence comprise SEQ ID NOs: 8388 and/or 8402;

measuring the number of methylated cytosines of the CpG dinucleotides in each amplicon of the bisulfite converted SqBE18 nucleic acid sequence, wherein a read is classified as a methylated read when at least 70% of the cytosines in the CpG dinucleotides of the individual amplicon of the bisulfite converted SqBE18 nucleic acid sequence are methylated; and, calculating a percentage of total reads that are methylated reads from the amplifying and measuring steps wherein the sample has at least 0.1% of the total reads that are methylated reads, whereby the subject is diagnosed with esophageal neoplasia or metaplasia.

* * * * *